United States Patent
Mody et al.

(10) Patent No.: US 7,736,360 B2
(45) Date of Patent: Jun. 15, 2010

(54) DEVICES AND METHODS FOR CREATING CONTINUOUS LESIONS

(75) Inventors: Dinesh I. Mody, Pleasanton, CA (US);
Dany Berube, Fremont, CA (US); Ross M. Carothers, San Jose, CA (US)

(73) Assignee: Microcube, LLC, Fremont, CA (US)

( * ) Notice: Subject to any disclaimer, the term of this patent is extended or adjusted under 35 U.S.C. 154(b) by 137 days.

(21) Appl. No.: 11/725,086

(22) Filed: Mar. 16, 2007

(65) Prior Publication Data
US 2007/0219546 A1 Sep. 20, 2007

Related U.S. Application Data

(60) Provisional application No. 60/783,367, filed on Mar. 17, 2006.

(51) Int. Cl.
*A61B 18/18* (2006.01)
(52) U.S. Cl. .......................... 606/41; 606/49
(58) Field of Classification Search ................. 606/41, 606/45–47
See application file for complete search history.

(56) References Cited

U.S. PATENT DOCUMENTS

| | | | |
|---|---|---|---|
| 5,582,609 A | 12/1996 | Swanson et al. | |
| 5,680,860 A | 10/1997 | Imran | |
| 5,814,028 A | 9/1998 | Swartz et al. | |
| 6,024,740 A | 2/2000 | Lesh et al. | |
| 6,106,522 A | 8/2000 | Fleischman et al. | |
| 6,164,283 A | 12/2000 | Lesh | |
| 6,454,758 B1 * | 9/2002 | Thompson et al. | 604/528 |
| 6,503,247 B2 | 1/2003 | Swartz et al. | |
| 6,544,262 B2 | 4/2003 | Fleischman | |
| 6,572,612 B2 | 6/2003 | Stewart et al. | |
| 6,640,120 B1 | 10/2003 | Swanson et al. | |
| 6,699,241 B2 | 3/2004 | Rappaport et al. | |
| 6,814,732 B2 * | 11/2004 | Schaer | 606/41 |
| 6,923,808 B2 | 8/2005 | Taimisto | |
| 6,955,173 B2 | 10/2005 | Lesh | |
| 6,960,206 B2 | 11/2005 | Keane | |
| 2003/0069570 A1 * | 4/2003 | Witzel et al. | 606/28 |

(Continued)

OTHER PUBLICATIONS

Douglas L. Packer et al., "Clinical Presentation, Investigation, and Management of Pulmonary Vein Stenosis Complicating Ablation for Atrial Fibrillation", Feb. 8, 2005, Circulation, pp. 546-554, US.

Carlo Pappone, MD, PhD, et al., "Atrio-Esophageal Fistula as a Complication of Percutaneous Transcatheter Ablation of Atrial Fibrillation", Jun. 8, 2004, Circulation, pp. 2724-2726, US.

*Primary Examiner*—Michael Peffley
(74) *Attorney, Agent, or Firm*—Levine Bagade Han LLP

(57) ABSTRACT

The present invention discloses devices and methods for creating multiple lesions using ablation devices in anatomical regions such as the heart, for example to treat cardiac arrhythmias. The present invention discloses methods and devices to create continuous lesions using area ablation devices. The present invention discloses various embodiments of reference assemblies for accurately positioning ablation devices having ablating portions, especially deployable ablation portions adapted for area ablation. The ablation devices are positioned using the reference assemblies in the anatomy to create one or more lesions. The present invention also discloses several method embodiments for creating continuous lesions using deployable ablating portions to produce two or more overlapping lesions.

86 Claims, 30 Drawing Sheets

U.S. PATENT DOCUMENTS

| | | |
|---|---|---|
| 2003/0093072 A1 | 5/2003 | Friedman |
| 2004/0019280 A1* | 1/2004 | Waner et al. ............... 600/466 |
| 2004/0106920 A1 | 6/2004 | Jenkins et al. |
| 2005/0004565 A1* | 1/2005 | Vanney ...................... 606/41 |
| 2005/0267453 A1 | 12/2005 | Wong et al. |
| 2005/0267463 A1 | 12/2005 | Vanney |

* cited by examiner

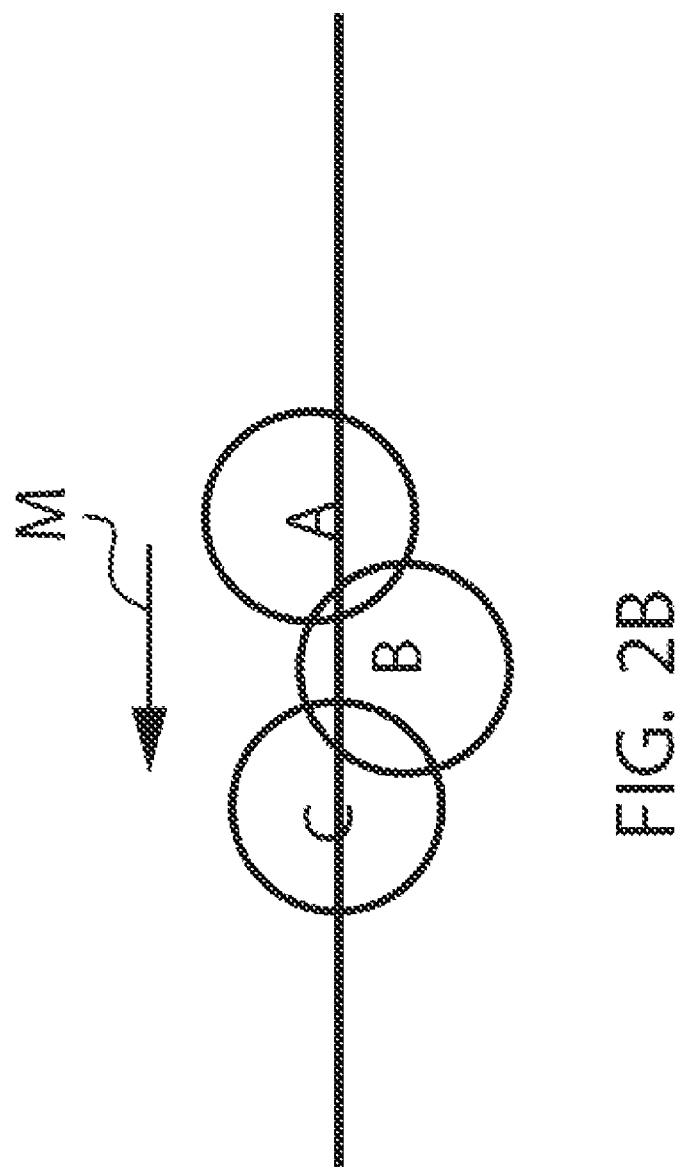

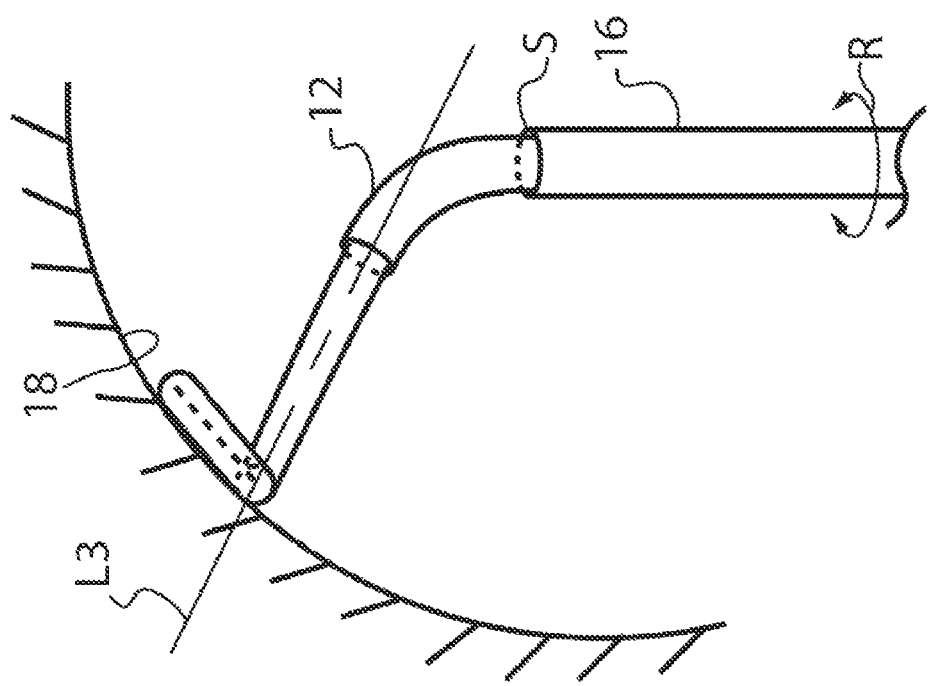

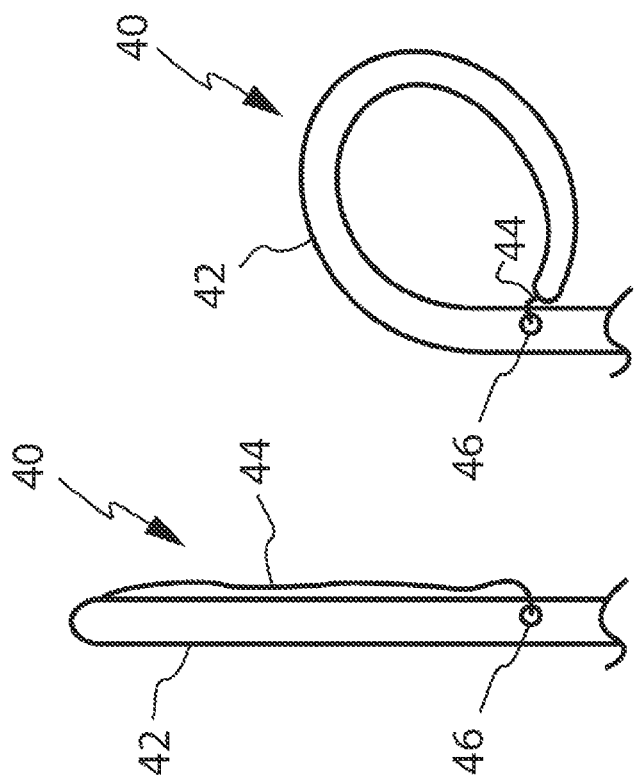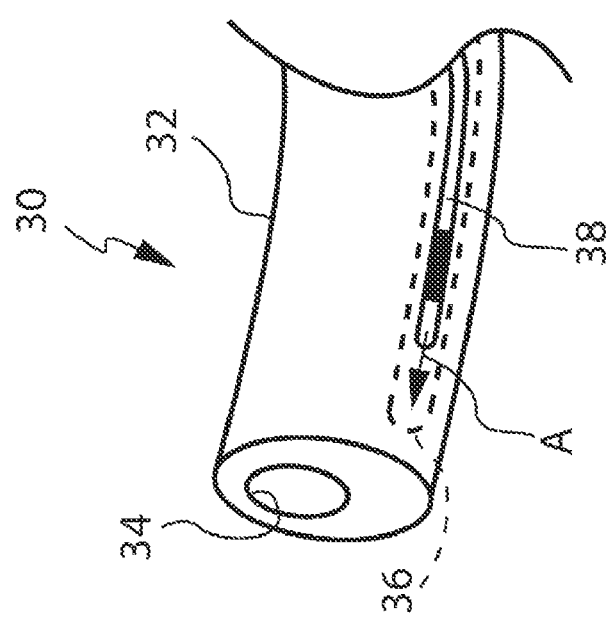
FIG.5C  FIG.5B  FIG.5A

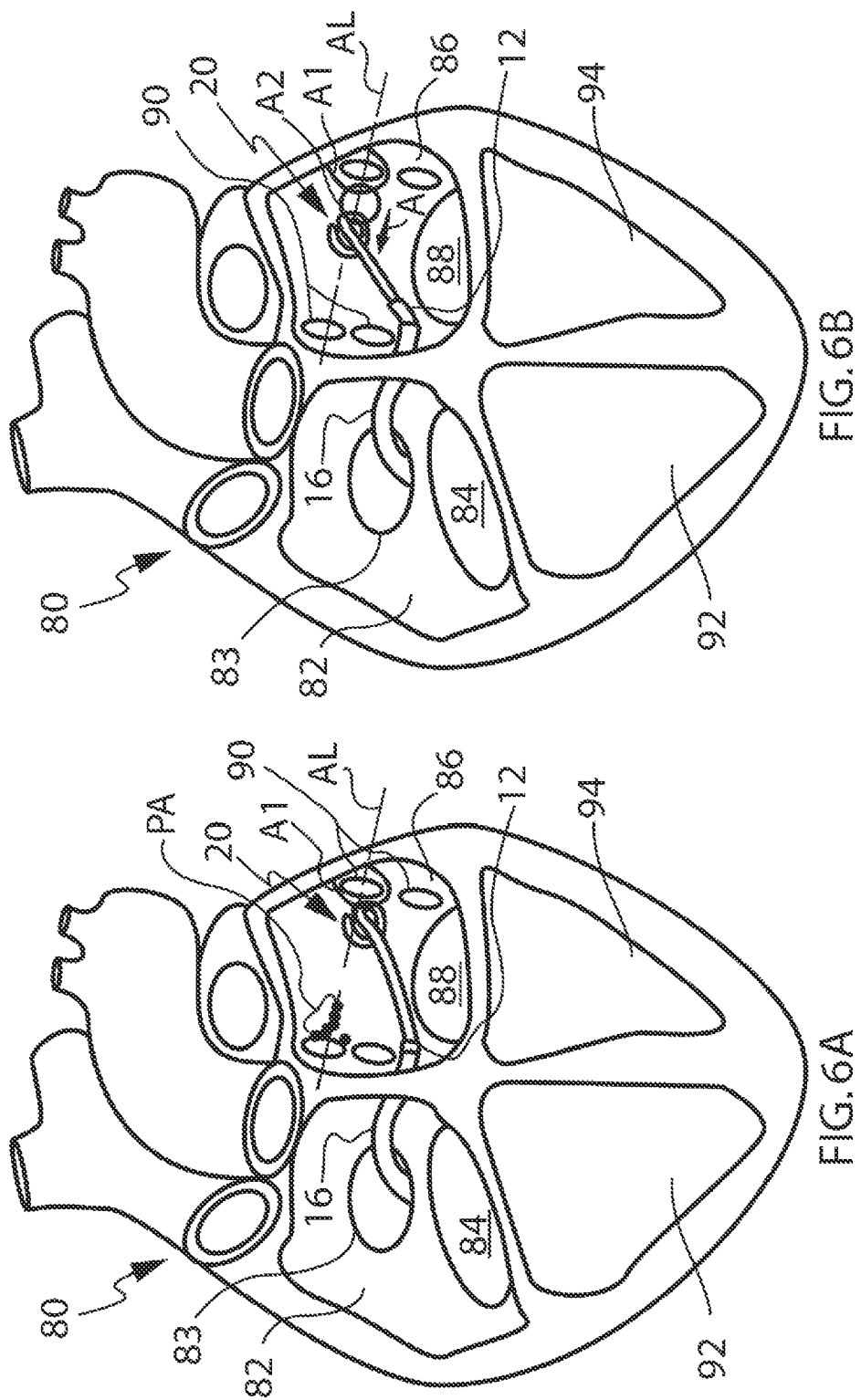

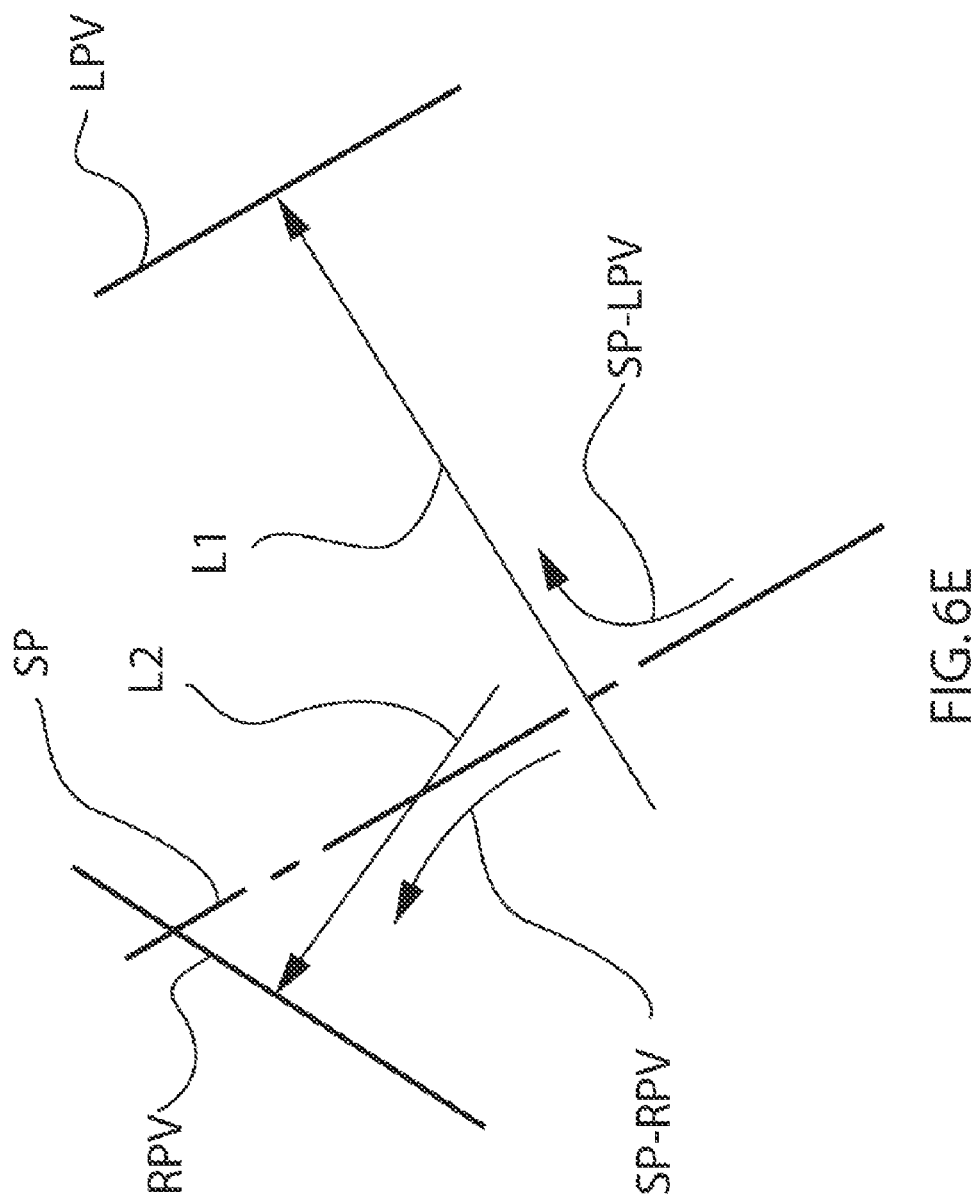

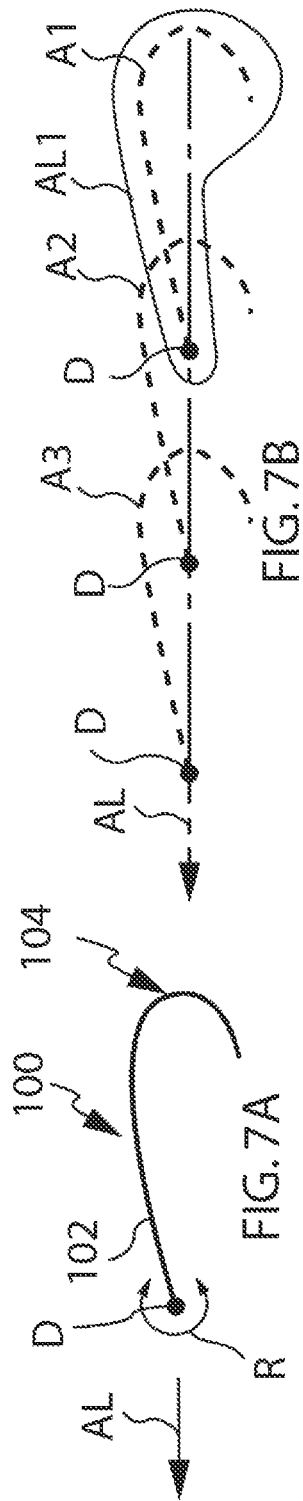

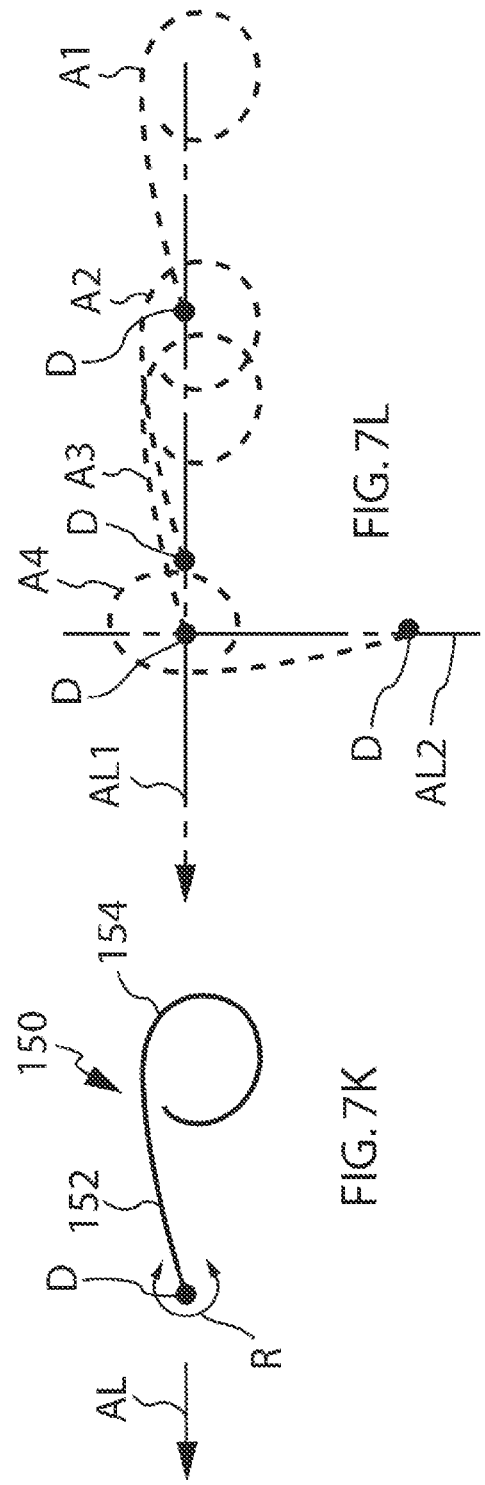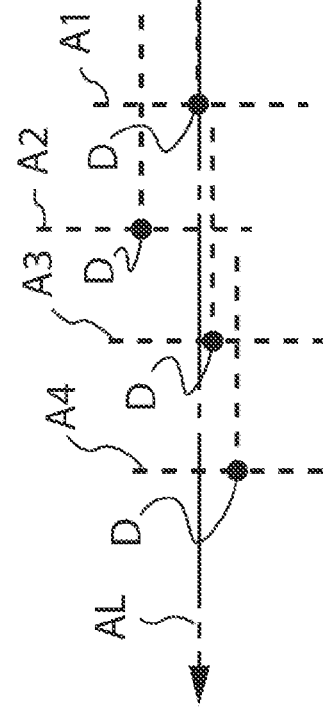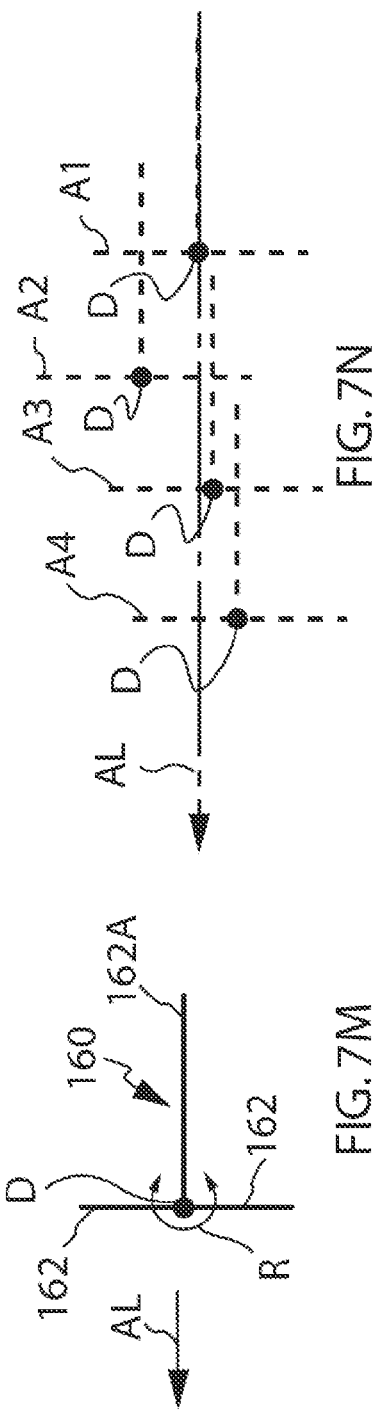

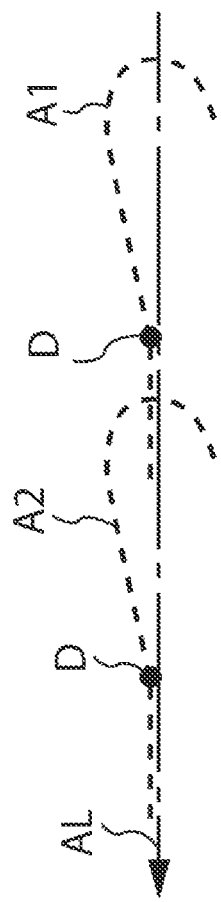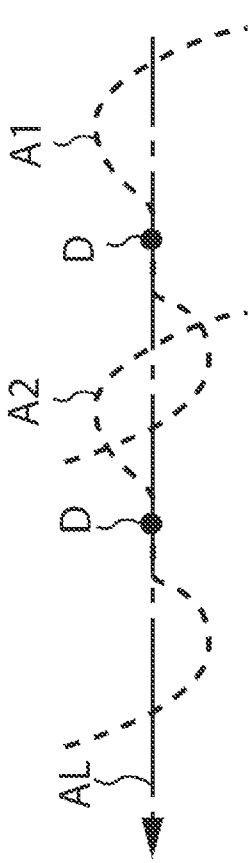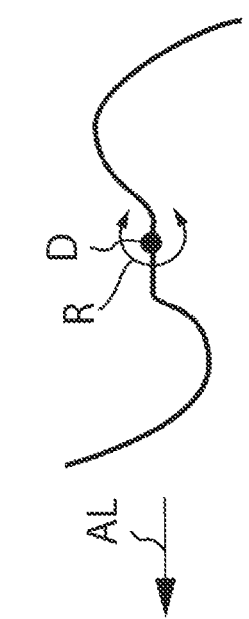

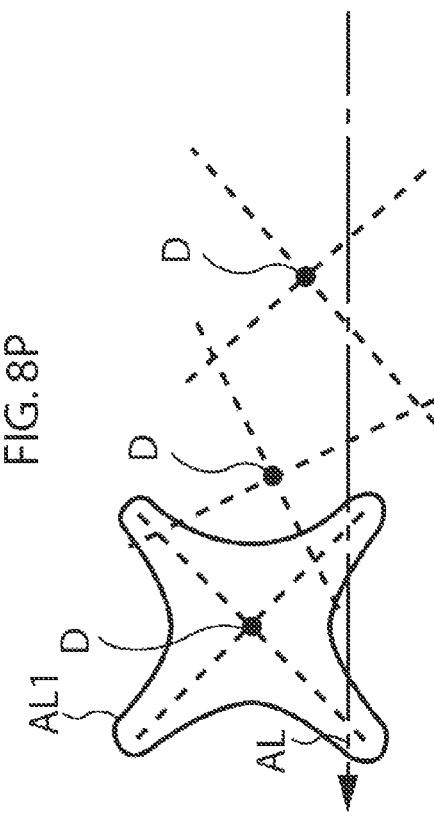
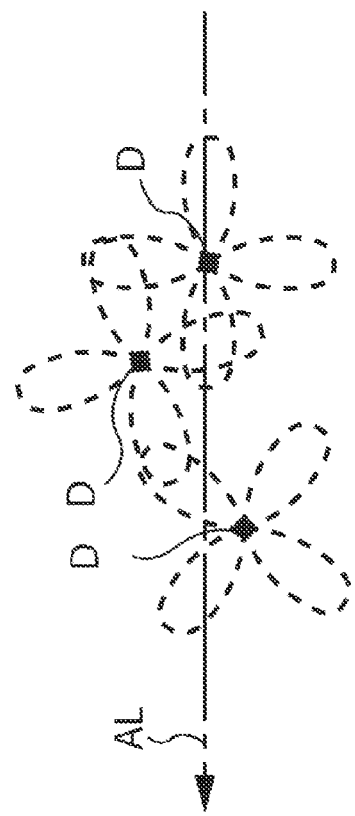
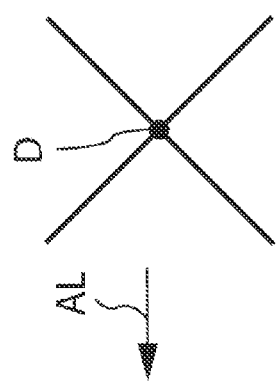
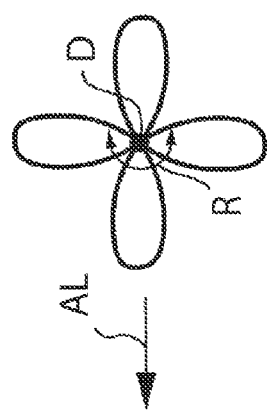
FIG. 8P
FIG. 8N
FIG. 8O
FIG. 8M

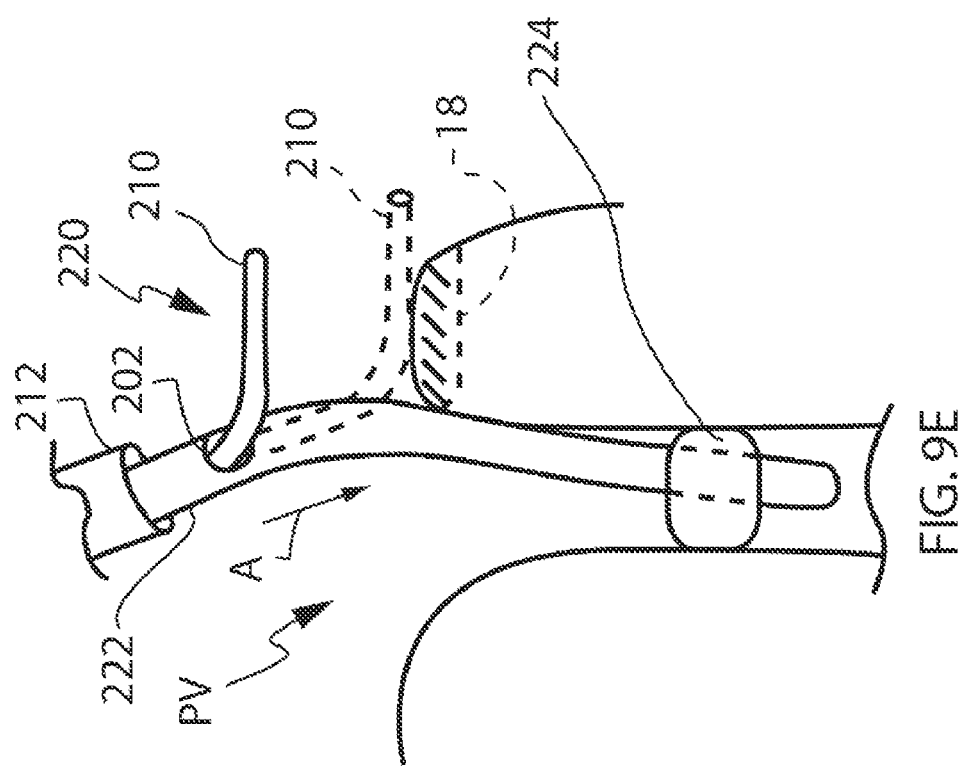

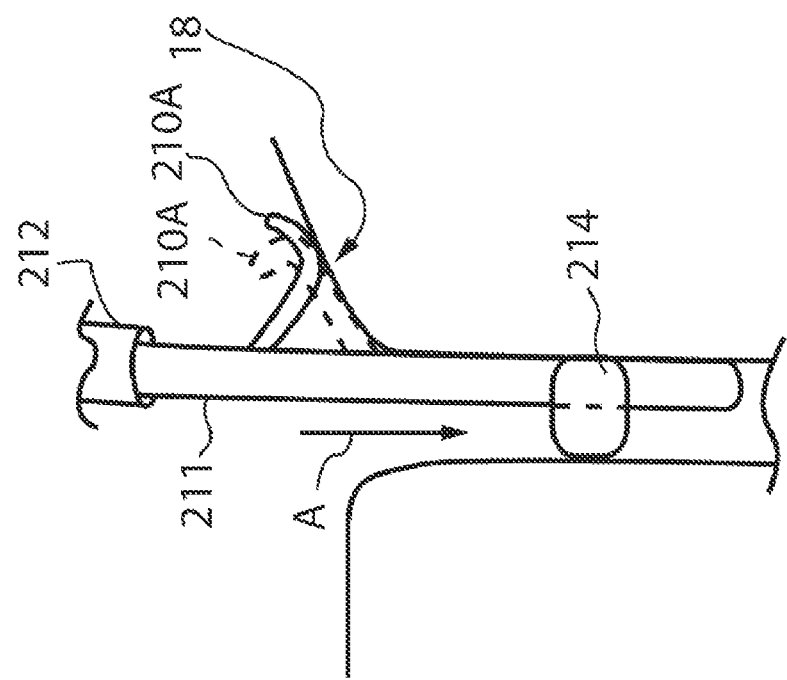
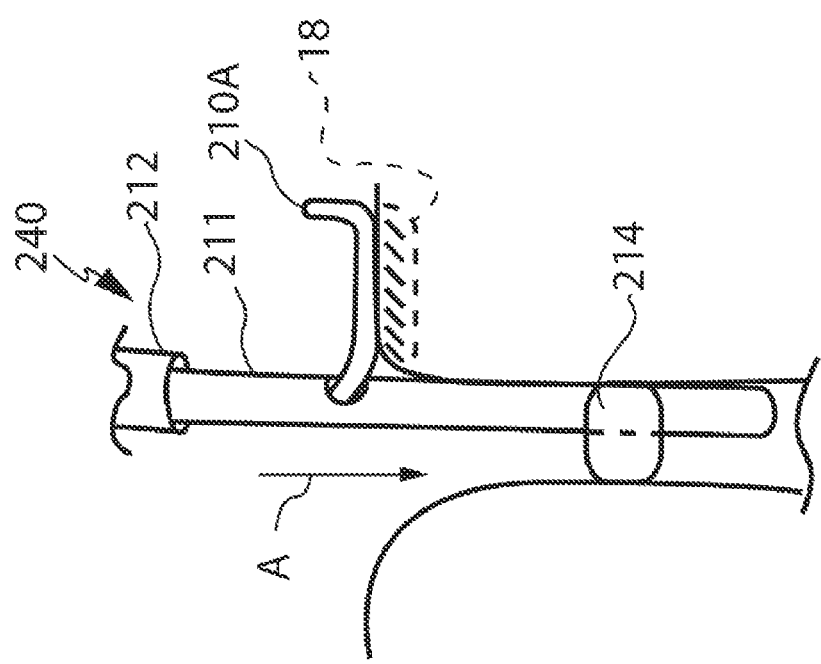

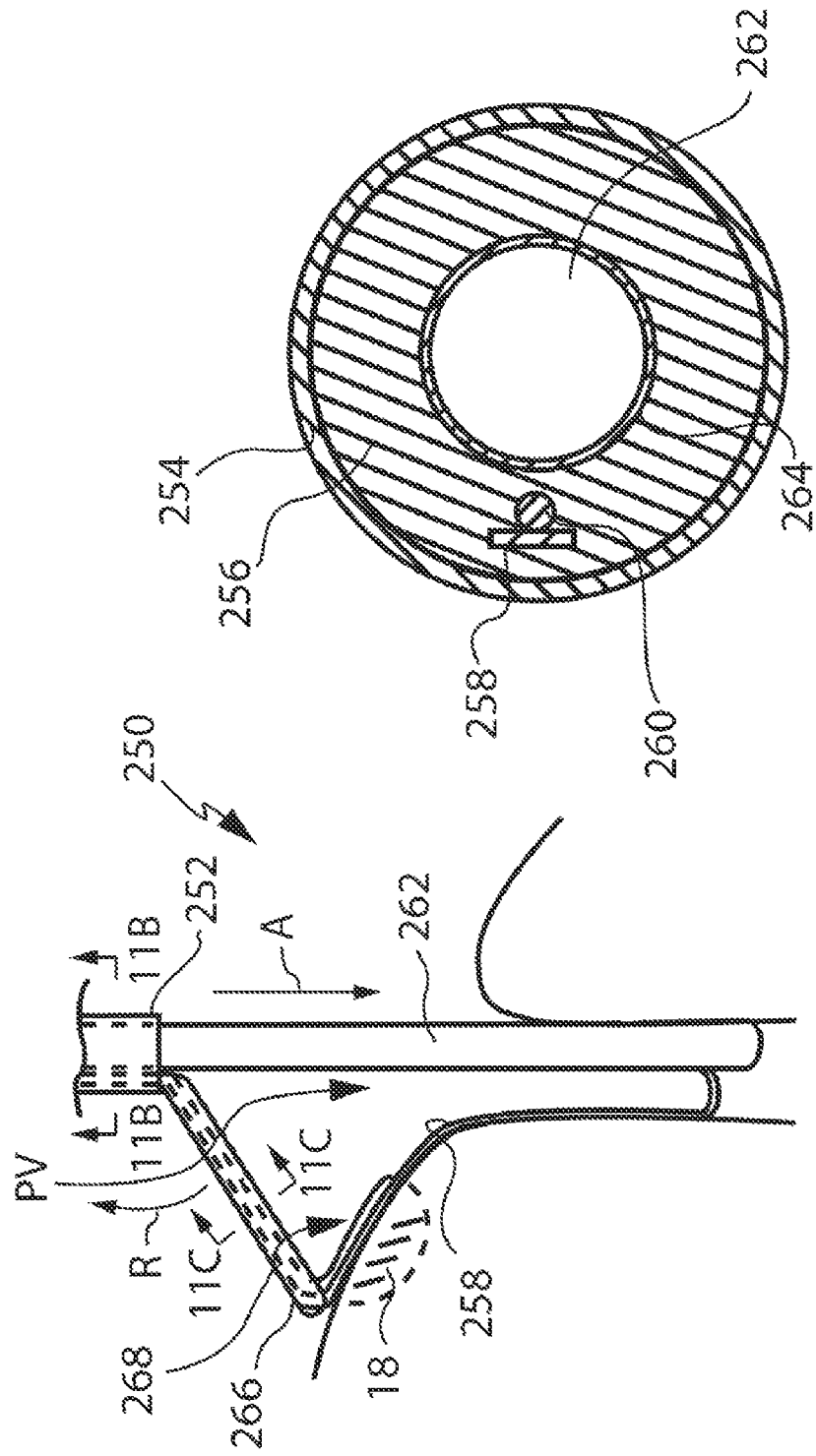

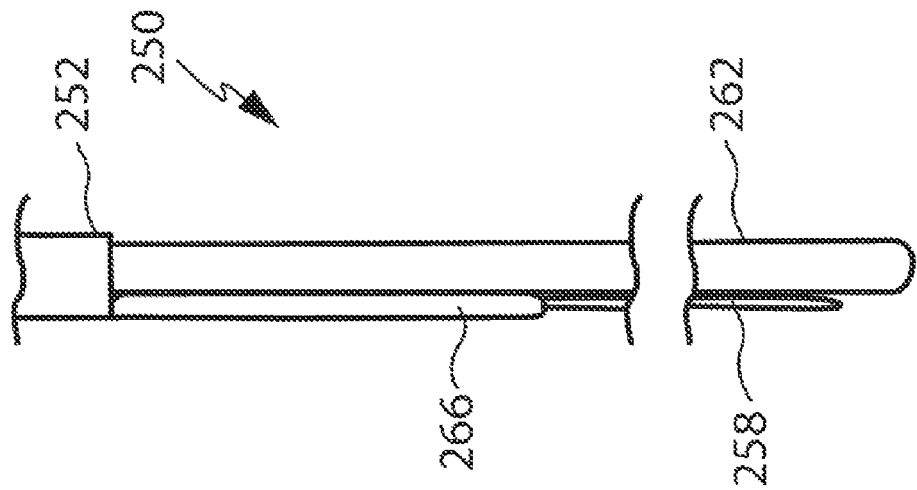
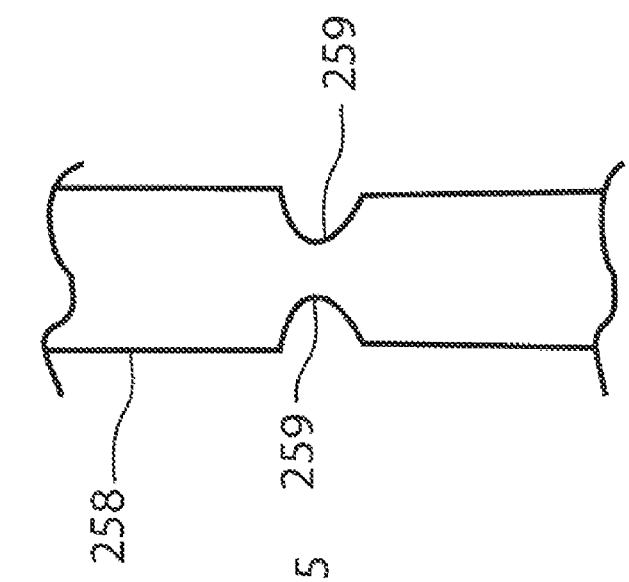
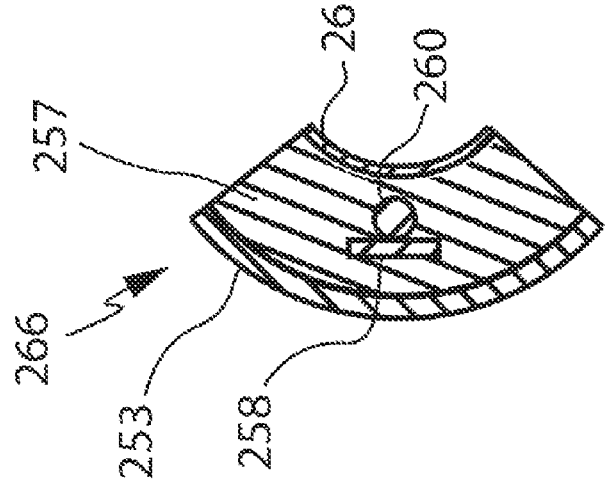

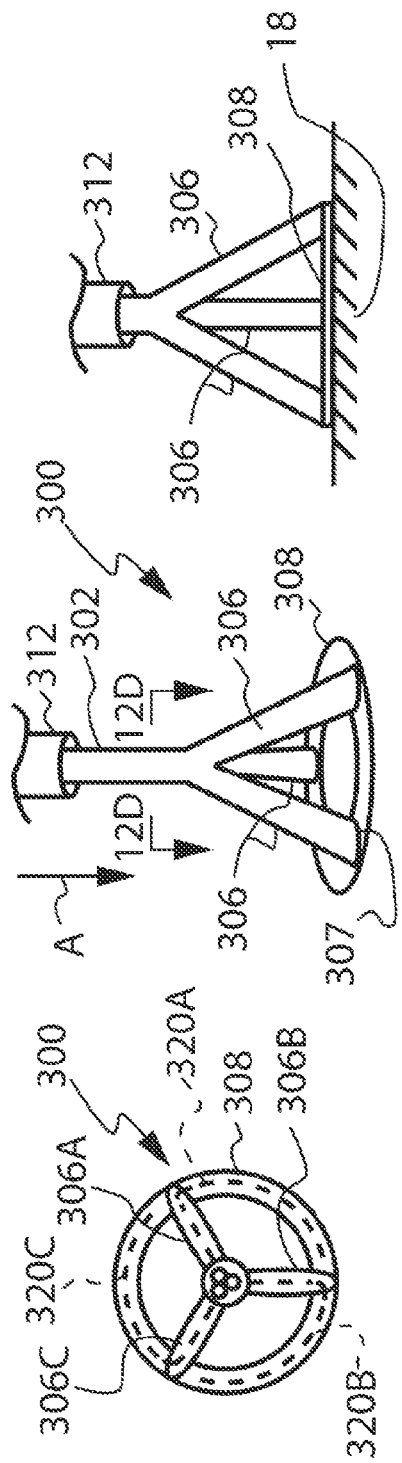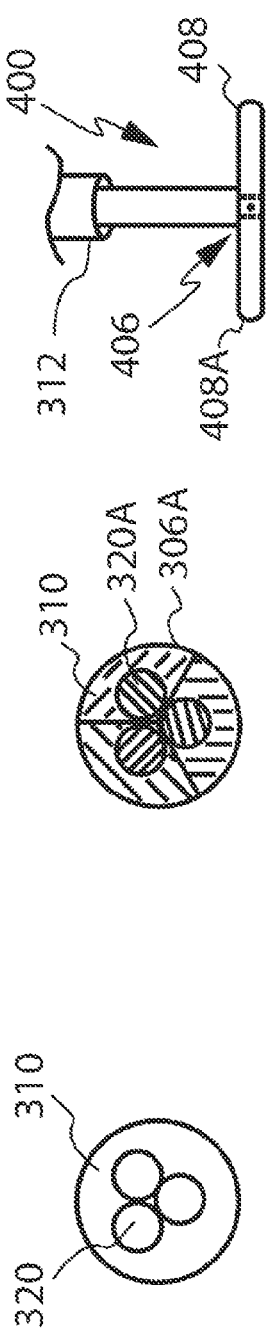

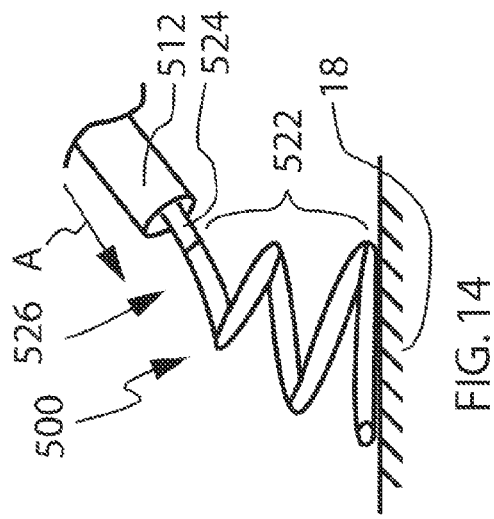
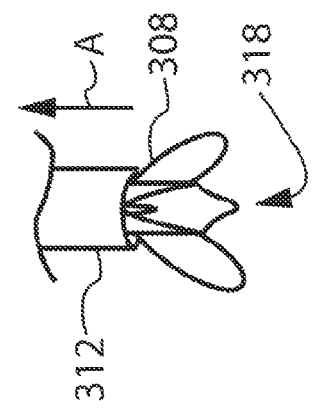
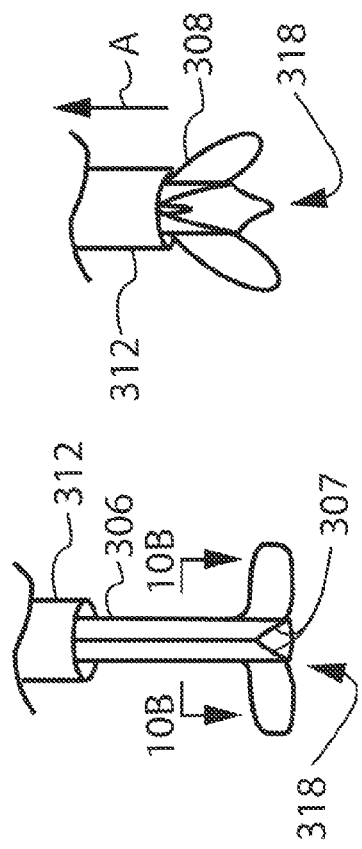
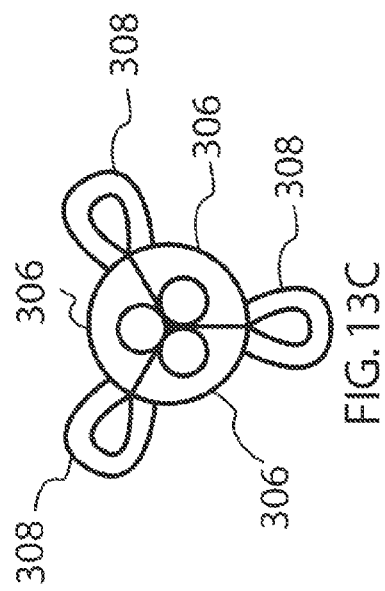

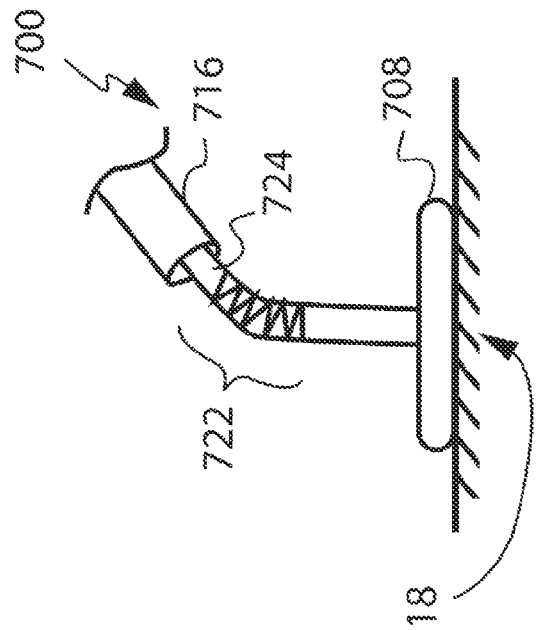
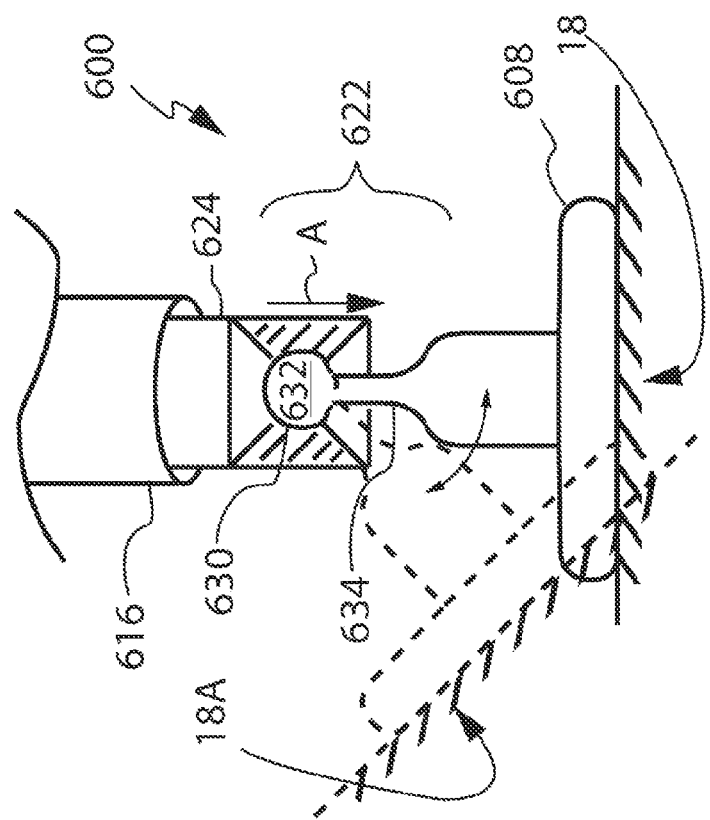
FIG. 15B
FIG. 15A

DEVICES AND METHODS FOR CREATING CONTINUOUS LESIONS

RELATED APPLICATIONS

This application claims the benefit of priority of provisional application 60/783367, filed Mar. 17, 2006, which is expressly incorporated herein by reference.

FIELD OF THE INVENTION

This invention relates to devices and methods for ablation of soft tissues of the body and, more specifically, to ablation devices designed to ablate cardiac tissue for the treatment of cardiac arrhythmias.

BACKGROUND OF THE INVENTION

Atrial fibrillation (AF) is a disorder found in millions of Americans. A heart in normal sinus rhythm receives an electrical signal from which it develops the well coordinated heart beat. AF occurs when something imparts a change to the electrical signal received by the heart resulting in, for example, uncontrolled and uncoordinated beating of the atria. While typically not fatal, the uncoordinated heart beat associated with AF results in blood pooling and clotting which, in turn, can lead to stroke. Approximately 15 percent of strokes occur in people with AF.

Various ablation systems, including catheters and surgical tools, are commonly used to ablate cardiac tissue to treat atrial fibrillation. The ablation system may incorporate an ablating portion which is placed upon the posterior wall of the left atrium, for example, where one or more lesions are then created as part of a desired lesion set or pattern.

With the move to less invasive procedures, a need has developed for catheters and surgical ablating tools which provide the user, typically an electrophysiologist or cardiac surgeon respectively, more precision and control, along with increased freedom of motion with respect to the controlled guidance of the ablating portions. Problems of guidance and control of ablation devices within the heart are further exasperated when preformed as a minimally invasive ablation procedure on a beating heart. Moreover, the varying anatomic differences from one patient to another lead to greater challenges involving the steering and positioning of the ablating portion of an ablation system within the left atrium.

With these general problems in mind, ablation systems have been designed which generally focus typically on one specific procedural requirement. For example, some ablation systems provide for an ablating portion mounted on and forming the distal tip of a steerable ablation catheter, the catheter being more easily guided and directed by a user to a target tissue site where tissue is to be ablated. However, even with these systems users find it difficult to reach certain areas of the left atrium, such as the intersection of tissue near the right superior pulmonary vein ostium and septal wall. Additionally, procedures performed with such systems are more time consuming since only a single small point lesion is created at any given time.

Other catheter systems are designed to create long linear lesions. While creating longer lesions allowing for faster procedure times when compared to point ablating systems, such linear ablating systems present additional challenges. Still other ablation systems are directed to isolating the pulmonary veins from the remaining atrial tissue. One such group of devices are designed to ablate a circumferential tissue region about a pulmonary vein ostium. Another group of circumferential ablation devices are designed to create circumferential tissue lesions along the inner wall of the pulmonary vein itself. While all such ablation systems provide a corresponding specialized advantage, they are generally problematic and present different challenges for the end user, as discussed in more detail immediately below.

Most catheter ablation systems require complex motions, for example movements in at least two planes, to move the ablating device from one ablation site to the next, in order to create the desired continuing lesion. Currently, most ablation procedures in the left atrium, for example, employ systems with tip electrodes which are mounted upon and form the distal tip end of the ablation catheter system. The user, typically an electrophysiologist, then guides the tip to a point of interest on the posterior wall of the left atrium and performs the point ablation procedure. Once a first point ablation is created, the user then guides the tip electrode to a subsequent point along the posterior wall and creates an additional point ablation, typically in communication with the first. This process continues until the desired lesion pattern is created through the interconnecting of numerous point ablations to create the desired lesion pattern, isolating the pulmonary veins from the remaining atrial tissue for example. These systems are sometimes referred to as "drag and burn" systems since they require the user to drag the tip electrode to a desired location and burn, or otherwise ablate, the target tissue at that location.

There are other limitations to point ablation systems. For example, while applying the necessary translational force to the tip portion to ensure proper contact with the target tissue for purposes of ablation, if the distal shaft portion of the ablating device is not substantially normal to the target tissue surface, the distal tip will slip, or otherwise move across the target tissue. This positioning or placement problem is exasperated during beating heart procedures where the user must predict and work in unison with cardiac movement when placing the ablating portion upon the target tissue surface. Another factor leading to placement problems is the fact that the endocardial surface of the left atrium posterior wall, apart from the location adjacent to the pulmonary vein ostia, can be quite smooth.

In practice, users of point ablation systems typically use costly support equipment to provide historic and current position information of the ablating portion with respect to anatomical cardiac structures and previously created lesions. The support equipment, while useful, is extremely costly and requires additional personnel to operate, ultimately increasing procedure costs.

Other drag and burn systems require numerous accessories and more complex methods which require additional time to complete the desired lesion set as part of the ablation procedure. See for example, U.S. Pat. No. 5,814,028 which discloses a system comprising numerous guide sheaths and ablation catheters designed, when specifically paired, to create numerous very specific ablation lines, or tracks, in the left and right atriums to treat atrial fibrillation. Aside from the inherent problems with point ablation devices, these relatively complex devices and methods require additional procedure time which can lead to user fatigue, and ultimately an unsafe working environment, as well as increasing procedure costs.

Still another problem with point ablation devices having ablating tip portions is the risk of perforation. As the device is advanced to engage the atrial tissue, translational force is applied by the user to ensure proper contact with the target tissue. Since the translational force is directed to the target tissue at a point, great care must be taken to ensure that excessive force is not used which may result in perforation of the atrial wall. Excessive force, coupled with the application of ablative energy, may increase the risk of atrio-esophageal fistula, especially for radiofrequency point ablating systems. See, for example, "Atrio-Esophageal Fistula as a Complication of Percutaneous Transcatheter Ablation of Atrial Fibrillation", Carlo Pappone, MD, PhD, et al., Circulation, Jun. 8, 2004 which discusses two cases where the left atrium was perforated with radio frequency based point ablation systems.

Creating continuous curvilinear lesions with linear ablating devices, while in theory providing an ability to create certain lesion patterns more quickly, is also problematic. Creating continuous lesions with curvilinear ablating devices requires the user to create a first lesion and then reposition the ablating portion adjacent to one end of the previously created linear lesion to create a second lesion, the second lesion being continuous with the first. With linear ablating devices, especially radio frequency based devices which, in theory, can create a more thin lesion line, due to viewing limitations during the procedure it is often very difficult to properly position the linear ablating portion in order to create the successive continuous linear lesions as part of a desired lesion pattern. Also, as with the point ablation procedures described above, typically support equipment is needed to ensure that the proper placement has been achieved.

See for example U.S. Pat. Nos. 5,582,609 and 6,544,262 which disclose various loop and spline structures used to create linear lesions. Such systems, however, in additional to the general problems stated above, require complex movements to ensure proper placement of the ablating portions of the devices for creation of continuous lesions, especially in a beating heart procedure. Often the user is required to move the ablating portion in multiple planes, deflections along two or more planes for example, in order to properly place the ablating portion. Moreover, the user may need to rotate the ablating catheter to further orient the ablating portion upon the target tissue and adjacent a previously created lesion in order to create a second lesion continuous with the first. Such complex movements make it very difficult to determine whether successive ablations are continuous without the use of additional procedural support equipment or other accessories.

Another problem with most linear ablating systems is they require a user to manipulate the elongated ablating portion to a point parallel to and adjacent target tissue. Such linear ablating systems become very dependent on the approach to the target tissue itself. This, in turn, limits the ability of the ablation system to create a multitude of lesions as part of a desired lesion pattern. This is often the case when the procedure is theoretically complete, however the patient is not in normal sinus rhythm. The user must then figure out where to create additional lesions in order to clinically complete the procedure. Such a decision should not be limited or dictated by the design of the ablation system itself. Rather, the ablation system should be able to create the desired lesion irregardless of its location or orientation within the heart.

See for example U.S. Pat. No. 6,106,522 which discloses linear ablating devices used to apply energy in a straight or curvilinear position in contact with tissue to form elongated lesion patterns. Such devices are problematic since they put heavy burdens on delivery systems, requiring such systems to steer the ablating portions to a point parallel to and adjacent target tissue. Creating the broad range of lesions necessary for the treatment of atrial fibrillation is very difficult with such systems, requiring a freedom of motion that is unavailable in the current offerings. Also, see U.S. Pat. No. 5,680,860 which teaches the creation of linear lesions through activation of certain radio frequency electrodes along the linear lesion line of interest, as part of a larger spiral embodiment. Such devices, however, are large in size and hard to properly place to ensure proper contact is made by and between the ablating portion and the target tissue, allowing the creation of the linear lesion. As is discussed in more detail below with respect to other spiral devices, such systems do not have ablating portions which apply sufficient contact force along the entire length of the ablating portion.

Moreover, such linear ablating devices as described above, due to the nature of their design, typically do not possess the necessary flexibility to be able to hold or retain the ablating portion adjacent to a target tissue while maintaining proper tissue contact, a necessity for radio frequency based ablation devices.

Additionally, linear ablating systems do not build on the procedural strengths electrophysiologists have acquired and further developed over the course of time performing a great number of ablation procedures utilizing steerable ablating systems with point ablation tip portions. Rather than approaching the target tissue from a direction more normal to the target tissue surface, many linear ablating systems require the user to learn new skills to perfect the associated ablation procedures.

As part of a desired lesion pattern, some electrophysiologists use the point ablating devices described above to create lesions around the pulmonary veins, isolating one pulmonary vein from the left atrial tissue for example. Such isolating procedures require precise placement of the ablating portion near a pulmonary vein ostium. While some areas in the left atrium, for example, are more readily accessible, other areas, such as near the junction between the septal wall and the ostium of the right superior pulmonary vein, are not as easily accessible. Placement of the ablating portion near a right pulmonary vein ostium via a transseptal approach is especially challenging since such placement requires sharp catheter bends near the transseptal opening along the septal wall. As with point ablating procedures described above, many times the user simply relies on costly lab equipment to try to guide him to a desired target tissue location.

Others have simply tried to encircle a pulmonary vein and simultaneously ablate a circumferential region of tissue surrounding the vein. See for example U.S. Pat. Nos. 6,024,740, 6,164,283 and 6,955,173 which disclose expandable balloon based ablating structures designed to simultaneously or instantaneously create circumferential ablations around a pulmonary vein ostium. These expandable balloon based ablation devices typically include anchoring devices, or other protruding devices or structures, which are used for anchoring or guiding the device to the ostium of the pulmonary vein. These structures prevent the use of such devices for creation of associated linear lesions as part of a desired lesion pattern. Such expandable balloon structures also substantially block the blood flowing through the pulmonary vein and into the left atrium, the true consequences of which are not completely understood.

Such circumferential ablating devices also generally do not provide consistent circumferential contact between the ablating portion and the circumferential tissue surrounding the ostium, such contact being required for creation of a corresponding circumferential lesion. This is more noticeable in radio frequency ablation systems or thermal conductive ablation systems, such as cryogenic or resistive heating ablation systems for example, which require direct tissue contact for ablative current to flow or sufficient thermal conduction to occur, respectively, for tissue ablation. For example, balloon structures for cryogenic ablating systems are typically fixed in overall dimension and do not posses the flexibility needed to properly engage a circumferential region of tissue surrounding an ostium of a pulmonary vein, the specific anatomic shape which can vary dramatically from patient to patient.

Radiofrequency ablating devices which rely on a continuous elastic or superelastic metallic structure, such as nitinol for example, for both placement and ablation are particularly susceptible to contact issues since these materials, despite their name, do not have the requisite flexibility to engage a continuous tissue surface in order to create a continuous lesion therein. While thermal conduction may complete lesions associated with some of these problematic non-contact areas, not all may be resolved. Nor is there a simple way to discover where the discontinuity lies since the exact degree of contact between the ablating portion and the target tissue, along the length of the ablating portion, is not readily known.

See also U.S. Pat. Nos. 6,572,612, 6,960,206 and 6,923,808 which disclose loop devices designed to engage a circumferential region of tissue surrounding a pulmonary vein ostium, immediately and simultaneously ablating the circumferential region. As with the balloon structures discussed above, while the immediate devices possess the flexibility to longitudinally pass through a guiding catheter and then take on a circumferential shape once within the left atrium, they are not flexible enough to be able to adequately engage the non-linear circumferential region of tissue consistent with the creation of a continuous lesion thereupon.

Most of such spiral ablation systems are also flawed due to their inability to apply requisite constant contact pressure between the length of the spiral structures and the corresponding circumferential region of tissue. Rather, as the user applies axial force, the force is only applied to the most proximal section of the ablating portion, the most distal section not necessarily making the preferred tissue contact for formation of a corresponding continuous lesion.

More recently, ablating devices have been developed to help address the tissue contact problem associated with ablating circumferential regions of tissue around a pulmonary vein ostium. See for example, U.S. Pub. Nos. US20040106920 and US20050267453 which disclose systems which laterally ablate tissue at a given radial position near a pulmonary vein ostium. However, such systems are problematic since they rely on a generally consistent tissue surface along the radial path about the pulmonary vein ostium. As the system is radially rotated in order to create the desired circumferential lesion, at some point the ablating device may no longer be engaging the target tissue due to the specific anatomic structure of the patient. To resolve this issue, it may be needed to advance the ablating portion toward the pulmonary vein in order to laterally engage target tissue adjacent to the pulmonary vein ostium. However, such advancement, considering this lateral ablating approach, may jeopardize the continuity of the currently created lesion with previously created lesions.

Some ablation devices have been developed to ablate the inner wall of the pulmonary vein itself, at a point within the pulmonary vein. For example, U.S. Pat. No. 6,503,247 and U.S. Pub. No. US20050267463 disclose systems for ablating the inner wall of the pulmonary vein to isolate undesirable signals originating in the pulmonary veins from the remainder of the left atrial tissue. Such systems are undesirable since ablation of the inner wall of the pulmonary vein can lead to stenosis which, in turn, can then lead to serious respiratory problems including shortness of breath or dysnpea, severe coughing or hemoptysis, chest pain and pneumonia. See, for example, "Clinical Presentation, Investigation, and Management of Pulmonary Vein Stenosis Complicating Ablation for Atrial Fibrillation," Douglas L. Packer, M.D., et al., Circulation, Feb. 8, 2005 which discusses such problems.

More recently, various ablation systems have been developed which allow for the creation of larger area ablations for the treatment of ventricular tachycardia. See U.S. Pat. Nos. 5,582,609, and 6,699,241 for exemplary systems used to create large volumetric lesions for the treatment of ventricular tachycardia. Neither address creating continuous lesions with area ablations for the treatment of atrial fibrillation, as in the present application.

SUMMARY OF THE INVENTION

Accordingly, it is a primary object of the present invention to provide systems and methods for creating area ablations from which continuous lesions in a target tissue, as part of a desired lesion pattern, can be formed.

In an aspect of the invention a continuous lesion is created in biological tissue by an ablation device having a working end which includes a flexible ablating portion adapted to ablate an area of target tissue having a length and width greater than or equal to the target tissue depth.

In yet another aspect of the invention a continuous lesion is created in biological tissue by an ablation device having an ablation portion as part of a working end, the ablation portion having a length and width greater than or equal to the target tissue depth.

In another aspect of the invention a continuous lesion is created in biological tissue by an ablation device having a working end comprising an ablating portion adapted to define a substantially planar geometric shape upon deployment, the ablating portion adapted to ablate at least a surface area of tissue generally corresponding to the geometric shape.

In yet another aspect of the invention a continuous lesion is created in biological tissue by an ablation device having a working end comprising an ablating portion adapted to define a substantially planar geometric shape upon deployment, the ablating portion adapted to ablate at least a desired surface area of tissue, the desired surface area not directly corresponding to the geometric shape.

In still another aspect of the invention an area lesion is created in biological tissue forming at least two distinct barriers to reliably block substantially all possible conduction paths.

In yet another aspect of the invention an ablation device is provided which includes an ablation portion which can be slidably positioned within a guide or delivery sheath, the ablating portion taking on a predetermined geometric shape as it exits the sheath.

In another aspect of the invention an ablation device is provided with an ablating portion adapted to be operably configured in at least a first and a second orientation with respect to the target tissue, in the first orientation the ablating portion takes on a first predetermined geometric shape with respect to the target tissue and in the second orientation the ablating portion takes on a second predetermined geometric shape with respect to the target tissue. The first and second geometric shapes may be linear shapes, curvilinear shapes, substantially planar geometric shapes, or a combination thereof.

It is another object of some aspects of the present invention to provide ablation systems which include deflectable distal portions which act to self-align at least part of an ablating portion adjacent a target tissue. In one aspect of the invention an ablation system is provided having a deflectable distal portion which acts to self-align at least part of an ablating portion adjacent a target tissue.

In yet another aspect of the invention an ablation system is provided having a flexible joint which, upon tissue contact, allows the ablating portion to deflect toward a target tissue.

In another aspect of the invention an ablation system is provided having a flexible joint proximal to an ablating portion adapted to define a first operating position upon deployment. Upon tissue contact, the flexible joint deflects the ablating portion into a second operating position toward the target tissue.

It is another object of some aspects of the present invention to provide ablation systems and methods giving a user the ability to accurately position the distal ablating portion of an ablation device to create one or more desired lesions as part of a desired lesion pattern. In one aspect of the invention various steering systems are provided.

In another aspect of the invention a steering system is provided which includes a first sheath and a second sheath each having a lumen which travels therethrough, the first sheath and second sheath operably cooperating to define and direct a distal opening from which an ablating portion exits toward a target tissue. In an aspect of the invention the first sheath translates within the lumen of the second sheath, the first sheath being more flexible than the second sheath, the distal portion of the first sheath having a preformed curvilinear shape, the first sheath translating with respect to the second sheath, and the distal portion of the first sheath taking on its preformed curvilinear shape as it exits the distal opening of the second sheath. In another aspect of the invention the second sheath translates within the first sheath, the first sheath being more flexible than the second sheath, the distal ends of each sheath being substantially initially aligned, the distal portion of the first sheath having a preformed curvilinear shape, the second sheath translating with respect to the first sheath, and the distal portion of the first sheath taking on its preformed curvilinear shape as the second sheath is translated within the first sheath.

In yet another aspect of the invention a steering system is provided which includes a first sheath and a second sheath which operably cooperate to define an initial steering direction, the first sheath and second sheath are rotatable with respect to each other further defining additional steering directions.

In another aspect of the invention a steering system is provided which includes a first and a second sheath which cooperate to operably translate with respect to each other and define an operative direction for directing an ablating device which translates therethrough, the translation being remotely controlled through operation of a control on a handle portion, the handle portion or control providing feedback to the user relative to the amount of translation of each sheath and, ultimately, the operative direction. Feedback can be provided through raised or depressed regions, or other discriminations on the surface of the handle portion, as well as auditory or visual indications. Further, feedback can be provided through data analysis of the sheath movements and provided for viewing by the user, such as on a cathode ray tube display or the like.

In another aspect of the invention a steering system is provided which is adapted to let the user define the location and radius of curvature along the longitudinal axis of an ablation device, which curvature can be imparted onto the ablating portion of the ablation device which translates therethrough.

It is another aspect of this invention to provide a steering system which is adapted to let the user adaptively define one or more deflection points along the longitudinal axis of an ablation device of the steering system.

It is still another aspect of this invention to provide a steering system which is adapted to work with existing ablation catheter systems, enhancing the positioning and performance of the existing ablation catheter systems.

Another object of the various aspects of the invention is to provide an ablation system adapted to provide requisite contact force between an ablating portion and a target tissue. In an aspect of the invention the contact force is substantially equal about various points of contact as between the ablating portion and target tissue.

In another aspect of the invention an ablation system is provided, the ablation system adapted to provide requisite contact force between an ablation portion and a target tissue, the source of the contact force being provided from a generally centralized location with respect to the ablating portion. In yet another aspect of the invention the contact force is transmitted to the ablation portion through one or more spline members. In still another aspect of the invention the spline members can form a part of the ablating portion.

Yet another object of the various aspects of the invention is to provide systems and methods which reduce the time required to perform tissue ablation and, more particularly, cardiac tissue ablation.

Still another object of the various aspects of the invention is to provide systems and methods which are not dependant on a particular ablative energy, but rather can utilize various energies, alone or in combination.

Yet another object of the various aspects of the invention is to provide systems and methods which provide the user tactile feedback. In one aspect the ablating portion of the ablation device is adapted to transmit certain forces related to the ablation procedure to the user. In another aspect of the invention the tissue contact forces are transmitted through the ablation device to the user allowing the user to react to such forces. In still another aspect of the invention the user reducing the applied force upon detection of high tissue contact forces.

Still another object of the various aspects of the invention is to provide systems and methods which enable the ablation of target tissue at a known orientation with respect to a defined reference point. In one aspect of the invention positioning of the ablating portion of an ablation device with respect to the reference is achieved through coarse movements.

In another aspect of the invention the defined reference is an anatomical structure. In yet another aspect of the invention the defined reference is an inner wall of a pulmonary vein. In still another aspect of the invention the defined reference is the left atrial appendage or a surface thereof.

In another aspect of the invention the defined reference is a point along the ablating device itself. In still another aspect of the invention the defined reference is along an ablation portion of the ablating device. In yet another aspect of the invention the defined reference remains stationary while the ablation portion of the ablating device moves with respect thereof.

In yet another aspect of the invention the defined reference is an exit point of a delivery or guide sheath, or other steering system, from which the ablating device exits to engage a target tissue location.

Yet another object of the various aspects of the invention is to provide systems and methods of varying procedural and anatomical approaches. In one aspect of the invention the approach is a surgical approach, achieved through the use of a surgical device or tool. In another aspect of the invention the approach is a catheter approach, achieved through the use of a catheter system.

In yet another aspect of the invention the anatomical approach is an apical approach with respect to the heart.

In another aspect of the invention the anatomical approach is through an intercostal space.

In still another aspect of the invention the anatomical approach is a subxyphoid approach.

In another aspect of the invention the procedural and anatomical approach is through a thoracic opening.

In another aspect of the invention the procedural and anatomical approach is through an open chest.

In yet another aspect of the invention the procedural and anatomical approach is through a minimally invasive opening.

In yet another aspect of the invention the procedural and anatomical approach is a transseptal approach.

In another aspect of the invention the procedural and anatomical approach is a retrograde approach.

In still another aspect of the invention the procedural and anatomical approach is on a beating heart.

In another aspect of the invention the procedural and anatomical approach is performed while the heart is on-pump.

BRIEF DESCRIPTION OF THE DRAWINGS

FIG. 2B is an exemplary lesion pattern formed by the ablation device of FIG. 1.

FIG. 4E is a perspective view depicting an exemplary embodiment of an ablation device cooperating with the steering system including the delivery sheath of FIG. 4A and the guide sheath of FIG. 4B.

FIG. 5A is a perspective view depicting another steering system, in accordance with various aspects of the present invention.

FIG. 5B is an elevational view depicting another steering system, in accordance with the various aspects of the present invention, the steering system in a first operative condition.

FIG. 5C is an elevational view depicting the steering system of FIG. 5B in a second operative condition.

FIGS. 6A-6B depict a method in accordance with certain aspects of the present invention.

FIG. 6E depicts exemplary general points of interest within the left atrium of the heart and general approach geometries with respect to the points of interest.

FIG. 9E depicts an elevational view of another exemplary embodiment incorporating an ablating element in accordance with various aspects of the present invention.

FIGS. 10A-10B depict elevational views of another exemplary embodiment incorporating an ablating element in accordance with various aspects of the present invention.

FIG. 11A depicts an elevational view of another exemplary embodiment incorporating an ablating element in accordance with various aspects of the present invention.

FIGS. 11B-11C are crossectional views of the embodiment of FIG. 11A.

FIG. 11D depicts a defined point of flexing as part of the embodiment of FIG. 11A.

FIG. 11E depicts the embodiment of FIG. 11A in a collapse configuration for translation through a delivery system.

FIG. 12A is a partial crossectional view of another embodiment in accordance with various aspects of the present invention.

FIG. 12B is a side perspective view of the embodiment of FIG. 12A.

FIG. 12C is a side elevation view of the embodiment of FIG. 12A.

FIGS. 12D and 12E are crossectional views of the embodiment of FIG. 12A.

FIG. 12F is a side elevation view of another embodiment in accordance with various aspects of the present invention.

FIG. 13A is a side elevation view of the embodiment of FIG. 12A depicting the distal portion in a collapse state allowing for transport via a delivery system.

FIG. 13B is another side elevation view of the embodiment of FIG. 12A depicting the distal portion in a collapsed state allowing for transport via a delivery system.

FIG. 13C is a crossectional view of the embodiment of FIG. 12A with the distal portion in a collapse state.

FIG. 14 is another exemplary embodiment, in accordance with various aspects of the present invention, incorporating a flexible joint structure.

FIGS. 15A-15B depict additional exemplary embodiments incorporating flexible joint structures.

DETAILED DESCRIPTION OF THE PREFERRED EMBODIMENTS

Figures 1, 2:
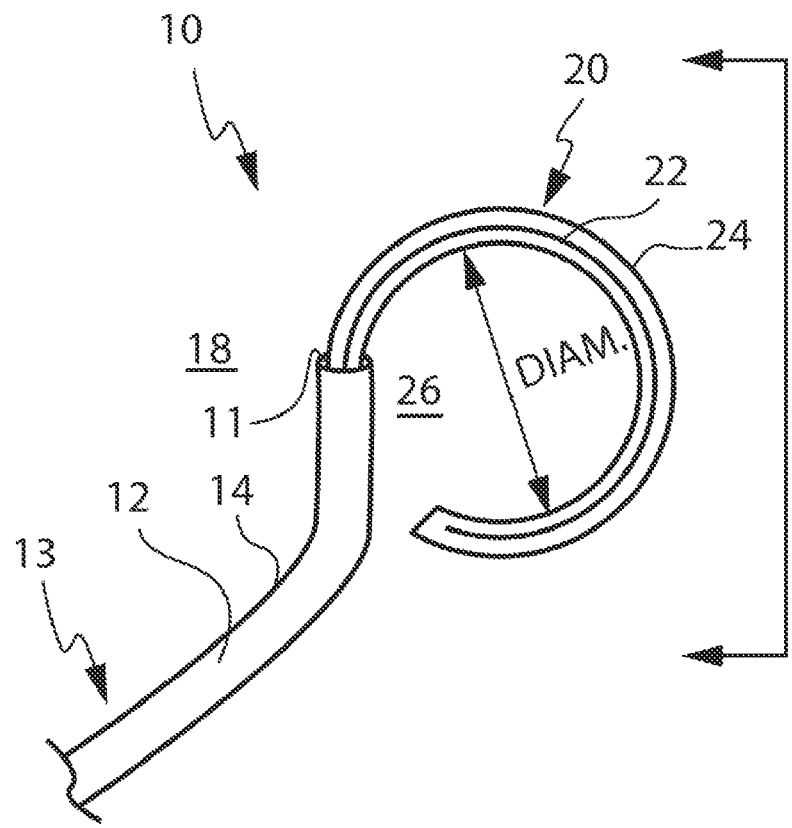
FIG. 1 is a perspective view of an ablation device in accordance with various aspects of the present invention.

This Specification discloses multiple systems, structures and devices, and associated methods, which employ various aspects of the invention. While these systems, structures and devices, and associated methods, are discussed primarily in terms of microwave based ablation systems used for ablating cardiac tissue, since such systems are well suited for use in the field of cardiac ablation, it should be appreciated that such disclosed systems are applicable for use in ablation systems employing differing modalities and methods associated with ablation procedures related to other bodily structures, as well. For example, the various aspects of the invention have application in procedures for ablating tissue in, or adjacent to, the brain, prostate, gall bladder, uterus, vasculature, intestine, stomach, liver, lung, skin, reproductive organs, or other organs or soft tissues of the body.

Notwithstanding where herein the terms are provided with alternative meanings, the following terms will have the following general meanings throughout the specification.

The terms "ablate" or "ablation," including all derivatives thereof, are herein intended to include the substantial altering of the mechanical, electrical, chemical, or other structural nature, property or biological function of tissue. In the context of cardiac ablation applications shown and described with reference to the variations of the illustrative devices described below, "ablation" is intended to include sufficient altering of the tissue to substantially block conduction of certain electrical signals related to cardiac arrhythmias from or through the ablated cardiac tissue.

The term "element" within the context of "ablation element" is herein intended to include a discrete element, such as an electrode or antenna, or a plurality of discrete elements, such as a plurality of spaced electrodes or an array of antennae, which are positioned so as to singularly or collectively ablate a region of tissue.

The terms "circumference" or "circumferential," including all derivatives thereof, are herein intended to include a continuous path or line that forms an outer border or perimeter that surrounds and thereby defines an enclosed region of space. Such a continuous path starts at one location along the outer border or perimeter, and translates along the outer border or perimeter until it is once again at the original starting location, enclosing the defined region of space.

In its simplest form, an ablation system, in accordance with the present invention, generally comprises an ablative energy source and an ablating device, which can be a surgical device or a catheter-based device. The ablative energy source is operably connected to the ablating device through a transmission line, whereby the ablating device directs or otherwise transmits, the received ablative energy toward a target tissue, creating an ablation therein. The ablating device includes an ablation portion which includes one or more ablating elements which are adapted to direct or transmit the ablative energy toward the target tissue.

Any of the ablating elements or ablating portions disclosed herein could have ablative sources including, but not limited to electrodes which transmit direct or alternating current, such as radiofrequency energy, in a bipolar or unipolar configuration; one or more antenna structures adapted to transmit electromagnetic energy, e.g. microwave energy, infrared energy; resistive heating elements adapted to transmit thermal energy derived from electrical current passing therethrough; optics, focused or non-focused, adapted to transmit photonic energy, including laser energy, in visible or non-visible form; elements for transmitting high energy particles such as ionized particles, electrons, X-ray photons, ultraviolet photons, and gamma photons; ultrasonic transducers including crystal structures which are adapted to transmit ultrasonic energy; tubular structures which are adapted to carry fluids which, through conduction, are able to heat or cool the target tissue to the point of necrosis; elements for cryoablation; tubular structures having one more openings to allow for the passage of ablative chemicals which can then contact and ablate the target tissue; and any other thermal energy which can be directed toward the target tissue, the energy sufficient to cause ablation of target tissue. The ablating portion can comprise any number of such elements, alone or in combination with other elements. The ablating elements or ablating portions disclosed herein may have a variety of suitable shapes. For example, various ablating elements or ablating portions disclosed herein may comprise microwave ablating antennas. Examples of antenna shapes that can be used for such microwave ablating antennas include, but are not limited to circular antenna, annular antenna, elliptical antenna, loop antenna, linear antenna, curvilinear antenna and planar antenna.

The various embodiments of the present invention are designed, or otherwise adapted, for the creation of continuous lesions through formation of specific area ablations, as part of a desired ablation pattern. The area ablations may be created by the geometric design, or configuration, of the ablation portion itself, or through the use of specific linear or curvilinear ablating portions and simple user inputs, such as simple rotational or linear movements for example. The use of such systems incorporating area ablators allows the user to create a desired lesion pattern more effectively and in much less than through the use of currently available technologies, as will become more readily apparent throughout the following discussion. A quicker and more effective procedure ultimately leads to reduced costs associated with various support equipment related to the procedure itself, while increasing procedural capacity.

For illustration purposes only, the ablating portion, comprising one or more ablation elements, may be formed into a two-dimensional geometrical shape, generally planar or otherwise formed to substantially engage the target tissue, the geometric shape is adapted to create a desirable area ablation upon a target tissue surface, the created area ablation may or may not correspond to the geometric shape of the ablating portion. Alternatively, the ablating portion may be a linear or curvilinear element which can be rotated about a specific point of reference or moved along a defined ablation line with respect to the tissue along the ablation portion, in a direction other than along its longitudinal axis for example, to create the desired area ablation. The specific point of reference can be part of the ablation system itself, an anchoring member or needle for example, or can be an anatomic structure or location within the body, an inner wall surface of the pulmonary vein PV or the left atrial appendage LAA for example. Still, the ablation element may be adapted to ablate a volumetric area within a target tissue, the volumetric area ablation may or may not be continuous with a tissue surface.

It is important to note, while certain geometric shapes can create area ablations, such area ablations may or may not be identical to or directly follow from the geometric shape of the ablating device itself. To illustrate this concept, consider an ablating device which includes two linear spline sections which intersect at their midpoints, the splines forming an "X" shape for example, with each spline section including two or more ablating elements, in the form of electrodes, along its length. Depending upon the ablation parameters utilized, such parameters including, but not limited to, ablating element arrangement, applied power and associated ablation time for example, differing results can be achieved.

If the spline electrodes are arranged such that the spline electrodes are activated along each individual spline in a bipolar fashion, or all the electrodes along the individual spline are activated with respect to a common ground electrode located elsewhere, a surface lesion will be formed generally corresponding to the linear shape of the spline, a linear line for example, resulting in an overall final area ablation more similar to the geometric shape of the ablating portion of the device, an "X" shape for this example.

Alternatively, if the corresponding electrodes of each spline are activated with respect to each other, from one spline to another through bipolar or unipolar activation, the resulting ablation will include a surface lesion having dimensions generally corresponding to the overall dimensions of the outer perimeter or periphery of the ablating element geometric shape, e.g. being able to be defined by a length and a width, or diameter, corresponding to the overall geometric shape. Therefore, the "X" shaped ablating portion of the ablation device can create ablations similar to its geometric "X" shape, or ablations similar to its overall geometric shape, a rectangular shape having a length and width, or a generally circular ablation having a specific diameter for example.

Thus, in any of the embodiments disclosed herein, area ablations can be created by ablating target tissue corresponding to the perimeter or periphery of the geometric shape of the ablating portion, or corresponding to the overall general geometric shape of the ablating portion. An annular shaped ablating portion can therefore create partial or complete circular region lesions, depending on the placement or configuration of the ablating elements themselves. The area within the circular region can remain untouched or can be ablated depending on the configuration of the one or more ablating elements, the activation of such elements and the ablative power applied, as well as the time period such ablative power is applied. Moreover, the ablating portion can be sized to allow for thermal conduction which will also act to fill the interior portion of the geometric shape. The various geometric shapes can be designed having predetermined dimensions which, along with other ablative procedural outcomes, due to conductive heating for example, act to fill out and create a desired area ablation.

While the area ablations are generally described in terms of their surface, it is important to note that with adjustment of the various ablation parameters, such as applied ablative power and time of power application, area ablations or volumetric ablations having significant depths can be achieved. This is important where you want to ensure a predefined surface ablation is created, while also ensuring the corresponding lesion depth is controlled such that undesirable damage to tissues adjacent the target tissue, or a tissue surface opposed to the target tissue, does not occur, while a lesion of any desired depth, a transmural lesion through the thickness of the left atrial wall for example, is created. Additionally, the various ablating portions described herein can include cooling systems adapted to cool tissue surfaces to prevent undesirable damage to such surfaces, as part of the creation of a lesion therein. Alternatively, the cooling systems can be used to create volumetric ablations within the target tissue itself at a desired tissue depth, keeping the temperature of the tissue surface below the level at which tissue ablation occurs. It is important to note that a tissue surface includes naturally occurring surfaces as well as surfaces created during a procedure. For example, advancement of a needle-shaped ablating portion within a tissue creates new tissue surfaces with which a cooling system can engage.

The ablating devices disclosed herein can incorporate an ablating portion which is adapted to be placed on opposing sides of a target tissue; on opposing target tissue surfaces, or within tissue, the target tissue within or between the ablating portion. For example, the distal portion of an ablating device may include jaw members, each comprising one or more ablating elements, which can be placed on opposing tissue surfaces, for example epicardial and endocardial surfaces, opposing septal wall surfaces, opposing surfaces between the inferior vena cava and right atrium or opposing atrial wall surfaces. The various ablating devices adapted to engage the tissue and providing for placement of the ablating portion on opposing sides of the target tissue.

Alternatively, two different ablating devices, each having area ablating portions can be placed on opposing sides of a target tissue. For example, a first ablating device can be positioned within the left atrium, the ablating portion engaging the endocardial surface of the left atrial wall, while the ablating portion of a second ablating device can be positioned on the epicardial surface of the left atrial wall opposite to the ablating portion of the first ablating device. The systems can incorporate cooling systems as discussed above to create a volumetric area ablation within the tissue structure itself, to aid in the treatment of ventricular tachycardia for example.

In accordance with the present invention, various ablation devices are described which include ablating portions having specific geometric shapes, allowing for the creation of specific area ablations. Numerous area ablations can be created through simple movements of the ablating portion allowing for the creation of continuous lesions in a target tissue, as part of a desired lesion pattern. The ablating portion is also sized to encourage substantial contact with the target tissue surface and the easy creation of continuous lesions with minimal coarse movements, resulting in a faster ablation procedure requiring less precision. Additionally, due to the nature of the ablating devices, any desirable lesion set can be created through methods described herein. Also, some geometric shapes are adapted to comprise three-dimensional structures which, from one perspective, define a first desirable geometric shape, while from other perspectives, define additional desirable geometric shapes. Such systems allow for the creation of area ablations from two-dimensional geometric shapes, and linear or connecting ablations used to connect the various surface area ablations, creating a continuous lesion for example.

Such area ablating systems as described herein have tremendous advantages over other systems employing curvilinear or point ablating portions. Curvilinear portions, while adapted to more readily conform to the curved surface of the target tissue, still require a high level of precision to create suitable continuous lesions.

Point ablating portions require numerous point ablations for the creation of a continuous lesion as part of a desired lesion pattern. Turning briefly to FIG. 6A which depicts a sectional view of the heart 80 and an ablation line AL as part of a desired lesion pattern. As depicted, various point ablations identified as points PA are required to ablate a small section along the desired ablation line AL. While shown as creating a continuous lesion, it is often very difficult for the user to properly place the point ablating portion within a beating heart, against the target tissue surface, and be able to create slightly overlapping lesions as shown. The systems and methods discussed herein allow for the creation of large area ablations in comparison, such as the area ablation defined by circle identified as A1 of FIG. 6A, resulting in more effective procedures requiring less time to complete.

Figure 16:
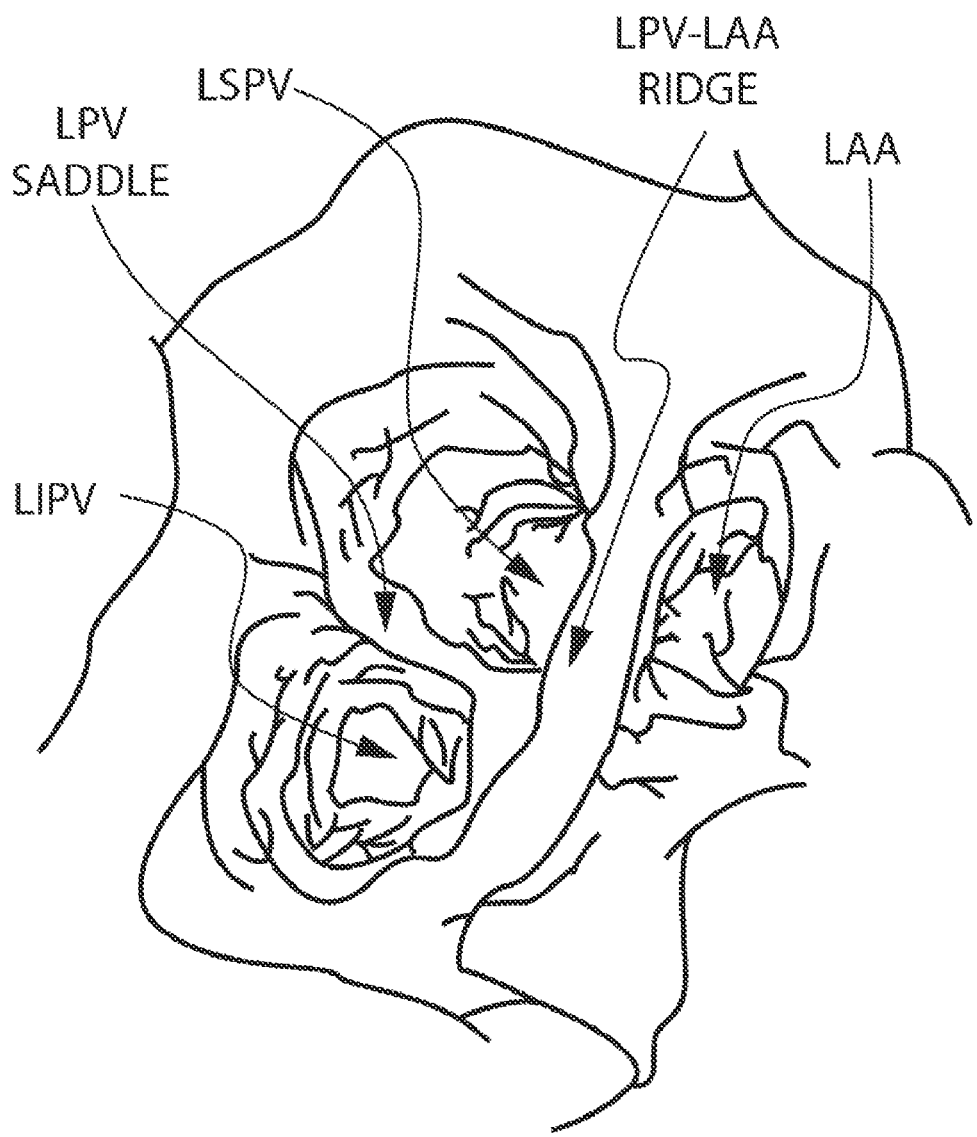
FIG. 16 depicts the left lateral anatomic structures of the left atrium.

Point ablating portions, while requiring the creation of numerous lesions leading to increased procedural time and associated costs, are very difficult to properly place upon certain anatomic structures to ensure effective creation of a desired continuous lesion. With reference momentarily to FIG. 16 which depicts the left lateral view of the inner wall of the left atrium, one can see the left superior and inferior pulmonary veins, LSPV and LIPV respectively. Additionally, the left atrial appendage LAA is shown separated from the left pulmonary veins by a tissue ridge identified by the LPV-LAA ridge. The LPV-LAA ridge is on the order of a few millimeters wide. Placement of an area ablation portion about the ridge is very difficult, as should be obvious from the depiction of FIG. 16. The systems of the present invention address these issues.

In other embodiments, the ablating device may include a flexible joint as part of a self-aligning tip portion. The flexible joint allows the ablating portion to substantially contact the target tissue surface irregardless of the approach angle with respect to the target tissue surface. The self-aligning functionality of the flexible joint can be initiated through linear translation or advancement of the ablating device toward the target tissue. Upon contact with the target tissue, the self-aligning portion deflects the ablating device into the preferred orientation upon the target tissue surface.

Ablating devices described herein may also include a centralized delivery point which more equally distributes tissue contact forces about the ablating portion in contact with the target tissue reducing the likelihood of tissue perforation, while ensuring proper tissue contact for achieving the desired ablation. Of course, the target tissue contact requirements for ablation procedures vary depending on the modality used. For example, ablation systems which transmit or use electromagnetic energy do not require the ablating element to be in direct contact with the target tissue. Rather, the electromagnetic energy can penetrate the target tissue from a location a distance adjacent thereto. The location can range from substantially in contact with the target tissue to a distance between the ablating element and target tissue.

While the various embodiments disclosed herein are generally directed to ablating structures which are placed in contact with or adjacent a target tissue surface, area ablating portions which are placed above, or otherwise a distance away from, the target tissue surface are also contemplated. For example, an ablating portion may comprise one or more ablating elements adapted to be positioned away from the target tissue, the one or more ablating elements further adapted to transmit electromagnetic energy from the element to a target tissue. While the energy can be microwave energy transmitted from an antenna structure, the electromagnetic energy can be at additional frequencies. For example, an ablating portion may be a lens portion which is adapted to deliver electromagnetic energy in the form of ablative photonic energy, in the visible or non-visible range, to the target tissue. As with other variations of ablating portions discussed herein, the lens portion itself can be adapted to create an area ablation through its configuration or geometric shape. A lens portion, as with other ablating portions, may be similar to the desired geometric shape of the area ablation, or can be adapted to simply produce the desired geometric pattern. More specifically, the lens portion can be adapted to create a curvilinear geometric pattern upon the target tissue, however the geometric structure of the lens itself may differ, not having the same geometric shape or pattern. Alternatively, the lens can be moved or rotated about a know point of reference to create an area ablation. The lens ablating portion can be placed within a hollow structure, as part of the ablation device, to displace blood between the ablating portion and the target tissue. As with other embodiments, multiple area ablations can be created from which continuous lesions, as part of a desired lesion pattern, can be formed.

While the various embodiments disclosed herein are discussed primarily in terms of ablating cardiac tissue related to cardiac arrhythmias. More specifically, in the treatment of atrial fibrillation, target tissue is defined through the desire to create a desired lesion pattern within the atrial tissue whereby the atrial tissue is isolated from the origin of errant signals which are related to the onset of atrial fibrillation, such errant signals originating for example from one or more locations along one or more pulmonary veins. However, other tissue locations corresponding to other suspect errant signals which lead to atrial fibrillation are also contemplated. For example, the methods and devices herein can be used to determine the location of, and eventually the ablation of, certain tissue of the nervous system of the heart, ganglionated plexi, which are believed to be related to inducing and sustaining atrial fibrillation. These ganglia are located at specific locations or regions under epicardial fat pads. Such locations are often not close to the pulmonary veins themselves. It has been found that high frequency stimulation at these locations consistently results in the inducement of atrial fibrillation. Ablation at these sites renders the sites unresponsive to such stimulation. These sites can be ablated, using methods and devices discussed herein, from either an epicardial approach or an endocardial approach, or a combination of epicardial and endocardial approaches.

Associated steering systems described herein provide for directing the ablating device toward and into contact with the target tissue. Various steering systems may include structures which allow for deflections in more than one plane allowing for the production of complex lesions without the need for complex steering.

In accordance with the present invention, various methods are also described herein which allow for the creation of continuous tissue lesions using ablating devices adapted to create area ablations, as part of a desired lesion pattern, through minimal or coarse manipulation of the ablation device. The device manipulation is achieved through, for example, linear, curvilinear or rotational movements, or a combination of such movements. The inventive methods allow for the simple and effective creation of the desired lesion patterns without the precision required with regard to current ablation systems. Moreover, as discussed above, the ablating devices are adapted to include ablating portions which encourage the creation of such lesion patterns more easily, requiring less procedural time and procedural support, ultimately resulting in more cost effective procedures.

With reference to FIGS. 1 and 2, a first embodiment in accordance with the present invention will be discussed. FIG. 1 depicts ablation system 10 as generally including a guide sheath 12 and a transmission medium or transmission line 13 ending in an ablating portion 20. Guide sheath 12 includes a flexible outer tube 14 and an inner lumen 11 which passes therethrough. The transmission line 13 and ablating portion 20 slidably positioned within the lumen 11 of outer tube 14, the arrow of identifier 13 indicating or referencing the transmission line 13 passing within the tube 14. The flexible outer tube 14 may be made of any suitable material such as medical grade polyolefins, fluoropolymers, or polyvinylidene fluoride. For illustration purposes only, PEBAX® resins from Autochem of Germany can be used. Ablating portion 20 further includes an ablating element 22. Ablating element 22 is adapted to transmit an ablative energy. Examples of ablative energies that can be used in the present invention include, but are not limited to RF energy, microwave energy, ultrasound energy, thermal energy, cryogenic energy and infrared energy. In an alternate embodiment, ablating element 22 is adapted to transmit high energy particles. Examples of such high energy particles include, but are not limited to ionized particles, electrons, X-ray photons, ultraviolet photons, and gamma photons. In an alternate embodiment, ablating element 22 is adapted to release an ablative chemical. In the particular embodiment disclosed in FIGS. 1 and 2, ablating portion 20 has a single ablating element 22. Ablating element 22 is a microwave antenna encased within a dielectric material, flexible polytetafluoroethylene (PTFE), often referred to by its trademark TEFLON®, or expanded PTFE (ePTFE) for example.

Figure 2A:
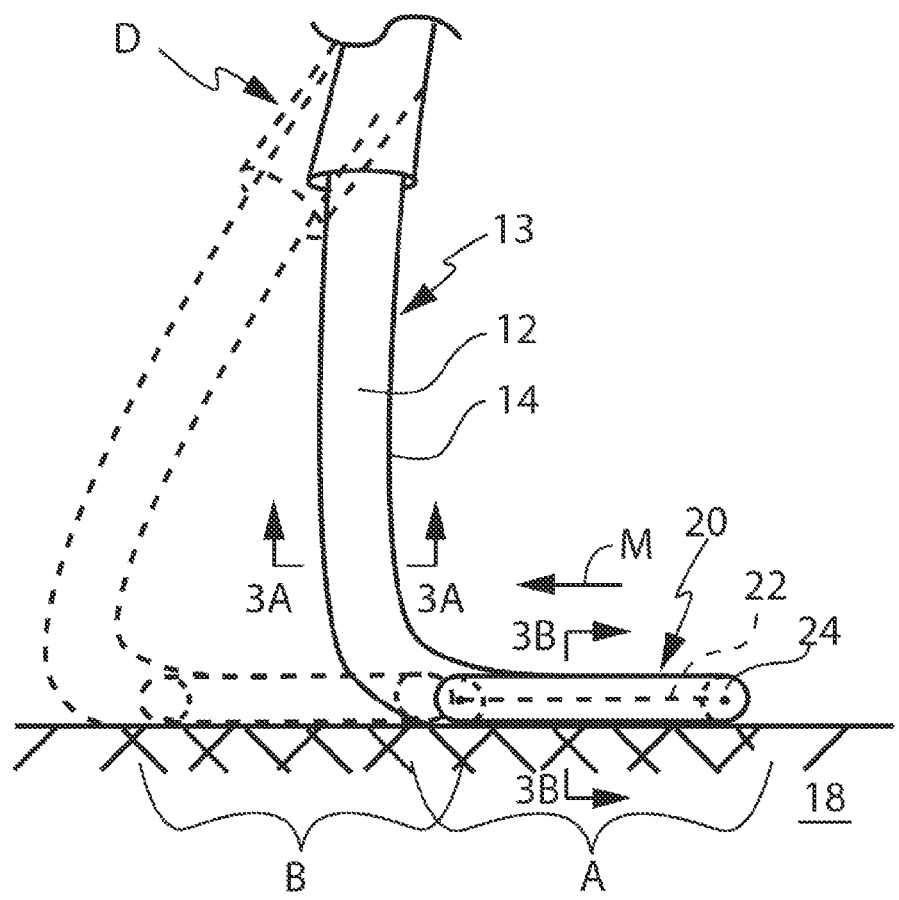
FIG. 2A is a side elevational view of the ablation device of FIG. 1.

As shown, with specific reference to FIG. 2A, guide sheath 12 is adapted to initially approach the target tissue 18 substantially normal to the tissue surface itself, shown in a deflected orientation engaging the tissue surface with the lateral outer wall 14 of the distal portion of sheath 12. It is important to note that other approach angles and corresponding degrees of deflection are also contemplated and that the depicted orientation is for illustration purposes only. Moreover, the deflection functionality can be solely provided by the ablation portion itself when advantageous, for example when guide sheath 12 includes a steering system to steer or direct its distal end.

The deflection of sheath 12 can be achieved through any suitable means. For example, sheath 12 can include a steering system, including one or more pull wires, which is adapted to form the desired deflection required to position the distal opening generally normal to the target tissue surface adjacent thereto. Alternatively, shape retaining materials can be used. For example, the distal portion of the guide sheath 12 can be formed from shape retaining materials, tubular structures made from polyethylene or including superelastic metal such as Nitinol for example, and interfaced to the elongate member of the guide sheath 12 via a flexible portion or flexible joint, as discussed later herein. In any case, the ablation sheath 12 can be composed of any suitable flexible biocompatible material, such as PU Pellethane, TEFLON® or polyethylene, which, as stated immediately above, is capable of shape retention once external forces acting upon the sheath 12 are removed, for example when the ablation sheath 12 exits the distal opening of a less flexible tubular member.

It is important to note, while currently discussed in terms of positioning the distal opening of sheath 12 generally perpendicular to the target tissue surface, additional placements adjacent to or removed from the target tissue surface are also contemplated such as normal to the target tissue, as discussed in more detail below.

Transmission line 13 can be a suitable flexible coaxial cable of the desired size, having an outer conductor and an inner conductor separated by a dielectric material enclosed in an outer jacket. The outer jacket or dielectric material can be any suitable biocompatible material, such at PTFE. For illustration purposes only, the outer jacket may be constructed from solid, but flexible, PTFE, while the dielectric material may be constructed from expanded PTFE which is advantageous due to its increased flexibility and radial stability.

The inner conductor of the transmission line 13 can be electrically coupled directly or indirectly to the antenna 22 of ablation portion 20 through any suitable means such as soldering, brazing, ultrasonic welding or adhesive bonding. In other embodiments, antenna 22 of ablation portion 20 can be formed from the inner conductor of transmission line 13 itself, the outer conductor and none, part, or all of the dielectric material surrounding the center conductor being removed, as desired. This is typically more difficult from a manufacturing standpoint but has the advantage of forming a more rugged connection between the antenna and the inner conductor. In other embodiments, it may be desirable to indirectly couple the antenna to the inner conductor through a passive component, such as a capacitor, an inductor or a stub tuner for example, in order to better adapt the antenna system for ablation of the specific biological target tissue.

The antenna 22 of ablation portion 20 includes an electrically conductive material from which the electromagnetic energy is transmitted. For illustration purposes only, copper or silver-plated metal are well suited for transmission of such electromagnetic energy. While antenna 22 may be formed from a solid, but flexible, piece of electrically conductive material, antenna 22 may be formed from other suitable materials, polymers or other plastics or resins for example, the electrically conductive material being deposited at one or more locations along the length of structure, each location being electrically connected to the center conductor of transmission line 13. Additionally, the antenna portion can be a braided structure, the braided structure adapted to provide increased flexibility while preventing substantial signal loss.

The antenna 22 diameter can be any suitable size which allows for the transport of the ablation portion 20 to the target tissue site and transmission of electromagnetic energy thereto. Such diameters include the range from about 0.2 mm to about 0.6 mm, but can be larger in diameter if desired. The dielectric 24 holds the antenna 22 a known distance away from the target tissue, a distance ranging from about 0.2 mm to about 4 mm. For operating frequencies disclosed herein, antenna 22 can be of any suitable length. For illustration purposes only, for an operating frequency of approximately 2.45 GHz the antenna 22 can be from about 12 mm to about 20 mm in length. Given other operating frequencies, longer lengths can be achieved.

Figures 3A, 3B:
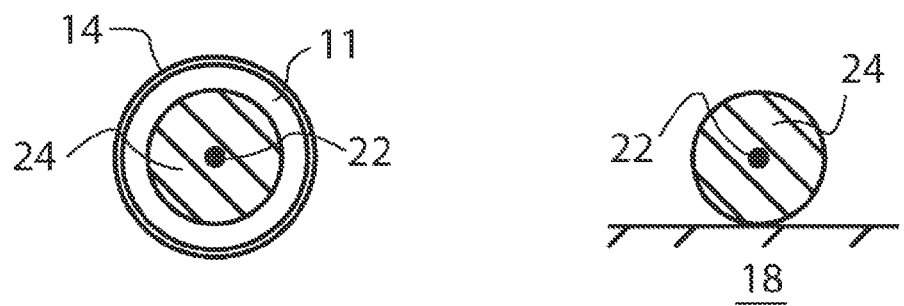
FIGS. 3A and 3B are crossectional views of the ablation device of FIG. 1.

As shown in FIGS. 3A and 3B, the antenna 22 is encased within the dielectric 24. While shown coaxial with the outer surface of the dielectric 24 material, antenna 22 may be positioned offset with respect to the longitudinal axis of the dielectric 24, closer to the target tissue surface for example. Alternatively, the dielectric may have a non-circular crosssectional surface, the antenna located inline or offset with respect to the crossectional geometric center. The insulating dielectric 24 material is preferably a low-loss dielectric material which is relatively unaffected by microwave exposure, and thus capable of transmitting the electromagnetic energy therethrough. Moreover, the dielectric preferably has a low water absorption component such that it does not react by thermally heating due to direct exposure to the electromagnetic energy. With this in mind, the dielectric 24 may be formed from any suitable biocompatible materials, including, but not limited to, moldable PTFE or ePTFE, silicone, or polyethylene, polyimide, or other suitable material having similar qualities. The dielectric material, PTFE for example, provides a surface which is less likely to adhere to biological tissue during application of ablative electromagnetic energy.

The ablating portion 20 may further include a directive or isolating component (not shown) which is positioned opposite from the target tissue contact side, the antenna positioned between the isolating component and the target tissue. Such a component may be used to direct a majority of the electromagnetic energy toward the target tissue, prevent a substantial amount of electromagnetic energy from reaching adjacent tissues opposite the ablation portion 20 from the target tissue which may result in undesirable tissue damage, or both. The directive component may or may not be electrically connected to the outer conductor of transmission line 13.

The ablating portion 20 is adapted to be deliverable via the inner lumen 11 of the guide sheath 12. More specifically, the guide sheath 12 has a greater stiffness than ablating portion 20, thus the distal portion of guide sheath 12 generally maintains its shape and configuration adjacent the target tissue as the ablating portion 20 is advanced therethrough. As depicted, ablating portion 20 is preshaped to take on a specific geometric shape as the ablating portion is advanced from the exit port of the guide sheath 12, until the ablating portion 20 takes on its final shape, a circular or annular shape as shown in FIG. 1 for example. As is discussed in greater detail below, the ablating portion 20 can be advanced only partially exiting the distal opening of lumen 11, the desired geometric shape being a curvilinear arch. Under certain circumstances, such a configuration is very advantageous. For example, since blood and heart tissue have similar water concentrations, whether the antenna 22 is fully or only partially extended, the antenna 22 system will remain balanced and well adapted, provided that the overall antenna length remains constant. The design of ablating portion 20 of FIG. 1 can be used to design any of the ablating portions disclosed herein. For example, the design of ablating portion 20 of FIG. 1 can be used to design ablating portion 268 disclosed later in this specification.

The ablating portion 20 may include internal structures such as Nitinol or outer sheath structures made from shape retention materials, as discussed herein, to provide for the specific geometric shape which ablating portion 20 assumes once it exits the distal opening of lumen 11. Alternatively, considering the preferable microwave based ablation system, the antenna portion itself may be composed of such shape retaining materials, the antenna structure being metallically covered or coated as necessary to enable electrical transmission of the electromagnetic energy toward the target tissue.

When fully advanced the circular orientation of the ablating portion 20 preferably has a diameter, indicated by arrow D of FIG. 1, ranging from about 4 mm to about 20 mm. It is important to note, while discussed in terms of two separate structures, the guide sheath 12 and ablating portion 20 can be constructed as one unit. For example, the guide sheath 12 can be bonded to the ablating portion 20, the combined unit then being advanced through a separate sheath, taking on its specifically designed geometric shape upon exiting the sheath.

The energy source (not shown) includes a microwave generator which may take any conventional form. Since biological tissue has such a high water content, when using microwave energy for tissue ablation, the optimal frequencies are generally those which are optimal for heating water. For illustration purposes only, frequencies in the range of approximately 800 MHz to 6 GHz work well. More commonly, frequencies of 915 MHz and 2.45 GHz are used. A conventional magnetron of the type commonly used in microwave ovens can be utilized as the energy source of the microwave generator. It should be appreciated, however, any other suitable microwave power source could be substituted in its place, and the disclosed concepts may be applied at other frequencies, such as 434 MHz or 5.8 GHz (ISM band) for example.

In operation, with specific reference to FIG. 2A, the guide sheath 12 is advanced toward the target tissue until the lateral outer wall 14 of the distal portion engages the target tissue 18 site. The ablating portion 20 is then advanced out the exit opening of lumen II and takes on its specific geometric shape, a circular geometric shape for example as shown. A first ablation procedure is then performed by supplying microwave energy to the antenna portion, which in turn radiates the energy, in part, toward the target tissue 18, creating a lesion therein.

After a first ablation lesion corresponding to location A in FIG. 2A is created, successive ablations can be created, as part of a desired lesion pattern, through simple movements of the guide sheath 12. For example, as depicted in FIG. 2A, the guide sheath 12 can be deflected or rotated a controlled or known amount in the direction of arrow M whereby the new position of the ablating portion 20 generally corresponds to location B of FIG. 2A. As stated above, the distal portion of sheath 12 is flexible, taking on a more acute angle with respect to the target tissue 18 when the ablating portion is moved to location B from the same access or delivery point D as shown, allowing the ablating portion 20 to maintain substantial contact with the target tissue at location B.

As depicted in FIG. 2B, as the ablating portion 20 is further moved along an ablation path in the direction or arrow M, successive continuous lesions at locations A, B and C are created. As shown, despite the fact the guide sheath 12 was simply rotated, such rotation will not necessarily result in the placement and creation of successive continuous lesions in a strict linear or straight line fashion. Rather, due to blood flow, cardiac activity or a patient's specific anatomy, the ablating portion 20 may be directed along a nonlinear path. By understanding the relationship between the angular deflection of the guide sheath 12 and the distance between the deflection point (not shown) and the ablating portion 20, the user can ensure that movement of the ablating portion in the direction M will be less than the geometric dimension of the ablating element along that line. Thus, while the ablating portion 20 may move slightly in the lateral direction along the desired ablation path and with respect to the previous ablation location, the successive ablation will still be continuous with the previous ablation.

Moreover, as depicted in FIG. 2A, certain geometric shapes, for example circular or annular shapes, in addition to providing the user more freedom of motion during an ablation procedure, also provide an extra barrier or conduction blocking ablation line, to better ensure the creation of the desired conduction block. More specifically, as shown, the second ablation which is labeled B crosses or otherwise intersects the first ablation, labeled A, at least at two points, thus providing at least two barriers which act to prevent undesirable electrical signals from passing through the ablated tissue to the remaining isolated atrial tissue. It should be apparent that if the lesion B were a surface area lesion, instead of a perimeter circular lesion as depicted, then lesion B would intersect lesion A at least at two points, and arguably at numerous points. In this way a continuous lesion can be easily created by ablation systems having ablative portions adapted to assume specific geometric shapes, the geometric shapes designed to provide the user more freedom of motion and control.

While the embodiment of FIG. 1 has been depicted and described as including a guide sheath 12 having a distal curvilinear section from which the ablation device 20 is advanced, other configurations incorporating additional steering elements are contemplated, as discussed in greater detail below. Additionally, the geometric planar shape which the ablating device forms, while shown generally normal with the longitudinal axis of the main section of the sheath 12, may be adapted to form any desirable angle therebetween from about 0° to about 90°, as generally stated above. The ablating device may include deflection or steering elements which can be operated to further deflect the ablating element into various additional orientations to engage a desired target tissue surface from a specific known point with respect to the tissue. It should be apparent that such deflectable elements may be able to create area ablations while in a first configuration, and linear ablations while in another configuration, depending on the specific orientation of the ablating element. Such systems may include additional configurations corresponding to multiple area and/or linear or curvilinear ablations. The ablation devices or ablating elements disclosed herein may also comprise one or more mechanisms such as pull wires to change at least one physical dimension such as the diameter of the ablation devices or ablating elements.

The FIG. 1 embodiment may be directed or otherwise steered toward the target tissue using any suitable guiding system, such as the various steering systems currently available. Alternatively, the steering systems may utilize one or more steering wires operably attached to a handle portion allowing the user to remotely manipulate or steer a distal portion which then guides the ablating device which translates therein.

With reference now to FIGS. 4A-4E, one steering embodiment used to guide the ablating portion toward target tissue, in accordance with the present invention, will be described in more detail. The steering system of FIG. 4 includes a delivery sheath 16 and a guide sheath 12, guide sheath 12 of FIG. 4 being similar to the guide sheath 12 of FIG. 1 in that it is adapted to have a curved distal portion along a single plane parallel to the longitudinal axis of the guide sheath 12. Moreover, it is important to note that the differing ablation systems, as discussed herein, can include steering systems comprising additional sheaths similar to sheath 12 to provide for more complex curves.

Delivery sheath 16 is configured to be relatively rigid such that the distal end of sheath 16 can define a working point within a hollow structure, such as a chamber of the heart, from which an ablating device can be placed, advanced and positioned at a desired location upon the target tissue surface. As will become clear, once the starting point is established, the user can easily manipulate the ablating device relative the delivery sheath and create a desired lesion set.

The delivery sheath 16 may be a rigid tubular member as part of a surgical tool designed to operably attach to a handle portion from which the user, a cardiac surgeon for example, can directly manipulate or otherwise direct the distal portion of sheath 16 as he sees fit to serve a particular ablation procedure. Alternatively, delivery sheath 16 may be a semi-rigid tubular member forming the distal portion of a long tubular catheter member adapted to be guided to the heart via the vasculature. In this second catheter embodiment, the rigid section of sheath 16 may be of any suitable length, cooperating with anatomical support structures within the heart, the septal wall for example, to provide the necessary stability to help maintain the distal position of sheath 16 at a relatively known position with respect to the heart.

Delivery sheath 16 includes a lumen which passes therethrough and wherein the guide sheath 12 translates. As shown more specifically in FIG. 4B, the distal curvilinear section preferably has a radius of curvature R suitable for translation of the ablating portion therethrough. While shown to have a generally constant radius of curvature along the distal portion of sheath 12, it should be apparent that the radius of curvature along the distal portion may be non-linear along its length. For example, the distal portion of the curvilinear section may have a first radius of curvature while a more proximal portion of the curvilinear section may have a second radius of curvature. In this way, various guide sheaths can be adapted to have differing curved distal portions which are designed for ablation procedures of specific biological tissues of the body. Moreover, the distal tip of guide sheath 12 may be formed into an angled sharp point, similar to a hypodermic needle, for translating through biological tissue toward a target tissue.

Figures 4A, 4B, 4C, 4D:
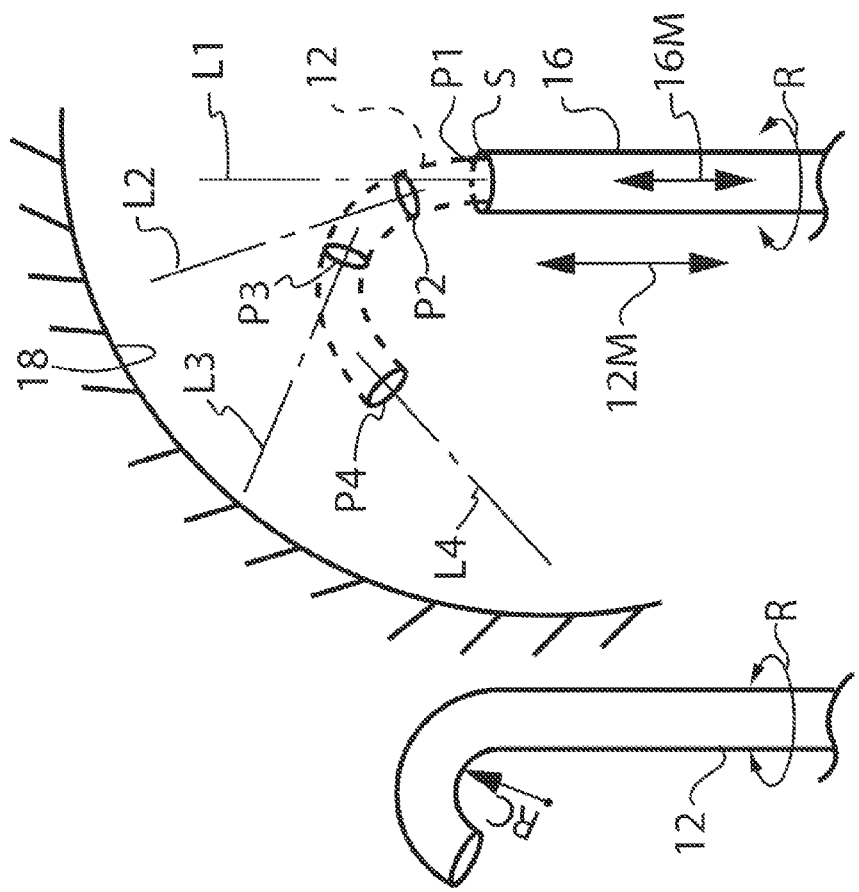
FIG. 4A is an elevational view of an exemplary delivery sheath, as part of a steering system, used in accordance with the present invention.
FIG. 4B is an elevational perspective view of an exemplary guide sheath, as part of a steering system, used in accordance with the present invention.
FIG. 4C is a perspective view depicting the delivery sheath of FIG. 4A and the guide sheath of FIG. 4B cooperating in accordance with various aspects of the present invention.
FIG. 4D is another perspective view depicting the delivery sheath of FIG. 4A and the guide sheath of FIG. 4B cooperating in accordance with various aspects of the present invention.

The delivery sheath 16 and guide sheath 12 are designed to cooperate to allow an ablation device to translate through the sheath system and be directed to a specific spot or target tissue 18 location. With reference specifically to FIGS. 4C and 4D, the cooperation of the sheath system at four different guide sheath 12 distal end positions, shown in dashed, is depicted.

As shown, at the first position Pi the longitudinal axis line, represented by L1 is substantially the same as the longitudinal axis of delivery sheath 16. From this point, it should be apparent that as an ablation device is advanced out the distal opening of guide sheath 12 it will generally engage the target tissue at the point where longitudinal axis line L1 intercepts the target tissue 18, assuming the ablating device is designed to be directed in a single general direction from the distal opening of the guide sheath, as better depicted in FIG. 4E. Ablating devices including curvilinear shaft structures which are adapted to cooperate with the steering system of FIG. 4 to reach specific areas are also contemplated.

As the guide sheath 12 is further advanced along arrow 12M, the distal portion of the guide sheath 12 starts to arch into its predetermined orientation. As guide sheath 12 is advanced toward a second position, P2, the longitudinal axis of the distal opening of guide sheath 12 becomes redirected along longitudinal axis line L2. As with the first position P1, an ablating device which is advanced out the distal opening of the guide sheath 12 would then generally engage the target tissue 18 at the point where the line L2 intercepts the tissue 18. In accordance with positions P1 and P2, it should be readily understood that as the guide sheath 12 is further advanced out the distal opening of the delivery sheath, the distal opening of the guide sheath 12 is redirected toward a different target tissue location. Two additional positions P3 and P4, are also defined, along with corresponding longitudinal axis lines L3 and L4, respectively. With specific reference to FIG. 4E, an ablation device is shown exiting the distal end of the guide sheath 12 and engaging the target tissue 18 at a point generally consistent with the longitudinal axis at the distal opening of sheath 12, which has been deflected to a position similar to P3 of FIGS. 4C and 4D.

While four positions have been shown, it should be apparent that the steering system of FIG. 4 can direct the distal opening of the guide sheath 12 at numerous different positions along the plane of curvature. The guide sheath 12 can then be rotated a predetermined amount along its longitudinal axis as indicated by arrow R, and additional lesions can be created along the deflection plane. In a similar fashion, instead of translating the guide sheath 12 to a new position, the guide sheath 12 can be rotated a predetermined amount to a new radial position at which a new lesion can be created, which can be continuous with the first, if desired. Additionally, the delivery sheath 16 can be translated as well to define or redefine the initial starting point S of deflection. In this way, the guide sheath, and ultimately the ablating portion of an ablation device, can be directed to any desired location along a target tissue surface from within a hollow organ, the posterior wall of the left atrium for example.

With specific reference now to FIG. 4E, for illustration purposes only, the steering system is shown in cooperative operation with an ablation device embodiment similar to that of FIG. 1, where the guide sheath and ablating portion are one operative unit. As shown, the delivery sheath 16 is first positioned with respect to the desired target tissue 18, the posterior wall of the left atrium for example. The guide sheath 12 is then advanced through the distal end of the delivery sheath 16 until the distal opening of the guide sheath 12 is directed toward the desired location of the target tissue 18, the distal opening of the guide sheath 12 defining a longitudinal axis line L3. The ablating portion 20 is then deployed into its specific geometric shape and advanced toward the target tissue 18 until it makes contact therewith. As the ablating device exists the distal opening of the guide sheath 12 it takes on its predefined annular shape. Continued advancement then acts to move the ablating portion toward the target tissue.

As discussed in more detail above, the ablating portion 20 can take on its desired geometric shape through any suitable method. For example, the ablating element can use a preshaped material which allows the ablating element to take on its desired geometric shape once it exits the distal opening of the guide sheath 12. The preshaped material can be in the form of Nitinol wire, or other suitable shape retaining metal or plastic. Additionally, the dielectric portion, portion 24 of FIG. 3B for example, can be formed from a shape memory material which takes on the desired geometric shape once it exits the distal opening of the guide sheath 12. It should be apparent that such ablation systems incorporating these type of preshaped materials must include guiding sheaths, guide sheath 12 and delivery sheath 16 for example, which are less flexible such that they do not substantially deform while the ablating element, or ablating portion, passes therethrough. Alternatively, the preshaped material can be adapted to take on its shape once it reaches a specific temperature, the temperature of the surrounding blood for example. Once warmed by the blood the ablating element can then take on the desired geometric shape.

Once a first lesion is created, corresponding to the current position of ablating portion 20, the ablating portion 20 is then retracted until it no longer is in substantial contact with the target tissue 18. The guide sheath 12 is then either rotated along its main longitudinal axis or translated within delivery sheath 16 in order to define a new target tissue 18 position. More specifically, with the ablating portion 20 retracted, the guide sheath 12 can be rotated, as shown by arrow R, to another radial position with respect to the longitudinal axis of guide sheath 12. At this point, the ablating portion 20 can then be advanced to engage the target tissue 18 at another desired location, and another lesion can be created therein, the additional lesion being continuous with the first if desired. Alternatively, with the ablating portion 20 retracted, the guide sheath 12 can be advanced or retracted to form a new distal longitudinal axis line. The ablating portion 20 is then advanced to engage the target tissue 18 at the subsequent location and the additional lesion is formed, continuous with the first if desired.

While the steering embodiment of FIG. 4 is generally discussed with respect to having the guide sheath 12 translating within and with respect to the delivery sheath 16, it should be readily apparent that the delivery sheath 16 can be translated over and with respect to the guide sheath 12 to form or define the direction of the distal opening of guide sheath 12. Furthermore, the guide sheath 12 can be translatable over delivery sheath 16 as well, the delivery sheath 16 being a more rigid structure such that it functions to conform the guide sheath 12 to the shape of the delivery sheath 16 while translating over delivery sheath 16. As the distal end of sheath 12 passes over the distal end of delivery sheath 16, the distal portion of guide sheath 12 takes on its preformed shape, as discussed in greater detail above.

With reference to FIG. 5, another steering system which can be used as part of an ablation system in accordance with the present invention will be discussed in greater detail. The steering system of FIG. 5 allows for accurate placement of an ablation device adjacent target tissue. As shown, the steering system comprises a flexible or bendable sheath having at least one working lumen therethrough and at least one steering lumen, the steering lumen terminating at a point just proximal to the distal end of the sheath. The ablation device, as part of the ablation system, can be placed within a first of the at least one working lumen and remotely manipulated by the user. The steering system is adapted to cooperate with the ablation device to ensure proper placement of the ablating portion of the ablation device adjacent target tissue.

FIG. 5 depicts a steering system 30, comprising a flexible or bendable sheath 32 having at least one lumen 34 passing therethrough and at least one steering lumen 36, and a steering element 38 (shown in solid line to reduce the likelihood of confusion) which translates through the steering lumen 36. While not required, but is nonetheless preferable, steering lumen 36 terminates at a point proximal to the distal end of sheath 32. Having a termination point allows for use of multiple steering elements without dealing with the problems associated with infiltration of bodily fluids.

The steering element 38 can be any suitable steering control which imparts a deflection into the sheath 32. For example, the steering element 38 can be a flexible member having a proximal end fixedly attached to a handle portion (not shown) and a distal end to which is attached to a pull wire, the proximal end of the pull wire being operably attached to a control of the handle portion. Assuming constant flexibility along the entire length of the flexible member, through operation of the control by the user, tension is applied to the pull wire causing the distal portion of the steering element 38 to deflect. The deflection of the flexible steering member will result in deflection of the sheath 32 at the point where the flexible member is located within the lumen 36. It should be apparent that as the user translates the flexible steering member along the length of sheath 32, the point of deflection will change accordingly. Biocompatible metals, such as nitinol wire, or tubular structures, or other suitable means are examples of steering elements 38. Such elements 38, as discussed herein, can also be defined to have differing extents of flexibility along its length.

The steering element 38 can also be a rigid structure with respect to the distal portion of sheath 32. That is, a more proximal portion of sheath 32 may be adapted to have a greater stiffness than the distal portion. The steering element 38 may be adapted to have an intermediate flexibility, the element 38 taking on a linear form in the proximal portion of sheath 32, while taking on its desired shape, and thus deflecting the sheath 32, in the distal portion of sheath 32. This is especially useful in tubular structures where it is desirable to position the sheath 32 in contact with the inner wall of the tubular structure at one point along a line, for example. The steering element 38 can be adapted to include a linear wire having a distal section having a small "n" shape. As the steering system is translated within the steering lumen 38, the sheath 32 is continuously deflected along the line, the sheath 32 maintaining contact at a point along the surface of the sheath 32

As discussed above, flexible sheath 32 can include additional steering lumens 36a (not shown) at numerous azimuth locations with respect to the azimuth of lumen 36, to allow for greater degrees of freedom with respect to creating complex curvilinear structures. For example, with a steering lumen 36a located approximately 90° azimuth with respect to lumen 36, one bend is defined via lumen 36 and a second bend is defined via lumen 36a. As stated above, the user can define the exact location of the two bending points through translation of different steering systems 30 within the individual lumens 36. In this way the user can create two non-coplanar bends of specific angles and radii of curvature.

Alternatively, the sheath 32 can include two lumens, the second lumen 180° azimuth from the first, to allow for coplanar curves. Using such a system the user can achieve an "S" type curve in one plane, where the length or height of the "S" is dynamically defined by the user during operation by translating the steering elements 38 within the lumens 36. An "S"

type curve is particularly useful as a guiding sheath for advancement of an ablation catheter therethrough, as is discussed in greater detail below.

While the steering lumen 36 is shown running substantially parallel to the central longitudinal axis of the sheath 32, the lumen 36 can be formed to define other deflection types or characteristics. For example, if a user wanted to define a 90° bend at a specific location along the axis of sheath 32, the sheath 32 could be adapted to include a lumen 36 which starts at a proximal point at 0° azimuth and then at the predetermined point shifts to a point approximately 90° azimuth. As long as the distal end of the steering system is distal to the transition point of the lumen 36, the bend will occur at the transition site.

Steering system 30 may also include an additional lumen (not shown) which passes therethrough, having a distal opening adjacent distal opening 34. Such a lumen may be used for injecting a contrast agent or other similar material during a procedure, allowing the user to better assess the specific anatomy of the left atrium for example. Alternatively, at least one lumen 36 may be adapted to longitudinally pass through the sheath 32, providing access to the left atrium for injection of contrasting agents or the like.

As mentioned above, the steering system 30 may include an ablation device which translates therethrough. The steering system 30 can be adapted to receive ablation devices of any modality, or any described herein. For example, using radio frequency energy and a plurality of electrodes along the outer surface of an ablation device, the steering system 30 can be designed to transmit the RF energy from the internal ablation device to a point external to the outer surface of sheath 32. More specifically, when the RF ablation device is translated to a predetermined location within sheath 32, one or more electrodes on the inner surface of lumen 34 conduct RF energy to one or more electrodes on the outer surface of sheath 32, either at the same longitudinal location or at a different longitudinal location depending on what type of lesion and what lesion pattern the user desires to create. In this way the user can use the sheath 32 to define an ablation path as part of a desired lesion set and then advance the RF ablation device to a predetermined location to create the one or more lesions along the ablation path. Furthermore, as the sheath 32 is positioned at a first position, the user may want to limit ablations along that first defined ablation path to limit undesirable damage to adjacent tissue, the esophagus for example, during ablation. The RF ablation device can be keyed to the inner surface of lumen 34 to ensure the orientation of the ablation device with respect to the sheath 32 remains constant.

The ablation device discussed immediately above can be based on other types of energies which can transmit or emit energy through material, such as microwave, light, chemical, sonic energies, or other energies described herein. In each case the sheath 32 may be adapted to transmit the energy therethrough. For example, the sheath 32 can include a porous material which can define a desired ablation line from which a chemical ablation substance can advance into contact with target tissue.

Where the ablation device is designed to remain within the sheath 32, the sheath 32 may be adapted to have a closed distal end where the inner lumen 34 terminates prior to the distal end of sheath 32. The distal portion of sheath 32 can be adapted, through use of various steering elements 38, to create a desired geometric shape, in accordance with the present invention. Alternatively, sheath 32 can be directed to a desired location, the distal opening of sheath 32 defining an initial delivery point from which an ablation device, such as those discussed herein for example, is advanced.

With reference now to FIGS. 5B and 5C, another ablation device or sheath 40 will be discussed. As shown, the ablation device includes a sheath 42, a pull wire 44 and an orifice 46 located proximal to the distal end for allowing the pull wire 44 to pass therein. The pull wire 44 is operationally attached to a control as part of a handle portion (not shown). Under a tension force applied by a user operating the control, the distal portion of ablation device 40 would deflect into a loop structure, as shown. Upon release of the tension force the distal portion would then straighten. In this way a user can create a curve at the distal end of sheath 40 from a substantially straight configuration to a substantially curved configuration, the extremes which are depicted in FIGS. 5A and 5B.

While FIGS. 5A and 5B depict pull wire 44, it is important to realize there are other ways to achieve such deflection. For example, sheath 40 can include a steering element such as steering element 38 described above. Alternatively, the sheath 40 could include an element having different predetermined flexibilities defined along its length to define the sheath 40 into a predetermined orientation, for surrounding the pulmonary veins for example. Moreover, a system which includes both aspects could be utilized such that, due to the varying flexibility along the length of sheath 40, when the user applied a tension force to pull wire 44 the sheath will deflect at the varying points of greatest flexibility. Last, various aspects of other steering systems disclosed and described herein can be incorporated into steering system 40, as well as steering system 30.

The sheath 40 may include one or more pull wires (not shown) to be used in cooperation with pull wire 44 to achieve different desired geometries. Such additional pull wires can be attached to the sheath 40 at predetermined points to allow for the creation of the desired geometries. For example, a second pull wire could be attached at the midpoint between the distal end of the sheath 42 and the side port 46. When the loop configuration is achieved, applying a tension force to the second pull wire would act to modify the resulting loop shape.

When sheath 42 is used in conjunction with steering system 30, radiopaque elements, such as the radio frequency electrodes themselves, or other materials which fluoresce, can provide location information with respect to sheath 42 and system 30. The sheaths 32, 42 can be adapted to include materials which fluoresce with varying levels of intensity providing the user the ability to view the sheath 32, 42 positions under fluoroscopy. For example, the fluoro opacity of the sheath 42 can be greater than that of sheath 32 such that the sheath 42 can be viewed as it is advanced within the inner lumen 34 of sheath 32.

Figure 5E:
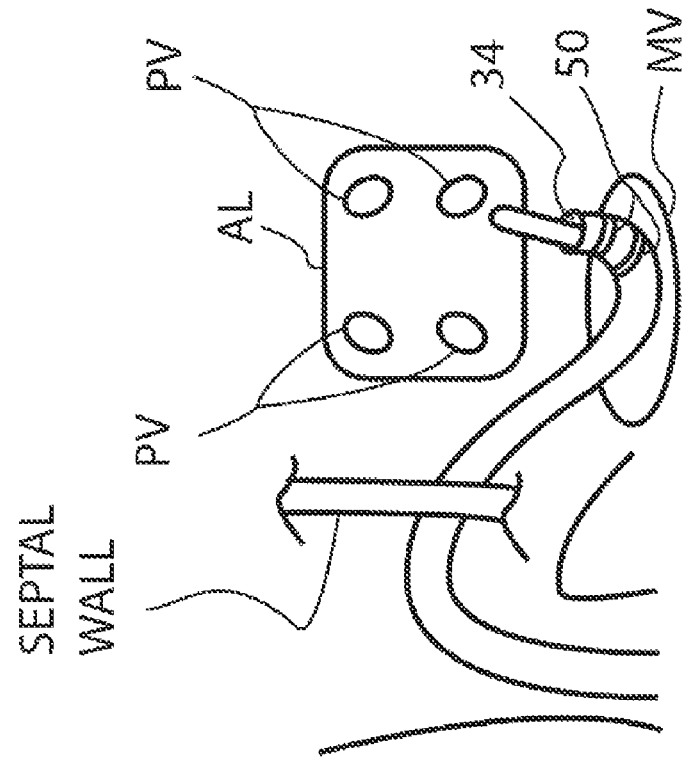
FIGS. 5D-5E are elevational views depicting the steering systems of FIG. 5A and FIGS. 5B-5C in cooperative operation within the left atrium of a heart, in accordance with various aspects of the present invention.
Figure 5D:
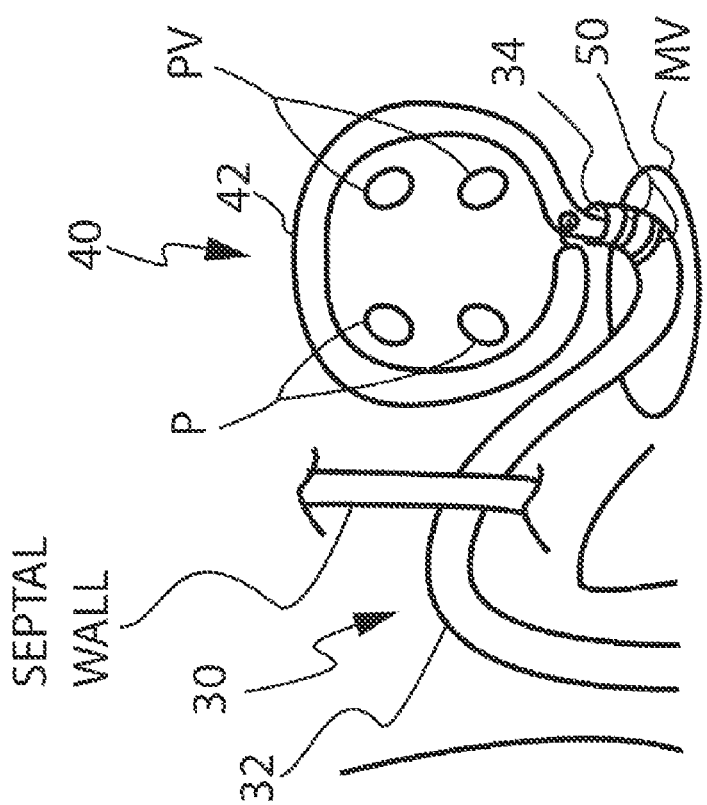

As schematically depicted in FIGS. 5D and 5E, sheath 32 can include one or more positioning electrodes 50 near its distal end. Such electrodes can serve multiple purposes. They can provide a means for easily locating the distal end of sheath 32, as well as offer feedback to the user allowing the user to determine whether the distal portion of sheath 32 is positioned against soft tissue. The electrodes can also be used to capture physiological information regarding the tissue with which it contacts.

When the desired configuration of sheath 40 is obtained, the target tissue is then ablated. As discussed above with respect to sheath 32, the sheath 42 can be adapted to cooperate with the deflection capabilities of sheath 32 such that sheath 32 can be used to generally orient an entrance to the left atrium through which the sheath 42 would travel. The sheath 42 would then be used to define the ablating line as part of the desired ablation pattern or set. With reference to FIGS. 5D and 5E, sheath 32 is used to create an entrance defined by the distal opening of lumen 34. Once sheath 32 is positioned, the ablation sheath 42 is translated through and out of the distal opening of sheath 32. Using deflection techniques described herein, the ablation sheath 42 is positioned about the PVs, as shown, and the target tissue adjacent the sheath 42 is then ablated.

With specific reference to FIG. 5A, methods depicted will now be discussed in greater detail. Access to the left atrium can be achieved through a suitable transseptal opening. The sheath 32 can then be generally guided to within the left atrium via a guide wire as part of the transseptal sheath (not shown) system. Once within the left atrium the steering systems as discussed herein can be utilized to position the distal opening 34 of sheath 32 adjacent the mitral valve MV, pointing generally toward the posterior wall of the atrium.

The ablation sheath 40 can then be introduced such that when it exits the distal opening of sheath 32 it is directed generally toward the posterior wall of the left atrium. Using pull wire 44, or other steering means as discussed herein, the ablation sheath 40 is then positioned in a predetermined fashion, encircling the pulmonary veins PV for example, as depicted. Once positioned, the ablating element(s) can be activated and an encircling lesion can be created. As discussed herein, the ablating elements can be incorporated into sheath 42, such as radio frequency electrodes on the outer surface of sheath 42, or can be incorporated in an ablating device which is adapted to ablate from within the sheath 42, such as a microwave antenna structure for example. Furthermore, the ablating device within the sheath 42 can be adapted to translate within an inner lumen of sheath 42 allowing the ablating device to make several separate lesions along the desired ablation path, as part of a desired lesion pattern, if necessary. Once positioned and ablation has occurred, the desired lesion pattern is created, as depicted as line AL in FIG. 5E.

During the procedure, contrasting agent can be injected through lumen 34 or a separate lumen of either sheath 32 or sheath 42 to ensure that the four pulmonary veins are surrounded, or otherwise the sheath 42 is properly positioned in the predetermined fashion.

If desired, an ablation line from the mitral valve annulus to the encircling ablation line created through methods described above can also be created. As discussed above, the electrodes 50 would be used to determined whether the distal end of sheath 32 is in contact with soft tissue and not in contact with the mitral valve MV itself. Ablation of the mitral valve could potentially lead to mitral regurgitation, reducing the heart's ability to effectively pump blood. With the opening of sheath 12 placed at a point where the soft tissue of the left atrium comes into contact with the mitral valve, sheath 42 or another ablation device, can be used to ablate the mitral valve annulus lesion desired, as depicted in FIG. 5E.

With reference to FIGS. 6A and 6B, another transseptal approach in accordance with the present invention is shown, this approach utilizing the steering system of FIG. 4. FIG. 6A depicts heart 80 in section, the plane of section crossing through the four main chambers of the heart, a right atrium 82, a left atrium 86, a right ventricle 92 and a left ventricle 94. In general, non-oxygenated blood flows from the body into the right atrium 82 via the vena cava, from the right atrium 82 to the right ventricle 92 via a tricuspid valve 84, the right ventricle 92 pumping the blood to the lungs for oxygenation. Oxygenated blood from the lungs returns to the left atrium 86 via several, typically four, pulmonary veins 90, travels to the left ventricle 94 via a mitral valve 88, the left ventricle 94 pumping the oxygenated blood to the various tissues of the body, as well as to the heart itself.

In accordance with the present invention, an ablation catheter is intravenously guided from the femoral vein, antegrade with respect to the blood flow, through an inferior vena cava 83 finally reaching a point within the right atrium 82. A transseptal sheath or introducer, or other similar device, is utilized to create a transseptal opening between the right atrium 82 and the left atrium 86 and provides initial guidance for the ablation system to pass therethrough. The delivery sheath 16 is then advanced until its distal end is positioned within the left atrium 86, as shown, and the transseptal sheath may then be retracted. Once the delivery sheath 16 is positioned, the guide sheath 12 is advanced until the distal opening is directed toward a target tissue surface. The guide sheath 12 is then rotated as necessary to position the ablation portion along a desired plane which intersects with the posterior wall of the left atrium 86, along ablation line AL, for example. Similarly, any of the ablation devices or ablation systems disclosed herein may be adapted to be inserted into the left atrium 86 through a transseptal sheath or introducer to perform a procedure in the left atrium 86.

As shown, a first ablation A1 was created to encircle the left superior pulmonary vein 90. Once the first ablation A1 is created, the ablating portion 20 is slightly retracted and the guide sheath 12 is advanced to deflect the distal opening of the guide sheath 12 corresponding to the next desired ablation site. Once deflected, the ablating portion 20 is then advanced to engage the target tissue at the desired location, a location A2 for example as depicted in FIG. 6A.

The handle portion (not shown) can include a slider, or other control, which will translate the guide sheath 12 along its longitudinal axis. The slider is preferably adapted to selectively engage the guide sheath 12 at a specific position. In this way the guide sheath 12 can be initially positioned such that the distal opening of the guide sheath 12 corresponds to the distal opening of the delivery sheath 16. The slider can then be adapted to engage the elongate body of sheath 12 at this initial position, also corresponding to an initial indication on the handle portion. The handle portion can further include additional indicators, such as recessed or raised areas, marked areas, or illuminated areas, which corresponds to the amount the guide sheath 12 has been advanced from the initial starting position.

The same slider, or other control, may also provide for an indication representing the rotational orientation of sheath 12. Knowing the configuration of the distal geometric portion, the radius along the distal portion for example, along with other radial orientation information regarding sheath 12, one can operate the slider and be able to determine the corresponding amount of deflection the user is imparting to the distal end of guide sheath 12. For example, moving the guide sheath a known distance will result in a deflection of a known amount between the distal opening of the guide sheath 12 and the longitudinal axis of the opening of the delivery sheath 16. For more precise control, rather than a linear-moving slider control, the handle portion can include a rotatable control which uses interlocking screw members, pin and groove members for example, one member attached to the rotatable portion and the other member operably attached to the guide sheath 12, to translate rotational motion into linear motion. With such a system, a relatively large rotation can translate to a very small linear advancement of the guide sheath 12, resulting in more precise control.

Figure 6D:
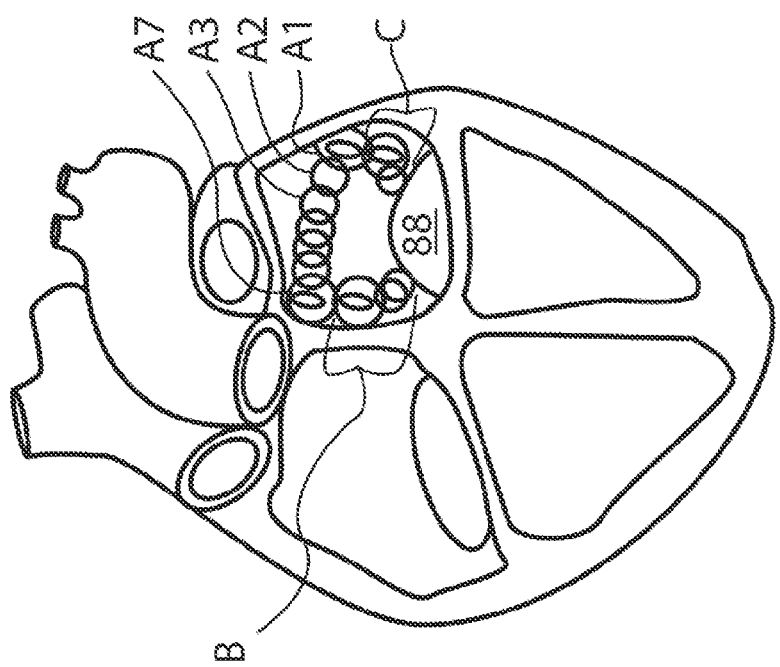
FIGS. 6C-6D depict another method in accordance with various aspects of the present invention.

Once the desired deflection is established and the ablating element is advanced to engage the desired target tissue location, as depicted in FIG. 6A, a second ablation can be created along ablation line AL. With specific reference now also to FIG. 6B, once the second ablation A2 is created the guide sheath 12 is further advanced, as discussed above, to further deflect the distal opening of the guide sheath 12 defining an additional desired target tissue location. An additional lesion A3 is created at this third desired ablation location, the lesion A3 being continuous with the previously created lesions A1 and A2, as best depicted in FIG. 6D. As shown, due to the geometric nature of the ablating portion 20, the created lesions A1-A3 intersect at least at two points, providing at least two barriers or conduction block lines to the passing of undesirable signals, as described above. The geometric shape of the ablating portion 20 allows for easier control over the ablating element itself as well as the creation of continuous lesions including multiple barriers or lesion lines, ensuring proper lesion formation and increasing the effectiveness of an ablation procedure.

Turning momentarily to FIG. 6D, an exemplary lesion set is shown which isolates the pulmonary veins 90 from the remaining atrial tissue. The three additional lesions as part of lesions B and the two additional lesions as part of lesions C can be created through further simple manipulation of guide sheath 12. More specifically, once lesion A7 is created, rather than further advancement of guide sheath 12 resulting in further deflection, the guide sheath 12 is simply rotated such that the guide sheath 12 distal opening is directed toward the first B lesion encircling the inferior pulmonary vein 90 and the encircling lesion is created. The guide sheath 12 is further rotated to create the additional two B lesions of FIG. 6D, ultimately forming a continuous lesion to the mitral valve 88. In similar fashion, the two C lesions are created to form the overall lesion pattern of FIG. 6D.

Now turning to FIG. 6C, another method in accordance with the present invention will be discussed. As shown, an opening in the left ventricle of the heart 94 is created, near the apex for example, and a sealing member SM is then placed therein. The sealing member SM provides a passage through which tools can be passed with little to no blood loss. While shown as a separate device, other forms are contemplated. For example, the SM can also be a purse string suture about the access opening leading to the left ventricle, sealing the tissue against the introducer. As should be readily understood, while shown advancing from an apical location, other approaches are contemplated, such as through any heart wall, the wall of the left atrium itself for example. The distal opening of the delivery sheath 16 is then advanced passed the SM, through the left ventricle 94 and into the left atrium. The delivery sheath 16 of the FIG. 6C embodiment may be rigid, for example formed from stainless steel or other rigid biocompatible metals or plastics. Additionally, the delivery sheath 16 may be mounted directly to a handle portion (not shown) allowing for direct and precise control over the distal tip of sheath 16.

As with the method of FIGS. 6A and 6B, the guide sheath 12 is then advanced to a point where the distal opening of sheath 12 is directed to the target tissue 18 encircling the left superior pulmonary vein 90, around which a first ablation A1 is created. As should be apparent, the guide sheath 12 is then rotated about its main longitudinal axis until the distal opening of sheath 12 is directed toward target tissue corresponding to lesion A2, as depicted by arrow R. The process is repeated and the third lesion A3 is created corresponding to the placement of ablating portion 20 as depicted in FIG. 6C. The process is further repeated until the desired lesion pattern, the lesion pattern of FIG. 6D for example, is created.

Access to the apex of the heart 80 can be achieved through any suitable means. For example, an intercostal opening can be created through which the delivery sheath 16 can pass. Additionally, a subxyphoid approach can be utilized whereby an opening is created in the thoracic cavity immediately inferior to the rib cage. The sheath 16 can then be directed through the opening and generally toward the apex of the heart through any suitable means, directly or via a guidewire or other suitable guiding device for example.

Figure 6C:
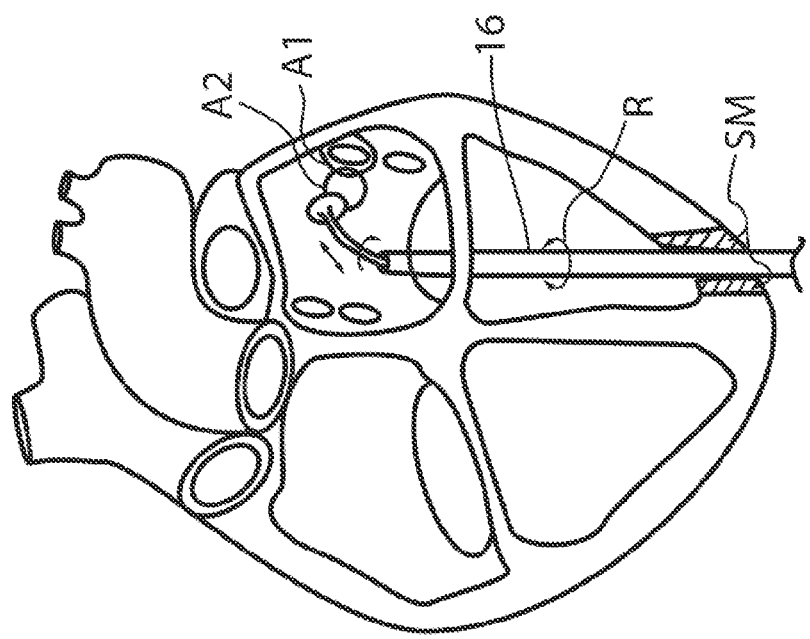

Another important aspect of the surgical embodiment of FIGS. 6C and 6D involves tactile feedback the user perceives during the procedure. With such surgical tools, forces associated with the procedure, including tissue contact forces, are transmitted along various elements of the tool, ablating portion 20 and sheaths 12, 16 for example. In this way, the user can perceive engagement of the ablating portion upon the target tissue surface and limit further applied forces, thus limiting the chance of perforating the tissue. In addition to adding a level of safety to the procedure, tactile feedback will also result in a procedure requiring less time since the user will be more confident about the positioning of the ablating device adjacent the target tissue. Questioning of the proper placement of an ablating portion can dramatically increase procedure time, especially in the use of point ablation systems or other systems where it is unclear whether the ablating portion is in substantial contact with the target tissue. While tactile feedback applies to any embodiment disclosed herein, including catheter embodiments, it is more applicable to the surgical tool due to the shortened sheath lengths and less tissue contact along such lengths which may impede proper and accurate tactile feedback.

While the heart 80 has been generally depicted, it should be clear that the various sheaths described herein, sheaths 12 and 16 for example, as part of a desired steering system must be able to address the target tissue surface in accordance with the configuration of the utilized ablating portion. For example, given the embodiments of FIG. 6 which require advancement toward the target tissue generally normal to the target tissue surface, the steering system must be able to direct the ablating portion from about 0° to about 145° with respect to the longitudinal axis of the delivery or guide sheath. Now turning to FIG. 6E, this concept will be described in greater detail.

FIG. 6E generally depicts a simplified anterior view of the left atrium. Lines LPV and RPV represent a plane defined by the openings of the left and right pulmonary veins, respectively. Line SP, shown in dashed, depicts the general approach line taken by the delivery or guide sheath upon access to the left atrium from a general apical approach. If the ablating portion is to be directed toward the LPV, the steering system must be able to impart a deflection of approximately 90° with respect to the longitudinal axis of the delivery or guide sheath, along line SP for example, as indicated by arrow SP-LPV. Alternatively, to direct the ablating portion toward the RPV, the steering system must be able to impart an acute angle with respect to line SP, as indicated by arrow SP-RPV. It should be apparent that deflection along one plane is all that is necessary since the deflection point directionality, for example defined by the distal opening of sheath 12, can be rotated about the line SP. This discussion generally applies to a retrograde approach as well, as more fully discussed below, since, as with the apical approach, the distal opening of a delivery or guide sheath, sheath 16 for example, is placed within the left atrium from a left ventricle approach. Also, when considering a transseptal approach, the device advanced in an antegrade manner as discussed above, where the longitudinal axis of the delivery or guide sheath is generally defined by line L1, one can observe, while the approach to the LPV is generally direct, the approach to the RPV requires deflection of approximately 140°.

The ablation systems in accordance with the present invention can also be positioned via a retrograde approach. In such an approach the delivery sheath 16 would be intravenously directed into the left ventricle 114 via the aortic arch and then deflected to eventually place the distal opening of the sheath 16 within the left atrium 86. Deflection can be made through any suitable means, for example via a steering catheter system using one or more pull wires to deflect the sheath 16. Additionally, the sheath can be adapted to follow a guide wire which was previously placed within the left atrium via a retrograde approach. Also, multiple sheaths can be used, sheaths similar to sheath 12 for example, employing any means of deflection discussed herein, to advance the distal opening of the delivery sheath 16 into the left atrium 86.

Once the distal opening of the delivery sheath 16 is positioned within the left atrium 86, the desired lesion pattern, the lesion pattern of FIG. 6D for example, can be created through simple movements as discussed herein.

Now turning to FIGS. 7A-7N, various exemplary flexible planar ablating portions in accordance with the present invention will be discussed. As stated above, the ablating portions are preferably formed, or otherwise adapted, to create ablation lines which have specific predetermined geometric shapes. While described as planar ablating portions, it should be apparent to one of ordinary skill that the flexible nature of the structures will allow the ablating portions to be placed substantially in contact with the target tissue surface, despite the fact that the target tissue surface is concave, as along certain locations of the left atrium endocardial wall for example. The geometric shaped ablating portions create various area ablations which are adapted to enable a user to more easily and effectively create long continuous lesions within biological tissue.

Figure 7G:
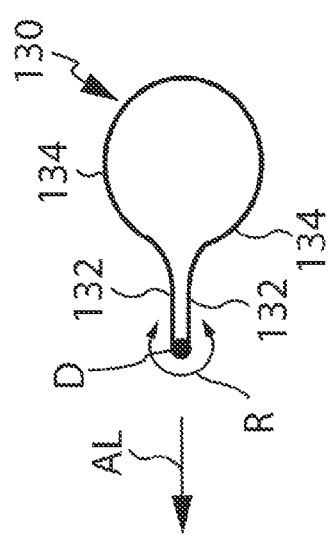
FIGS. 7A-7P depict exemplary planar embodiments in accordance with various aspects of the present invention.
Figure 7H:
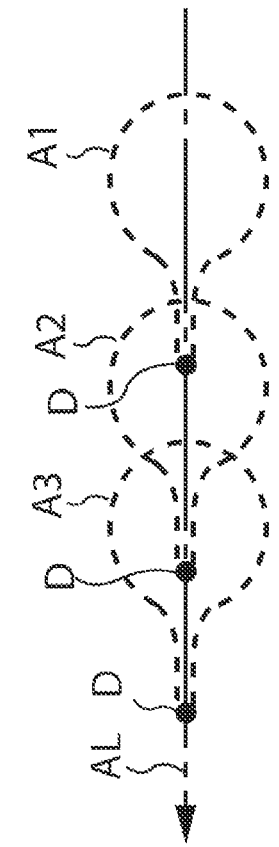
Figure 7I:
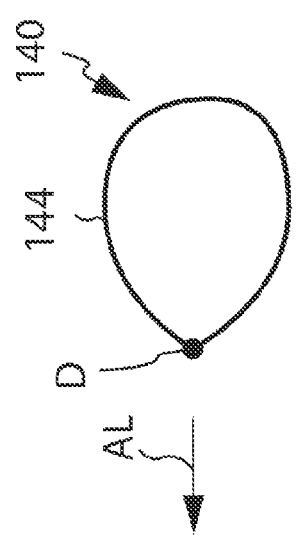
Figure 7J:
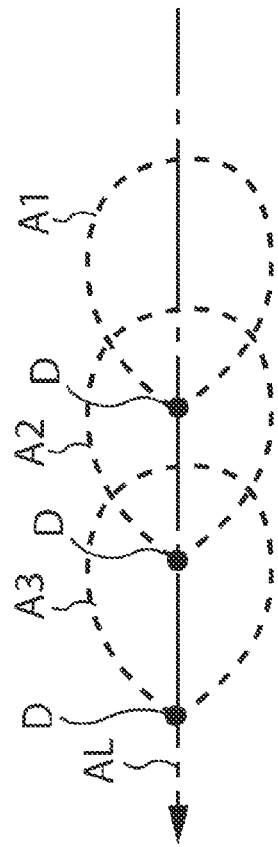
Figure 7P:
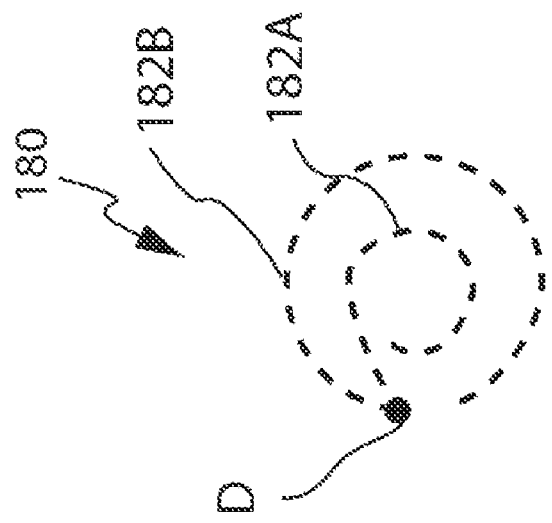

The ablating portions of the embodiments depicted in FIGS. 7A-7P are shown in schematic form, and can be constructed in any suitable manner, and using any modality, as discussed herein or generally known in the art. The design of ablating portion embodiments depicted in FIGS. 7A-7P can be used to design ablating portions of any of the devices disclosed herein. Generally, the ablating portions define two dimensional geometric shapes having an overall length and a width or other dimensional values for example, which allows for the more efficient creation of long continuous lesions in the target tissue with minimal movement and precision required. The overall length and width of the geometric shapes can be of any suitable dimension, the longer dimension, if any, preferably being placed substantially inline with or adjacent to the desired ablation line, as discussed below. The geometric configuration of the ablating portion allows great freedom of motion while moving along a desire ablation line. As long as the movement is less than the length of the geometric shape along the ablation line, a lesion continuous with a previous lesion will be formed. Last, for purposes of discussion only, the embodiments of FIGS. 7A-7P are shown with reference to an interface to a delivery system D. The delivery system can be any suitable system know in the art or discussed herein, such as the distal end of either the guide sheath or delivery sheath described herein for example. Additionally, the longitudinal axis of the delivery system can form an angle with respect to the target tissue from about 0° to about 90°.

Now turning specifically to FIGS. 7A and 7B, a first exemplary planar ablating portion 100 in accordance with the present invention will be discussed in greater detail. As shown, the ablating element has a general "J" shape and comprises a substantially linear section 102 followed by a distal curved section 104 forming the distal end of ablating portion 100. The distal curved section 104, while shown forming an arc of approximately 180° with respect to section 102, can form an arc in the range of about 10 degrees to about 360 degrees, the latter being discussed in more detail below. As with the other geometric shapes defined by the embodiments of FIGS. 7A-7P, the ablating portion 100 can be rotated, or otherwise positioned, with reference to a desired ablation line AL.

With reference specifically to FIG. 7B, with the first exemplary ablating portion 100 orientated with respect to the ablation line AL corresponding to a first ablating position shown in dashed as A1, a first ablation or lesion within the target tissue can be created in a similar fashion as described above. Once created, only simple movements by the user are required to properly place the ablating element for subsequent ablations. More specifically, the user can move the ablating portion 100 along the desired lesion line AL in order to properly position the ablating portion 100 for creation of a subsequent ablation, ablation A2 for example, being continuous with the initial ablation A1, using the steering systems discussed herein for example. Similarly, additional lesions can be created through further simple user movements to create a continuous lesion, as part of a desired lesion pattern. As should be apparent from FIG. 7B, the specific geometric shape of ablating portion 100 allows for the movement of ablating portion 100 along the desired ablation line, ablation line AL for example, with less required precision, but increased efficacy with regard to the ablation procedure itself. The geometric shape increases the likelihood of creating a desired continuous lesion during beating heart procedures. Additionally, as stated above, it is important to note that the actual surface ablation created can have the general geometric shape of the ablation portion itself, or can take on the overall geometric shape of the ablation portion, an exemplary overall geometric shape indicated by line AL1 of FIG. 7B, corresponding to ablation A1.

A second exemplary flexible ablating portion 110 is depicted in FIG. 7C. As shown, the element 110 comprises two generally linear sections 112 and a curvilinear section 114. While shown depicting the curvilinear section 114 positioned in the middle of the ablation portion 110, the curvilinear section 114 can be defined anywhere along the ablating portion 110. As with the embodiment of FIG. 7A, the ablating portion 110 is rotated to an orientation generally as depicted with reference to a desired ablation line AL. As the ablating element is subsequently moved to create multiple continuous ablations, at corresponding locations A1, A2 and A3 along ablation line AL of FIG. 7D for example, the overall geometric shape of the ablation portion 110 ensures that for movements less than the overall length of the ablating portion 110, there will be one intersecting point between the individual lesions.

The exemplary flexible ablating portion 120 of FIG. 7E is similar to portion 110 but provides an initial linear portion 122 at is proximal end and includes an elongate curved portion 124 forming its distal end. It should be apparent that the distal curvilinear section can include one or more linear sections therein. Further, the initial proximal linear section 122 can be longer to provide for a longer individual lesion.

As discussed with reference to the embodiments of FIGS. 7A and 7C, FIG. 7F depicts an exemplary continuous lesion created by ablations A1, A2 and A3. It should be apparent from the depiction that the specific geometric structure of the ablation portion 120 allows greater freedom of motion during the ablation process.

Referring to FIGS. 7G-7L, exemplary flexible loop structures are depicted in accordance with the present invention.

Along with having overall geometric lengths and widths adapted to encourage the creation of a continuous lesion along a desired ablation line, loop structures also have the ability to create at least two barriers or conduction blocks to erratic signals related to cardiac arrhythmias. With reference to FIGS. 7G and 7H, another exemplary flexible ablating portion 130 is shown comprising two linear sections 132 and a curvilinear section 134. The curvilinear section can take on any suitable form allowing for the preferable width to length ratio to encourage the creation of continuous lesions with minimal and coarse user input.

As a desired continuous lesion is created, along ablation line AL of FIG. 7H for example, successive lesions intersect immediately proceeding lesions at two points corresponding to the general geometry of the ablating portion 130, increasing the likelihood of a successful ablation procedure. As discussed above, while the ablating portion 130 of FIG. 7G may result in the creation of a surface ablation generally corresponding to the area defined by portion 130, subsequent ablations A2 and A3, as shown, are deemed to intersect previous ablation A1 at least at 2 points.

FIG. 7I depicts an exemplary flexible ablating portion 140 having a single curvilinear section 144 in accordance with the present invention. While shown to be generally oval in shape, the curvilinear portion 144 can have any suitable shape which provides the desired ratio of width to length to enable the creation of continuous lesions, in accordance with the present invention. Similarly to the embodiment of FIG. 7G, ablating portion 140 creates lesions which provide at least two intersecting points or barriers for increased efficacy, as defined herein.

The exemplary flexible ablation portion 150 of FIG. 7K is similar to the ablating element 10 of FIG. 1 in that it comprises a curvilinear loop section 154, however the ablating portion 150 also includes a linear section 152 which, along with the loop section, provides for the creation of longer individual lesions with the inherent increased efficacy as discussed above related to other embodiments in accordance with the present invention. The ablation portion 150 is also similar to the exemplary embodiment of FIG. 7A, the distal curvilinear portion, however, in the FIG. 7K providing a curved portion of about 360°. As with the other loop embodiments discussed herein, if desired, the movement of the ablation portion 150 between subsequent ablation procedures can be controlled to form continuous lesions having at least two barriers, such as lesions A2 and A3 as shown in FIG. 7L, for example.

As generally shown in FIG. 7L, ablating portion 150 creates a lesion including an enclosed distal curvilinear section. The curvilinear distal section is particularly advantageous since it can be used as a further guide during an ablation procedure. For example, after a first lesion is created, such as lesion A1 of FIG. 7L, the user can then direct the ablation portion 150 along the desired lesion line AL1 of FIG. 7L to a point where the curvilinear portion 154 of ablating portion 150 encircles the starting point of lesion A1. More specifically, when the lesion A1 is created the proximal point of the ablation portion 150, visible through fluoroscopy or other techniques, can be recorded or otherwise defined through simple marking of a procedural fluoro display for example, or through computer generated means. Once recorded, the user can direct the curvilinear portion of ablation portion 150 to encircle the recorded point, the proximal point of the ablating element during the creation of ablation A1 in this example.

Additionally, as shown in FIG. 7L, as with other ablating portions disclosed herein, the ablating portion 150 can be rotated along another desired ablation line, line AL2 for example, and a further ablation A4 can be created which is continuous with the previously created ablations A1-A3. Through rotation and further placement of the ablating portion 150, a desired lesion pattern can created.

Now turning to FIGS. 7M and 7N, another exemplary flexible ablating portion 160 is shown having linear splines 162 arranged in a "T" shape with respect to the delivery system, the delivery system located at the top and middle of the geometric "T" shape. As is discussed in more detail below, ablating elements such as ablating portion 160 being delivered from a point more central to its geometric shape are advantageous since it provides more uniform force or pressure about the ablating device to encourage contact between the ablating device and the target tissue. Moreover, such centralized systems are more natural for electrophysiologists to use, building on their past procedural development and training, since the placement involves directing the delivery point D to a desired location generally central to the ablation created. Here, the user is using the same skills in directing the point ablation system to direct the various centralized area ablation systems discussed herein.

As shown, the ablating portion 160 comprises a number of linear sections or splines 162. While shown having three splines with respect to delivery point D, any suitable number of splines for a given corresponding geometric shape is contemplated. The splines may also be of differing lengths and may be radially positioned in any suitable manner to achieve the desired overall geometric configuration. Moreover, the splines may be radially arranged more closely spaced with each other, each spline adapted to include a curved portion such that the spline members are parallel with respect to each other substantially over the length of each spline, as discussed with reference to FIG. 7O below.

Preferably, the spline forming the length, or longest dimension, of ablation portion 160 as depicted in FIG. 7M is slightly longer than the remaining splines. In such a configuration, as discussed with other exemplary embodiments, the longer spline 162A is positioned substantially in line with the desired ablation line AL through simply rotational motion of the ablating portion 160, indicated by arrow R. Using methods discussed herein a continuous lesion can be formed through further simple movement and ablation of target tissue along the desired ablation line AL of FIG. 7N. In accordance with the present invention, the ablating portion 160 is adapted to be moved a fraction of its length, e.g. a fraction of the length of spline 162A. The vertical displacement of the individual ablations A1-A4 more accurately portrays displacement errors due to the natural physiological motion of the beating heart and the blood flowing therein. With delivery systems of sufficient stiffness, held in place by user control or contact forces of anatomical structures, the motion of the delivery system and, thus, the ablating portion itself translating therethrough will be minimized enabling the creation of continuous lesions, as depicted in FIG. 7N for example.

Figure 7O:
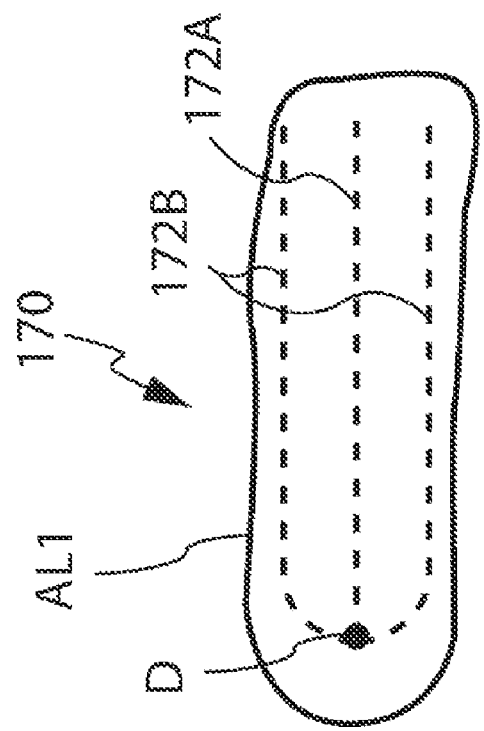

Now turning to FIG. 7O, an alternative exemplary spline ablating portion 170 is shown having three spline members 172. As depicted, spline members 172B include proximal curved portions aligning spline members 172B parallel to spline member 172A. The resultant configuration, provided ample ablative energy application, can produce an area ablation as represented by line AL1 of FIG. 7O. As discussed elsewhere herein, such geometric configurations resulting in area ablations are advantageous since they provide a higher probability of success with respect to linear ablating portions, or otherwise ablating portions having only a single spline member, the single spline member oriented along the desired ablating line.

As discussed with respect to other exemplary embodiments herein, with reduced ablative power applied the resultant ablation may be more consistent with the actual geometric configuration of spline members 172, the ablation for example comprising three separate linear ablation lines proximately connected and spaced therebetween. Moreover, the ablating portion 170 allows for the creation of at least one conduction block with respect to errant signals when multiple area ablations are created forming a desired continuous lesion. While each spline member 172B is depicted as terminating equidistance from spline member 172A, other configurations are contemplated. For example, the distal ends of spline members 172B can include curved portions directing the distal tips of spline members 172B toward, however not necessarily in contact with, the distal tip of spline 172A, resulting in a closed area ablation upon application of ablative energy. Alternatively, one or more of the spline members 172B may include intermediate curved sections (not shown) which effectively widen the overall geometric shape of ablating portion 170 along its length.

As with the exemplary embodiment of FIG. 7M, the spline members 172 include one or more ablating elements thereon from which ablating energy is applied to the target tissue. While shown having three spline members 172, additional spline members 172, at any suitable individual length to define the desired geometric configuration, are also contemplated.

Turning to FIG. 7P, another exemplary embodiment depicting an ablating portion 180 will be discussed in greater detail. As shown, the ablating portion 180 includes two concentric curvilinear spline members 182. Such a system allows the creation of area ablations having at least two lines of conduction block with respect to a point central to the inner spline 182A, such as a pulmonary vein ostium. Additionally, such a system, as discussed with respect to other ablating portions comprising loop sections, allows for the creation of continuous lesions having at least two lines of conduction block, preventing undesirable signals from triggering atrial fibrillation.

While the embodiments of FIGS. 7O and 7P are depicted with delivery points D located generally laterally with respect to the ablating portion geometric shape, other delivery points D are contemplated, as discussed in more detail below. For illustration purposes only, the delivery points, that is the points from which the ablating portions exit the steering or delivery systems, can be located more central to the geometric shape of the ablating portion providing a more consistent contact force between the ablating portion and the target tissue. Additionally, the ablating portions can form any suitable angle with respect to the delivery point D or the delivery point D can include a flexible joint as discussed in more detail below.

Another advantage of systems incorporating ablating portions which form ablations defining at least two lines of conduction block is such systems provide for a higher overall probability of creating a desired lesion along a lesion line as part of a desired lesion pattern. More specifically, due to the non-uniform nature of certain biological tissue surfaces, certain endocardial surfaces of cardiac tissue for example, it is often difficult to ensure that proper placement of the ablating portion with respect to the target tissue is achieved. For illustration purposes only, consider an ablation system having an ablating portion similar to ablating portion 170 of FIG. 7O, where the ablating elements require physical and direct contact with the target tissue surface. Such non-uniform tissue surfaces can impact the ability for certain splines 172 to properly engage the tissue and create a desired lesion as part of a lesion pattern. In this case, assuming ample ablative power is applied to create overlapping lesions between each adjacent spline pair, other ablating elements on other spline members 172 would make the desired lesion at that location upon the target tissue surface. Thus, as should be readily apparent, while the individual ablations created by individual spline member 172 may not be continuous with respect to the individual corresponding spline member 172, the overall lesion created by ablating portion 170 will be continuous.

Figure 8G:
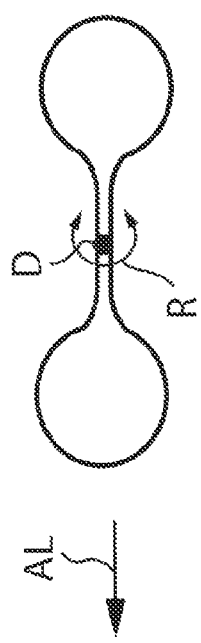
FIGS. 8A-8P depict additional exemplary planar embodiments in accordance with various aspects of the present invention.
Figure 8H:
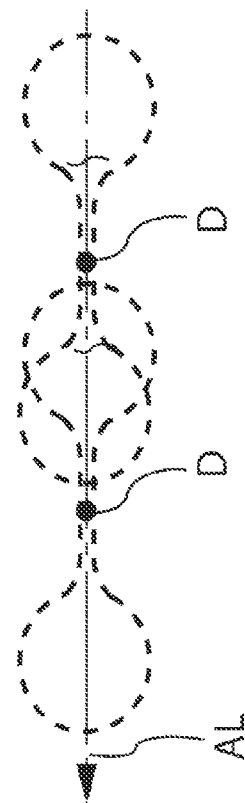
Figure 8I:
Figure 8J:
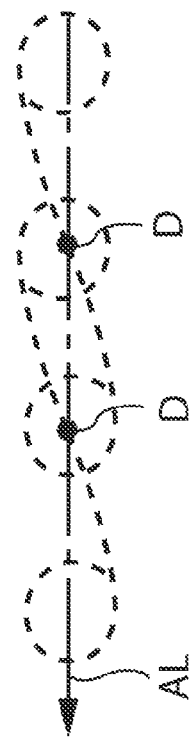
Figure 8K:
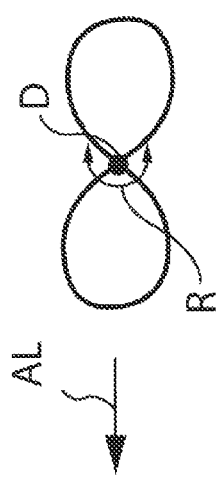
Figure 8L:
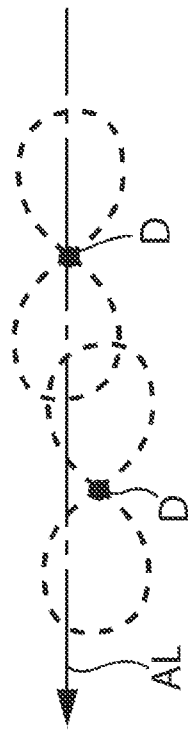

Now turning to FIGS. 8A-8N, additional exemplary ablating portions in accordance with the present invention are depicted. FIGS. 8A-8N depict ablating portion structures similar to the embodiments of corresponding FIGS. 7A-7N, however including symmetrical or non-symmetrical element structures with respect to a delivery point established along the length of the ablating portion itself. As shown with specific reference to FIGS. 8A, 8C and 8E, the ablating portion may be nonsymmetrical with respect to a delivery point D. For example, the ablating portion may include a symmetrical or mirrored structure about the delivery point D as in the case of FIG. 8C, or, alternatively, a non-symmetrical structure about the delivery point D as in the case of FIGS. 8A and 8E. In certain circumstances, physically establishing the delivery point more central to the ablating element itself can be more advantageous. As stated above, a more centralized delivery point provides for a more uniform force between the ablating portion and the target tissue. Additionally, it provides for easier creation of certain area ablations through the simple rotation of the ablating portion about the delivery point. Last, it provides a natural transition for electrophysiologists since the steering reference is more centralized to the ablating element, similar to point ablation devices currently in wide use. The design of ablating portion embodiments depicted in FIGS. 8A-8N can be used to design ablating portions of any of the devices disclosed herein.

As with FIGS. 7A-7N, the exemplary embodiments of FIGS. 8A-8N depict the ablating portion in outline form, however, the actual ablation created can differ from the depicted geometric shape, as discussed above. Any modality can be used, as described herein. For example, considering a radiofrequency based ablation system, the ablating element can include a number of spaced apart electrodes arranged along the length of the ablating portion. Alternatively, for further illustrative purposes, the ablating portion can comprise one or more antenna structures adapted for transmission of electromagnetic energy into biological tissue. Additionally, as with the exemplary embodiments of FIGS. 7A-7N, for each exemplary embodiment shown in FIGS. 8A-8N, there is a corresponding figure depicting an exemplary lesion pattern. As discussed above relative to FIGS. 7A-7N, the exemplary lesion patterns shown in dashed line are for illustration purposes only. As stated above, the actual surface ablation may differ depending on the specific arrangement of the one or more ablating elements and the ablation energy utilized and in the manner the energy is applied. The exemplary lesion patterns depict the advantages of the general structures when creating continuous lesions, as discussed herein.

The overall dimensions of the various exemplary embodiments of FIGS. 8A-8N may be similar to their FIG. 7 counterparts, or may differ in scale or dimension. The various exemplary embodiments of FIGS. 8A-8N are, for illustration purposes only, depicting alternative structures adapted to the exemplary embodiments of FIGS. 7A-7N, in accordance with the present invention. For example, while FIG. 8A is shown comprising a generally centralized delivery point D and two different ablating portion segments which extend therefrom, the exemplary embodiment of FIG. 8A could include two identical sections arranged approximately 180° radially from each other. Alternatively, the exemplary embodiment of FIG. 8A could include a plurality of "J" type structures, as depicted in FIG. 7A, mounted about the delivery point D, for creating area ablations in accordance with the present invention.

FIGS. 8G through 8L, 8O and 8P depict exemplary ablating portions comprising various loop structures arranged about a generally centralized delivery point D. As discussed above, along with the advantages of other ablating portions described herein adapted to define a generally planar geometric shape, the loop structures of FIGS. 8G through 8L, 8O and 8P have the ability to create continuous lesion patterns including at least two barriers or conduction block lines, preventing undesirable signals originating from within one or more pulmonary veins passing therethrough to a substantial portion of left atrial tissue for example. Such systems increase the likelihood of a successful ablative procedure. For example, viewing the midpoint areas of the created ablation patterns, as depicted in dashed line in the corresponding figures, one can see two barriers depicted in dashed line. The embodiments of FIGS. 8M-8P include a number of loops or splines which allow for the creation of continuous lesions without the need of precise rotational control of the ablation portion itself. As long as the delivery point D is moved less than the overall dimension of the ablating portion along the ablation line, as continuous lesion if formed.

Additionally, as discussed above, the actual ablation characteristics created by the ablating portion are directly related to the modality used for the procedure and specific arrangement of the one or more ablating elements. For example, with specific reference to FIGS. 8M and 8N, for an ablation system which utilizes radiofrequency energy applied to the target tissue via several electrodes mounted along the length of each of the four linear splines, depending on how the electrodes are energized differing individual lesions will be created. If the electrodes along each spline, for illustration purposes, are energized relative to each other then a linear lesion generally corresponding to the ablating portion geometric shape will be created. However, if all the electrodes are energized, either through bipolar application from one electrode on a first spline to another electrode on a second spline or through unipolar application where all electrode currents travel to a ground plane for example, a surface ablation similar to the ablation defined by line AL1 is created. The depth of the created lesion can be established through control of the ablative power and the application period of such power.

As with any other embodiments described herein, the exemplary embodiments of FIG. 8 can be steered or otherwise guided toward a desired target tissue location through any suitable steering system, including those disclosed herein.

Now turning to FIGS. 9 and 10, another embodiment and corresponding method in accordance with the present invention will be described. FIGS. 9A-9D depict an ablation catheter system 200 incorporating an area ablating portion in accordance with the present invention to create a plurality of ablations along numerous radial lines, the plurality of ablations resulting in a continuous curvilinear lesion about all or part of a pulmonary vein ostium.

Figure 9A:
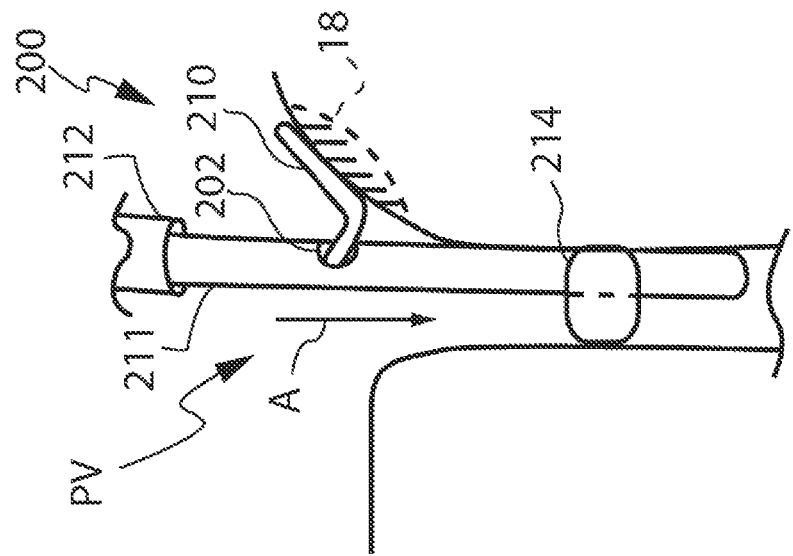
FIGS. 9A-9B depict elevational views of an exemplary embodiment incorporating an ablating element in accordance with various aspects of the present invention.
Figure 9B:
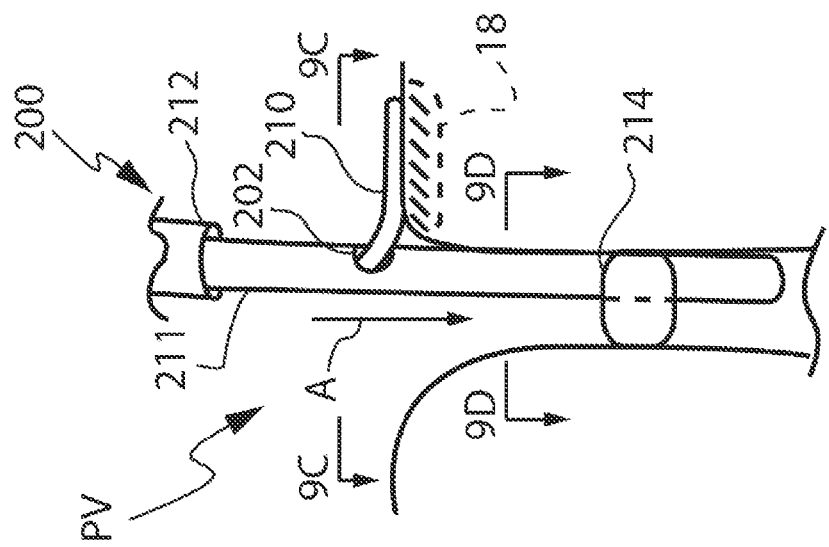
Figure 9D:
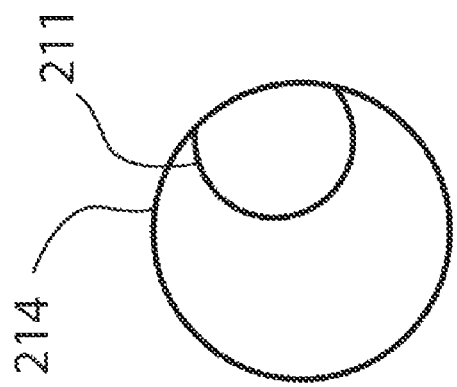
FIGS. 9C-9D depict elevational views of another exemplary embodiment incorporating an ablating element in accordance with various aspects of the present invention.
Figure 9C:
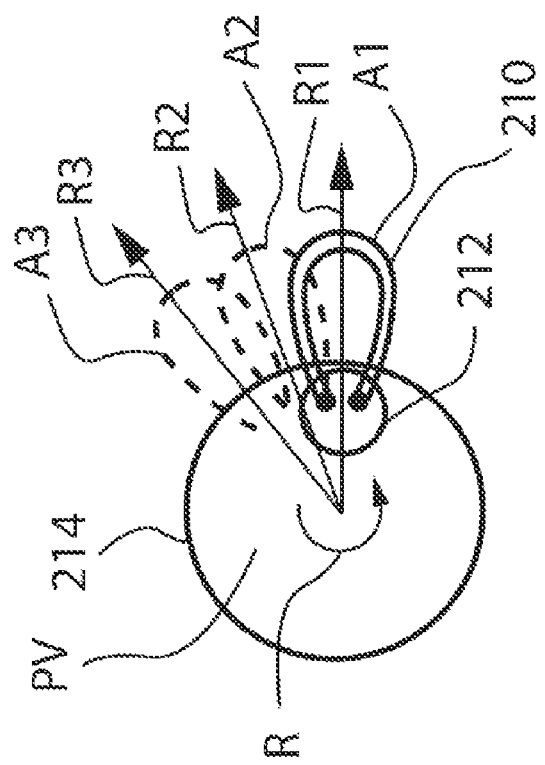

The ablation catheter 200 comprises an elongate sheath 211 having one or more openings or ports 202 near its distal end, as depicted, from which an ablating portion 210 extends, in the form of a curvilinear loop section best viewed in FIG. 9C. The average diameter of the loop formed by ablating portion 210 is between about 0.5 mm to about 10 mm, preferably from about 4 mm to about 6 mm. System 200 further includes a delivery sheath 212 having a lumen therethrough within which the sheath 211 translates.

Ablating portion 210 can be adapted to be collapsible as to conform to the outer surface of sheath 211 as sheath 211 translates through sheath 212. Alternatively, ablating portion 210 can be extendable from and retractable to a position adjacent to the outer surface via a handle control (not shown). For example, once the distal end of the ablating portion 210 has exited the distal lumen of sheath 212, the user can operate the control and extend the ablating portion 210 into its proper position. The ablating portion 210 can be extended or retracted through manipulation, e.g. translation, of either end or both ends of portion 210.

The ablating portion 210 is adapted to define a geometric planar shape. The ablating portion 210 is preformed to define a predetermined angle, for example less than 90° but preferably not less than 45°, between the distal end of the sheath 211 and the distal end of the portion 210. In this way, the ablating portion 210 can flex as it engages the target tissue 18, while advancing sheath 211 generally in the direction of arrow A, conforming to and ensuring proper contact between the ablating portion 210 and the target tissue 18 surface. With reference specifically to FIG. 9B, the ablating portion 210 of system 200 is shown in a further deflected position with respect to its position in FIG. 9A, in contact with target tissue 18.

As shown, ablating portion 210 preferably comprises an antenna element adapted to transmit electromagnetic energy. However, other ablative elements, as described herein, are contemplated. While shown with no dielectric covering, the antenna can be encased in a suitable dielectric, as discussed above. The system 200 may also comprise an anchor 214, a balloon or other expandable structure for example, which can hold or anchor the system in place within a pulmonary vein while ablating portion 210 exerts force upon the target tissue surface. The anchor 214 may include one or more passages (not shown) to allow blood to continue to flow from the pulmonary vein PV and into the left atrium during the ablation procedure. Anchor 214 may be constructed with any suitable biocompatible material including, but not limited to those materials discussed herein.

As shown with reference also to FIG. 9D, the sheath 211 is positioned off-axis with respect to the longitudinal axis of the anchor 214, the mutual walls of the anchor and sheath 211 engaging the pulmonary vein wall along the same radial line as the ablating portion 210 extends. The sheath 211 may also include one or more sensors to detect or transmit various signals related to the ablation procedure. For example, the outer surface of the mutual walls of the anchor 214 and sheath 211 may include one or more surface electrodes to ensure proper contact with the inner pulmonary wall has been achieved. The one or more electrodes can also be used for pacing and recording electrophysiological signals for verification of the efficacy of the ablation procedure. Sheath 211 may include one or more lumens therein, as necessary, to allow for transmission of such signals therethrough.

With use of the anchor 214, the sheath is advanced within the pulmonary vein until the ablating portion 210 engages the target tissue 18 at the desired radial position, the ablating portion 210 deflecting from its normal deployment position and held against the target tissue surface. The anchor is then expanded to hold the ablating portion 210 against the target tissue during the ablation of a first lesion, a lesion corresponding to position A1 of FIG. 9C for example.

Once the first lesion A1 is created, the anchor is slightly contracted to allow retraction of the guide sheath 211 to a point where the ablating portion 210 no longer is in substantial contact with the target tissue. The sheath is then rotated a predetermined amount and the sheath is once again advanced into the pulmonary vein until the ablating element once again engages the target tissue 18 at a new position where a second lesion A2 along a second radial line R2, is created. The process is repeated until the desired circumferential lesion around all or part of the ostium is created. Retraction and advancement of the ablating portion 210 during each ablation ensures the resulting lesion is created substantially on the surface of the atrial tissue surrounding the pulmonary vein, irregardless of the specific surface contour of such tissue.

Rotation of the sheath 211 can be achieved through any suitable manner. For example, the user can impart a torque upon the sheath itself from a position external to the patient's body. The torsion force is transmitted along the sheath body to the distal end which is rotated in response to the applied torque. The rotation can be electrically or mechanically controlled, the applied torque generated and applied to the sheath by a stepper motor for example or use of a ratcheting system, both being able to supply known values of rotational movement to the ablating portion to ensure proper formation of the desired circumferential lesion, the rotational movement being adapted for the specific geometric shape of the utilized ablating element for example.

While ablating portion 210 has been described as having a curvilinear loop structure, any suitable geometric shape is contemplated, for example any geometric shape defined herein. Moreover, linear structures which are rotated to create area ablations, such as ablating the circumferential area around a pulmonary vein ostium for example, are also well suited. One exemplary system is discussed below.

Such a system 200 is advantageous over systems which radially ablate from a lateral approach, the ablating element engaging at least a portion of the inner wall surface of the pulmonary vein, since a lateral approach requires uniform tissue surfaces around the pulmonary veins 110 to be fully effective. Since the tissue surfaces around the ostium of the pulmonary veins can vary greatly, proper tissue contact is never ensured with a lateral approach. Furthermore, ablating the inner wall of the pulmonary vein has been linked to stenosis, and it therefore undesirable.

The differing tissue landscapes surrounding the ostia also hampers circumferential ablation systems where contact between the ablating element and a circumferential tissue area around the ostium is essential. The relatively small size of the ablating portion 210 ensuring proper tissue contact, and the radial ablation methodology of the present invention overcome these problems.

Now turning to FIG. 9E, an alternative ablating system 220, similar to system 200, is shown. System 220 comprises a sheath 222 ending in an anchor device 224. The distal portion of sheath 222 is adapted to encourage deflection of the distal portion in the direction of the target tissue, as depicted. As with system 200, system 220 includes one or more ports 202 through which ablating portion 210 can be advanced. The one or more ports 202 of system 220, however, are positioned proximal to the deflection point of sheath 222. In this way, the sheath 222 can be first deflected toward the target tissue 18, as shown, and then the ablating portion 210 can then be advanced to a final position, shown in dashed line, generally atop the target tissue surface adjacent to the pulmonary vein ostium. As with sheath 211, the sheath 222 may include radiopaque markers or other indicators which can provide the user feedback with respect to the placement of the anchoring device 214 with respect to the target tissue. In this way, upon further advancement of sheath 222, the distal portion of sheath 222 will deflect in a desired manner to allow the ablating portion 210 to properly engage the target tissue surface.

Once initially positioned, a first ablation in the target tissue 18 can be made, as generally shown or indicated by the hashed portion immediately adjacent ablating portion 210. In a similar fashion to system 200, additional lesions can be created by rotation of the ablating portion about all or part of the pulmonary vein ostium.

Also depicted in FIG. 9E is a much thinner target tissue 18 in cross section, such as the LPV saddle or LPV-LAA ridge as depicted in FIG. 16. Systems such as those of FIGS. 9 through 11 are not limited by such tissue differences.

Figure 9G:
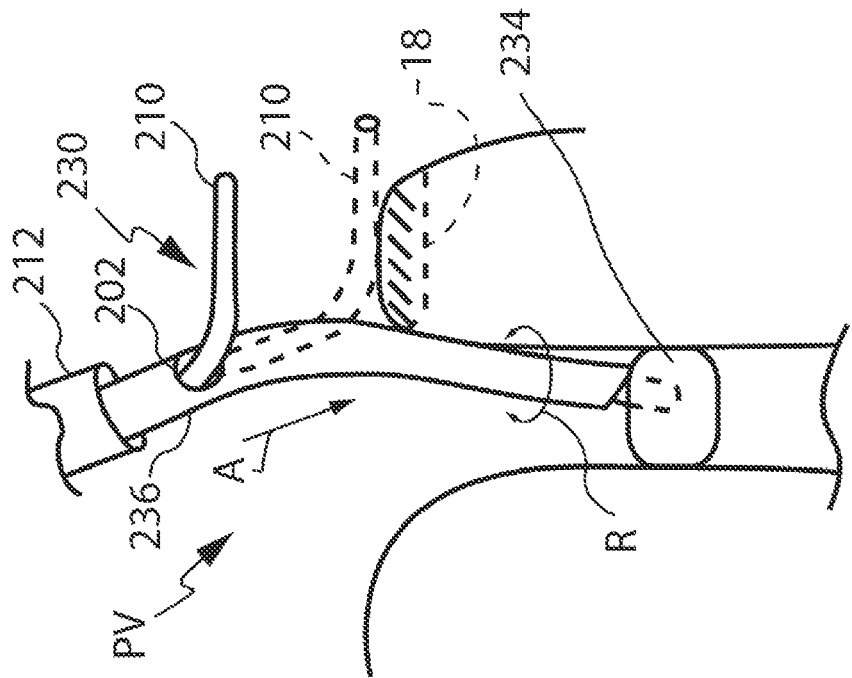
FIGS. 9F-9G depict elevational views of another exemplary embodiment incorporating an ablating element in accordance with various aspects of the present invention.
Figure 9F:
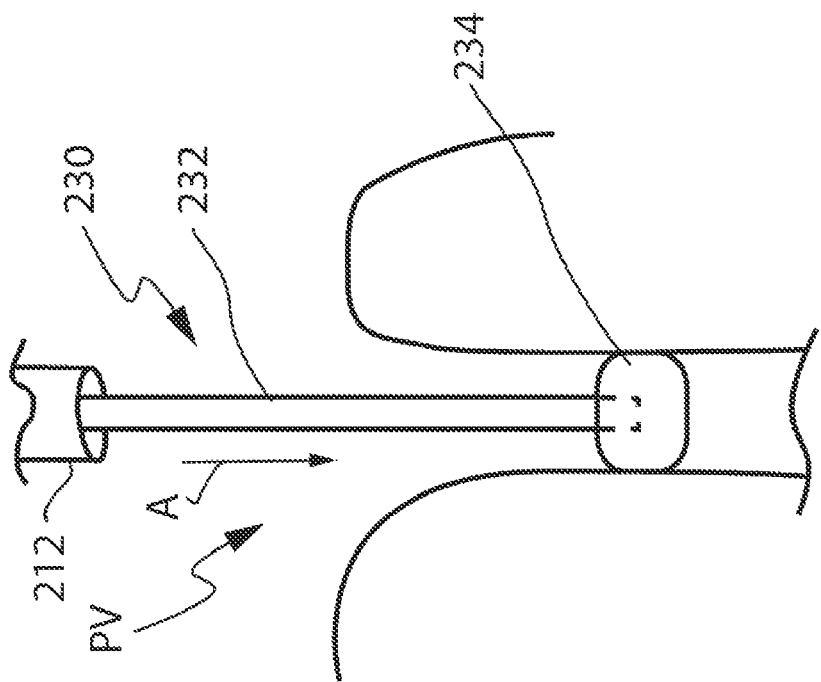

Now turning to FIGS. 9F and 9G, another alternative ablating system 230 is shown. Ablating system 230 includes an elongated flexible tubular member or guide wire 232 having a lumen in fluid communication with the internal chamber of a stabilizing device e.g. anchoring device 234 to stabilize member 232 in the anatomy. The tubular member 232 is attached to device 234 via any suitable means, such as biocompatible epoxies or material fusion or welding, or the like. Ablating system 230 further comprises a sheath 236 which includes at least one lumen therethrough which allows for translation over member 232. As discussed with respect to systems 200 and 220, the sheath 236 of system 230 includes one or more ports 202 through which ablating portion 210 can pass. Further, as with sheath 222, sheath 236 includes a predefined point of deflection which allows the sheath 236 to deflect in a know direction relative to its rotational azimuth. In this embodiment, the guide wire 232 is used as an elongated reference member to guide the sheath 236, which is used as a slidable positioning member having several ports 202 through which an ablating portion such as element 210 of FIG. 9G, or curvilinear ablating portion such as element 20 of FIG. 1 can be deployed. The curvilinear ablation portion such as element 20 can be adapted to be in a linear configuration inside sheath 36 and in a non-linear, curvilinear configuration outside sheath 36.

In one method embodiment, the user advances the anchoring device 234 into the pulmonary vein and then inflates the anchoring device 234. The anchoring device 234 can be inflated through any suitable means, such as passing saline through the inner lumen of member 232 filling and expanding device 234 for example. Once the anchor is positioned, the sheath 236 is then advanced until the distal end abuts the proximal end of anchor device 234. Upon further advancement of sheath 236 in the direction of arrow A, the distal portion of sheath 236 deflects toward the target tissue 18. In much the same way as described with respect to ablation system 220, a lesion around all or part of the pulmonary vein ostium can be formed.

Ablation system 230, however, is advantageous with respect to systems 200 and 220 since the sheath 236 can be rotated in the direction indicated by arrow R, positioning the ablating portion 210 at various radial points about the ostium of the pulmonary vein, without the need for continuously contracting and expanding the anchoring device 234. Another advantage of ablation system 230 with respect to systems 200 and 220 is the ability to position sheath 236 at several alternate locations on member 232 without the need for continuously contracting and expanding the anchoring device 234. Thus ablating portion 210 can be deployed from sheath 236 at a variety of locations relative to member 232.

As with sheath 222 of system 220, sheath 232 can include radiopaque markers or other indicators to provide the user with placement information relative to the pulmonary vein anatomy. In this way, upon further advancement of sheath 236, the distal portion of sheath 236 will deflect at a desired point allowing the ablating portion 210 to be properly placed upon the target tissue surface.

With reference to FIGS. 10A and 10B, an alternative ablating system 240 is shown incorporating a curvilinear ablating portion 210A. The ablating portion 210A, as with portion 210, is preferably an antenna structure adapted to transmit electromagnetic energy, preferably microwave energy, toward target tissue 18. As shown, the distal end of ablation portion 210A is curved back toward sheath 211 to form a blunt distal end adapted to engage the target tissue without causing undesirable tissue damage. As the sheath 211 is advanced, as discussed above with respect to system 200, the blunt distal end engages the target tissue 18 and slides or otherwise moves atop the target tissue surface as the sheath 211 is further advanced until finally positioned, such as the position depicted in FIG. 10A. Once positioned, ablation lesion segments are created in much the same way as with system 200; an initial ablation is created, indicated for example by the shaded area immediately below portion 210A, followed by subsequent ablations, along varying radial lines, the ablations forming a continuous lesion in the target tissue area around all or part of the pulmonary vein.

As with the embodiment of system 200, the ablation portion 210A can be either adapted to be compressed against the sheath 211 body while translating through guide sheath 212, or extended and retracted through any suitable means, a handle control for example as discussed in greater detail above. In a similar fashion as with portion 210, ablation portion 210A is preferably preformed such that when in an extended position, the body portion of element 210A forms an angle from about 0° to about 90° with respect to the distal end of sheath 211, preferably less than about 90° but not less than 45°. With reference to FIG. 10B, the ablating portion 210A is shown in initial contact with the target tissue 18 surface. At this point, as shown, the body of the ablating portion 210A forms an angle less than about 90°, with the distal end of guide sheath 211.

FIG. 10B also depicts the ability of ablating portion 210A to move, or otherwise be positioned, in a final operative orientation. As the sheath 211 is advanced in the direction of arrow A and the distal curvilinear end of ablating portion 211A engages the target tissue, further advancement of the sheath 211 causes the ablating portion 210A to further deflect and move along the target tissue 18 surface until it reaches its final orientation, substantially in contact with the target tissue 18 surface as shown in dashed. At that point the circumferential ablation process, as discussed above, can commence.

While shown as generally formed with a linear proximal section followed by a curvilinear distal section, the ablating portion 210A can assume other shapes. For example, the ablating portion 210A can be constructed as a single curvilinear section where the curvilinear section is generally circular or annular in nature having a diameter of from about 0.5 mm to about 20 mm. The curvilinear section can be formed as an ever-expanding spiral such that the more the element is extended from within the sheath 211 the larger the diameter formed. Such systems can be advantageous for engaging target tissue around the ostia, the tissue differing greatly from patient to patient. It should be apparent that with such expanding systems, corresponding changes may need to be made to the energy delivery system. Such systems may be better suited for radiofrequency based ablating devices, one or more electrodes being mounted along the outer surface of the ablating portion 210A for example. For illustration purposes only, such systems could also use a microwave ablating portion, as disclosed and described herein, including those embodiments where the ablative energy is emitted along the entire length of the ablating portion.

Since the ablation portion 210A is relatively linear with respect to portion 210, it should be apparent that creation of a circumferential lesion about a pulmonary vein with element 210A may require the creation of additional individual radial ablations or tissue lesions, to some degree requiring additional procedural time. The procedure time, however, can be somewhat reduced through manipulation of the power and ablation time parameters associated with the creation of the individual lesions, to the extent that such manipulations do not lead to undesirable tissue damage.

While discussed primarily in terms of creating continuous lesions about an orifice, the ostium of a pulmonary vein for example, the invention is not limited to such areas. For example, the ablation portion can be adapted to have a blunt tissue contacting surface immediately distal the ablating portion openings 220. The blunt tissue contacting surface, a convex surface for example, can then engage the target tissue, the center of the posterior wall of the left atrium for example, after which the ablating portion can be advanced to ablate a first ablation. Through methods described herein, the ablating portion can then be rotated a known amount to create the desired curvilinear area ablation within the target tissue. The ablating portion can be adapted to provide additional ablating length allowing for sweeping ablations about the posterior wall of the left atrium, ablating the tissue adjacent or surrounding any pulmonary vein from a centralized posterior wall position for example.

As stated above, it is often difficult to accurately position an ablating device in a desired orientation adjacent a target tissue site, especially during beating heart procedures. Another way to overcome the need for precise control is to provide an ablation system which is adapted to be positioned at a known location from which the ablating portion can be deployed. When deployed, the ablating portion is then positioned at a known orientation with respect to the ablating device, adjacent a desired target tissue site. FIGS. 11A-11G depict a first embodiment of such a system.

With reference to FIG. 11A, an ablation system 250 is shown comprising a tubular member ending in a distal spline portion 266 (also referred to as a mechanical member). In the embodiment shown, the tubular element is an elongate sheath 252 having a lumen which passes therethrough, the sheath 252 ending in a distal spline portion 266. Ablation system 250 further comprises an elongate member 262 (also referred to as a first elongate arm) adapted to be slidably positioned within the lumen of sheath 252 (where the sheath 252 is then referred to as a second elongate member). The distal lumen opening of sheath 252 defines an exit point from which the elongate member 262 translates. As is better shown in FIG. 11B, sheath 252 comprises an outer covering 254 and inner covering 264 of suitable material, as discussed elsewhere herein, along with a filler material 256, such as silicone or flexible TEFLON®, or other similar biocompatible materials discussed herein. The covering 264 acts to define the lumen throughwhich member 262 translates.

Sheath 252 further includes a deflectable spring member 258 (also referred to as a mechanical member) and a transmission device 260 (also referred to as an ablation device) for transmitting ablating energy to an ablating portion 268 for delivery to the target tissue 18. Changing the position of the distal end of sheath 252 relative to elongate member 262 changes the positions of spring member 258 and distal spline portion 266 relative to the position of elongate member 262. Thus, the distal end of sheath 252 can be used to deploy spring member 258 and distal spline portion 266 in the anatomy. In a preferred embodiment transmission line 260 includes an electrical conductor suitable for transmission of microwave energy. Preferably, the electrical conductor is an inner conductor which operates in tandem with an outer conductor to deliver electromagnetic energy to the ablating portion 268. More specifically, the transmission line 260 may be a properly sized coaxial cable incorporating an inner and outer conductor, and a dielectric material therebetween, as discussed herein. Alternatively, the functionality of the outer conductor may be located elsewhere, achieved through a thin metal deposit on the inner surfaces of coverings 254 and 264 for example. In any case, the outer conductor ends at or near the distal end of spline 266, the inner conductor continuing along the spring member 258 as depicted at the ablating portion 268 in FIG. 11A.

It is worthwhile to note that the combination of spline 266, spring member 258, and elongate member 262 creates a closed-loop reference assembly from which the ablating portion could be deployed or located. Additionally, it is important to note that a portion of the closed-loop reference assembly could be stabilized with respect to an anatomical structure to create a stable reference from which a tissue ablation, or other medical procedure, could be performed. Furthermore, a portion of the closed-loop reference assembly could be stiffer than the remaining portions to facilitate the creation of the stable reference. For example, elongate member 262 of FIG. 11A could be stiffer than spring member 258 and spline 266 to facilitate the creation of the stable reference, which would be the distal part of elongate member 262 which is in contact with the tissue, the inner wall of a pulmonary vein for example. The deployed close loop reference assembly comprising spline 266, spring member 258, and elongate member 262 forms a first profile or outline when deployed in an anatomical region. The first profile is adjustable by the user by changing the relative positions of spline 266, spring member 258 and elongate member 262. Similarly, ablating portion 268 located on the deployed close loop reference assembly forms a second profile or outline. In a preferred embodiment of the ablation system disclosed in FIG. 11A, the first profile and the second profile are spatially separated from each other. An advantage of this embodiment is the ability to abate tissue regions that are not directly adjacent to spring member 258.

The spring member 258 can be made of any suitable biocompatible material described herein which imparts the functionality discussed below. In one embodiment, spring member 258 is made of Nitinol. In an alternate embodiment, spring member 258 is made of stainless steel. The spring member 258 is constructed to cooperate or otherwise not directly interfere with the transmission of ablative energy, microwave energy for example. While the ablating element is shown on the side of spring member 258 opposite the tissue 18 surface, the ablating element could be placed against the target tissue itself, passing through an opening in the spring member 258 at the distal end of spline 266 for example. The opening can also serve to provide a point of increased flexibility, as discussed in greater detail below.

For example, the transmission device 260 can be one or more electrical conductors which lead to one or more radiofrequency electrodes defining ablating portion 268. The electrodes can be ring electrodes surrounding spring member 258 or can be formed through metal deposition, as discussed herein, upon only the surface of spring member 258 in contact with the target tissue 18. Alternatively, spring member 258 can comprise or define one or more electrodes along its distal length, the one or more electrodes used for ablating tissue or for sending and receiving certain electrophysiological signals related to the ablating procedure, as discussed elsewhere herein. The information obtained by sending and/or receiving electrophysiological signals related to the ablating procedure can be used to assess the degree of ablation of the target tissue. Elongate member 262 can also include such electrodes for receiving and transmitting such electrophysiological signals, indicating contact with the inner wall surface of the pulmonary vein or completion of the ablation procedure. While depicted having an ablation zone apart from the pulmonary vein PV ostium, the embodiment of FIG. 11A can be used to ablate tissue at any point along the spring member 258 distal to the spline 266.

As shown in FIGS. 11A and 11B, the spring member 258 travels to the distal end of spline 266 and then terminates near a distal portion of elongate member 262. Such termination can be made through any suitable manner, such as through the use of biocompatible epoxies for example. As depicted, while not necessary, the spring member 258 preferably has a rectangular crossectional area, the longer dimension of the crossectional area adapted to engage the biological tissue when properly placed or positioned. As will be more readily understood with respect to the discussion below, the spring member 258 act to move and properly place spline 266, and ultimately, ablation portion 268 upon the target tissue 18 surface.

Turning to FIG. 11C, a crossectional view of spline 266 is shown. The spline 266 includes an outer covering 253, and an inner covering 265, and a filler material 257 therebetween. Filler material acts to hold and retain the spring member 258 and transmission line 260 within spline 266, as depicted. Coverings 253 and 265, as well as filler material 257, may be identical materials with respect to coverings 254 and 264, and filler material 256, respectively. Additionally, coverings 253 and 265, as well as filler material 257, may be continuations of covering 254 and 264, as well as filler material 256, as long as the desired flexible point at the proximal point of spline 266 is formed or defined. In an alternate embodiment, the transmission line 260 located within the spline 266 could be replaced by a lumen wherein an ablation device could be slidably positioned. For example, the ablation portion 20 of ablation system 10 could be introduced in the lumen using the guide sheath 12 and transmission line 13 to translate the ablation portion 20 within the lumen. The ablating portion 20 would be deployed from a relatively linear un-deployed first configuration when located within the lumen of spline 266, to a relatively non-linear deployed second configuration, when passed the distal end of spline 266, which is in this case considered as a deployment member for the ablating portion. As mentioned, the mechanical force for translating the ablation portion 20 within the lumen of spline 266 would be applied by the guide sheath 12 and transmission line 13 which are operably connected to the ablation portion 20 as depicted and described herein. In addition, when the ablation portion 20 is deployed from the distal end of the spline 266, the guide sheath 12 and transmission line 13 may be used to further translate and/or rotate the ablation portion 20 with respect to the distal end of spline 266 to define a multitude of spatial relationships between the ablation portion 20, and the distal end of the spline 266, or any other portion of the close loop reference assembly comprising spline 266, spring member 258, and elongated member 262, as previously defined. In this way, the ablation portion can be deployed in multiple orientations with respect to the spline 266, spring member 258, or elongate member 262. Furthermore, the guide sheath 12 could be deflectable by any of the suitable means described herein to further position the ablation portion 20.

As shown in FIG. 11A, spline 266 is adapted to rotate in the direction of arrow R as it is deployed with the assistance of spring member 258. More specifically, with reference also to FIG. 11E, FIG. 11E depicts the ablation system 252 in a contracted configuration, within a delivery or steering sheath or other sheath described herein for example (sheath not shown for clarity). Once the distal end of system 252 exits a distal opening of the delivery or steering sheath, the spring member 258 acts to cause the spline 266 to rotate in the direction indicated by arrow R of FIG. 11A. This causes ablation system 252 to acquire an expanded configuration. As the system 252 is further advanced into an operative position, within a pulmonary vein PV for example, the spline 266 will engage surrounding biological tissue and continue to rotate. It is important to note that the spline 266 may be deployed before or after the distal end of sheath 262 is within the pulmonary vein, as long as the distal end of spline 266 is above or distal to the target tissue surface 18, or otherwise outside the pulmonary vein, when deployed. It is also important to note that the combination of the spring member 258, the spline 266, and the elongated member 262 creates a closed loop reference assembly for the ablating portion 268.

As shown, spring member 258 engages the inner wall surface of the pulmonary vein PV and the spring action of member 258 further encourages member 262 to engage the opposing inner wall surface. It should be readily understood that as the sheath 252 and/or elongate member 262 are translated back and forth, the shape of closed loop reference assembly is changed. This in turn adjusts the position of the ablating portion 268 upon the target tissue surface. Also, it should be readily understood that as the sheath 252 and/or elongate member 262 are rotated or twisted, the shape of closed loop reference assembly is changed. This in turn adjusts the position of the ablating portion 268 upon the target tissue surface. In this way, the ablating portion 268 can be positioned at a desired location with respect to the elongate member 262 and, ultimately, with respect to the pulmonary vein ostium. In one method embodiment, elongate member 262 is stiffer than spring member 258 and spline 266. The shape of the closed-loop reference assembly is modified by translating sheath 252 back and forth while stably maintaining the position of elongate member 262. In another method embodiment, ablating portion 268 is used to create a series of continuous lesions. This is done by ablating a first tissue region adjacent to ablating portion 268 to create a first lesion. Thereafter, the position of ablating portion 268 is moved to a second tissue region. This can be done by translating sheath 252 or elongate member 262 and/or rotating sheath 252 or elongate member 262. Thereafter, ablating portion 268 is used ablate a second tissue region adjacent to ablating portion 268 to create a second lesion such that the first lesion and second lesion are continuous. This process is repeated to create a series of continuous lesions.

More specifically, by determining or understanding the spline 266 angular position with respect to the elongate member 262, the placement of the ablating portion 268 with respect to the ostium of the pulmonary vein PV can be generally determined, or otherwise known to be a minimum distance away from the pulmonary vein PV ostium. This is important for those who desire to ablate target tissue at a distance away from the ostium, from about 5 mm to about 10 mm from the ostium for example. Once a given angular relationship between the spline 266 and elongate member 262 is achieved, one can guarantee the minimum distance of the target tissue from the pulmonary vein PV ostium.

Figure 11F:
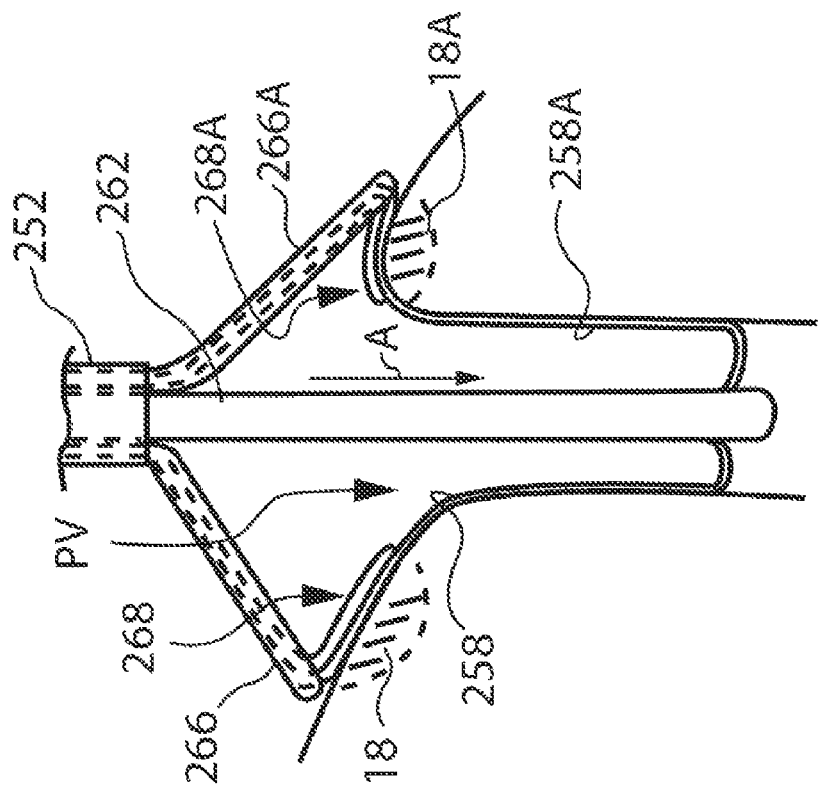
FIGS. 11F-11G depict the embodiment of FIG. 11A including multiple spline members engaging target tissue surfaces of differing contours.
Figure 11G:
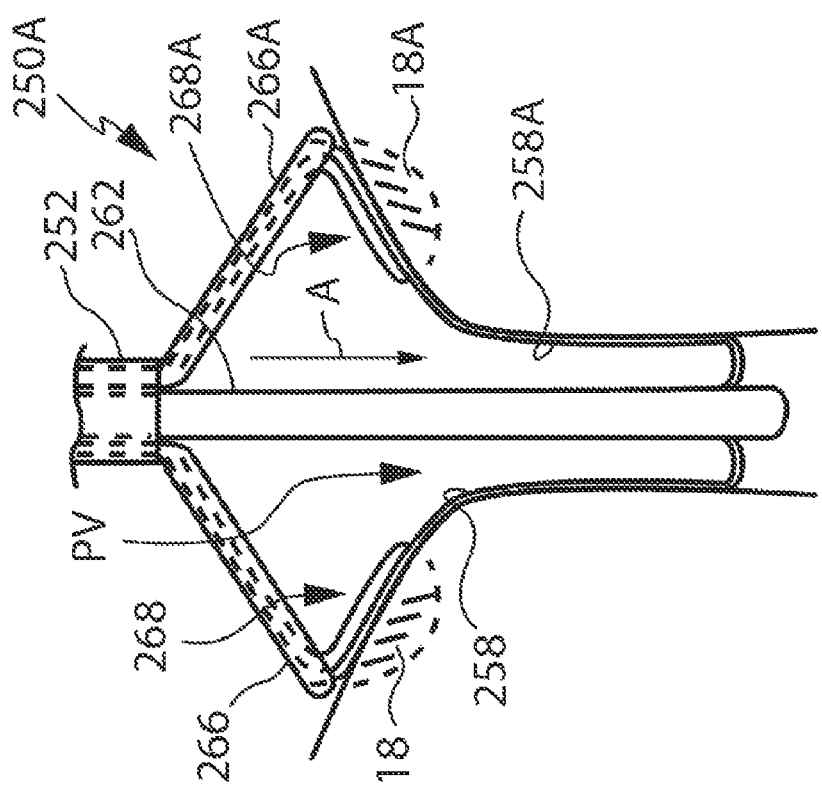
Figure 11H:
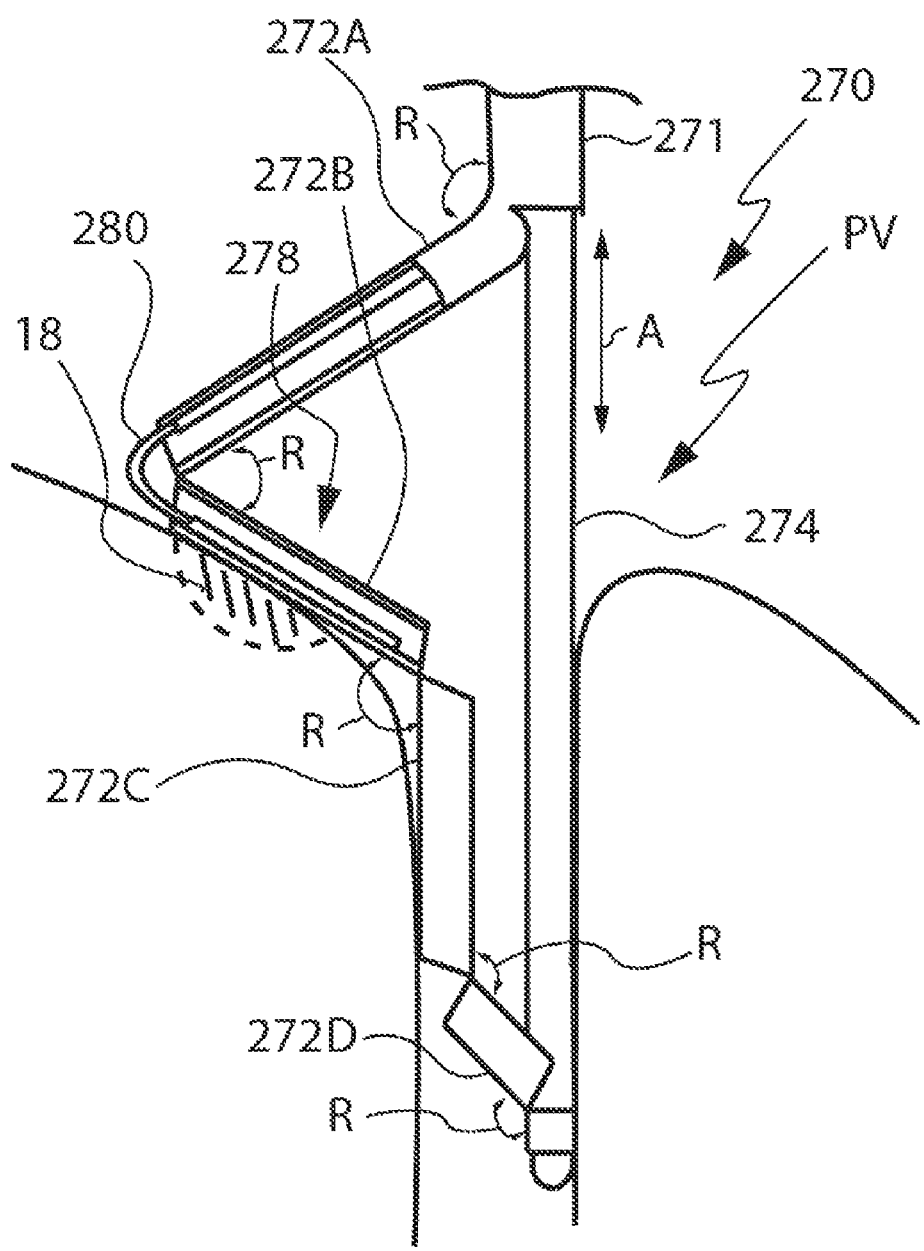
FIG. 11H depicts an elevation view of another exemplary embodiment incorporating an ablating element in accordance with various aspects of the present invention.

As will be more readily understood with respect to the discussion of the embodiment of FIG. 11H, the positioning of the ablating portion relative to the ostium of the pulmonary vein PV can be improved by further defining specific deflection points along the spring member 258. In one embodiment, at least one of the specific deflection points is a hinge. More specifically, the flexibility of the spring member 258 can be increased at points corresponding to the proximal and distal ends of spline 266. Additionally, a point of increased flexibility can be further defined a desired distance distal to the ablating portion, the desired distance representing the desired location of the ablating portion 268 with respect to the pulmonary vein PV ostium. Such points of increased flexibility can be created in any suitable manner consistent with the functionality of spring member 258. For example, recessed areas 259 can be created in member 258 at the desired points of increased flexibility as depicted in FIG. 11D. While shown having lateral recessed areas, recessed areas in the form of holes or openings formed directly in the spring member 258, as discussed above, are also contemplated.

The ablating system 252 can employ additional spline members 266 which automatically adapt to tissue surfaces surrounding a pulmonary vein ostium, allowing for the creation of multiple ablations as part of a desired lesion pattern. FIGS. 11F and 11G depict a system 250A comprising two spines 266 and 266A, similar elements of spline 266 are suffixed by the letter A in spline 266A. As shown, splines 266, 266A are operably located on opposing sides of elongate member 262, however other radial placements about member 262 are contemplated. With the addition of spline member 266A, positioned as shown, the elongate member 262 takes a more central location within the pulmonary vein PV. FIG. 11G further depicts the adaptation of the ablating portion 268A to differing tissue surface contour characteristics.

With the systems and methods disclosed and depicted in FIG. 11, as with those of FIGS. 9 and 10, a circumferential ablation about all or part of the tissue surrounding a pulmonary vein ostium can be created at a know distance with respect to a reference. The reference can be part of the ablation system itself, member 262 for example, or can be an anatomic structure or location, an inner wall of the pulmonary vein PV or the left atrial appendage LAA for example. A circumferential lesion can be created at a known distance from the pulmonary vein PV ostium or along the tissue surface extending a known distance from the pulmonary vein-cardiac tissue interface along the inner pulmonary vein wall. For illustration purposes only, sheath 252 and/or member 262 can be manipulated to adjust the position of the ablating portion 268 accordingly. The systems and methods disclosed and depicted in FIG. 11 can also be used to create one or more lesions on regions of the heart that do not include an opening e.g. a PV ostium. For example, the systems and methods disclosed and depicted in FIG. 11 can also be used to create lesion patterns shown in FIGS. 6A and 6B.

Now turning to FIG. 11H, another embodiment which places the ablating portion at a known position with respect to a reference point is shown. Ablating system 270 includes an elongate tubular member 271 which terminates in a tubular member 272. Ablation system 270 further includes an elongate member 274, similar in construction and functionality to elongate member 262 of system 250. Tubular member 272 is cut, or otherwise adapted, to define various points of increased flexibility and rotation as indicated by arrows R, further defining tubular members 272A-272D between such points. While shown as tubular members, other shapes or configurations are contemplated, such as generally planar sections or "L" shaped generally planar sections (not shown), the "L" shape corresponding to two sides of the tubular members when viewed in cross section. Additionally, as with member 262 or other portions of system 250 or system 270, tubular member 272 can include materials which provide an indication of specific orientation, such as metallic materials adapted to fluoresce.

As discussed above with reference to the embodiment of FIG. 11A, with points of increased flexibility defined as depicted in FIG. 11H, section 272C positions itself at a point parallel and adjacent to the inner wall surface of the pulmonary vein PV. As such, the ablating portion 278 can be adapted to provide or position one or more ablating elements against the target tissue 18 at a known distance from the pulmonary vein PV ostium, the distance between the point of rotation of sections 272C and 272D and the one or more ablating elements for example. It should be readily apparent that if the contour of the target tissue were sloped as depicted on the opposing side of the pulmonary vein ostium, the tubular section 272B would continue to rotate as tubular sheath 271 is further advanced, until a point when the ablating portion 278 is position generally adjacent and parallel to the desired target tissue at that location. In this way, as with the embodiment of FIG. 11A, the ablating portion of FIG. 11H is self-adjusting to the circumferential tissue about a pulmonary vein ostium, despite the contour characteristics of such circumferential tissue.

As with the embodiment of FIG. 11A, the tubular member 272 can be deployed prior to or after the elongate member 270 enters the pulmonary vein. If deployed prior to entry, once deployed, the tubular member sheath 271 and the elongate member 272 are translated as a unit in the direction toward the pulmonary vein PV as indicated by arrow A until the tubular section 272C is parallel to adjacent the inner wall surface of the pulmonary vein PV. As with spring member 258 of ablation system 250, the tubular member 272, upon deployment through advancement of sheath 271 with respect to elongate member 274, expands away from elongate member 272, the member 272 engaging a pulmonary vein PV inner wall surface, the tubular member 272, and specifically tubular member section 272C, engaging an opposing pulmonary vein wall surface. The tubular member sheath 271 is then continually advanced until the tubular section 272B is adjacent to the target tissue surface.

Alternatively, the tubular member 272 can be deployed after the sheath 272 has been placed partially within the pulmonary vein PV. During deployment, the sheath 272 is held stationary while the tubular member sheath 271 is advanced. Once the tubular section 272C appears to be adjacent and parallel to the inner wall of the pulmonary vein PV, appearing parallel to elongate member 272 for example, the tubular member sheath 271 is further advanced until the ablating portion 278 of tubular section 272B engages the target tissue surface.

While depicted as having a generally linear ablating element as part of ablating portions 268 and 278, other configurations are contemplated. For example, any ablating element arranged in any geometric planar shape defined or contemplated herein may be used as the ablating portion 268 or 278, the ablating portion 268, 278 being collapsible for translation through a delivery or steering sheath. In one embodiment, ablating portion 268 is similar to ablation portion 20 of FIG. 1. In this embodiment, ablating portion 268 is substantially non-linear when deployed but is substantially linear in the un-deployed configuration when positioned within elongate sheath 252. In a preferred embodiment, ablating portion 268 is substantially annular when deployed but is substantially linear in the un-deployed configuration when positioned within elongate sheath 252. In this embodiment, the deployment of ablating portion 268 does not change the total volume of ablating portion 268. Additionally, while depicted as a cylindrical elongate member, members 262, 272 can include longitudinal recessed areas allowing for additional infrastructure related to the transmission line 260 or obtainment of certain electrophysiological signals related to the ablation procedure, as discussed herein.

Additionally, while elongate members 262 and 274 are depicted as having generally blunt tip portions, elongate members 262 and 274 can be adapted to include a curved portion providing a more atraumatic surface for engaging the inner surfaces of the pulmonary veins. Systems 250 and 270, as with other ablation systems defined or described herein, can use any suitable delivery or steering systems known in the art or described herein to properly position the ablating portions upon the target tissue surface.

While the embodiments of FIGS. 9 through 11 have been described as having members which are advanced within the pulmonary veins, such advancement being or defining a reference point from which an ablation can occur, if desired, such reference can be made via placement of various parts of the ablation systems disclosed. and additional anatomical structures. For example, with reference to FIG. 16, the elongate members can be positioned within the left atrial appendage LAA, the ablating portions being advanced in accordance with the invention to ablate the tissue along the ridge between the LAA and the left pulmonary veins indicated by the label LPV-LAA Ridge of FIG. 16, the left superior pulmonary vein LSPV and left inferior pulmonary vein LIPV.

Moreover, the embodiments of FIGS. 9 through 11 allow for engagement of the target tissue as a desired relative location with respect to a defined reference despite the specific anatomic structure of the pulmonary vein ostium. For example, with reference to FIG. 16, the entrance to the left pulmonary veins may be common to both the superior and inferior pulmonary vein. As shown, a left pulmonary vein saddle, LPV saddle, which separates the superior and inferior veins, may be positioned within the common opening. For such anatomical structures, since the embodiments of FIGS. 9 through 11 address the target tissue generally normal to the tissue surrounding the pulmonary vein ostium, the embodiments of FIGS. 9 through 11 are well suited to create the desired lesion surrounding all or part of the common opening, including along the LPV-LAA Ridge if desired.

Now turning to FIG. 12, another exemplary embodiment having a centralized delivery point is shown. With specific reference to FIGS. 12A-12C, the ablation device 300 comprises an elongated tubular member 302 having a distal end 304 which branches into a number of spline support sections 306. The spline sections 306 are adapted to take on a first elongate cylindrical orientation for translation through a delivery or guide sheath and a second expanded orientation, as shown in FIGS. 12A-12C, once the spline sections 306 pass through the distal opening of the delivery or guide sheath. Expansion of the spline sections can be achieved through any suitable means, such as the use of memory shaped metal or plastic structures as part of the spline section structures, or other means described herein.

The distal ends of each spline support 306 are formed to provide a blunt distal tip and a planar surface 307 generally perpendicular to the longitudinal axis immediately proximal to the interface between the splines supports 306 and the tubular member 302 in order to provide a suitable surface to engage the target tissue. The one or more ablating elements are attached to the distal ends of the spline support sections 306, the spline support sections 306 holding the one or more ablating elements adjacent to the target tissue. Preferably, a thin flexible contact member 308 is attached to the distal ends of each spline, the distal surface of member 308 providing a working surface for engaging target tissue 18, as specifically shown in FIG. 12C, to which the one or more ablating elements are attached.

Spline supports 306 may be constructed at the distal portion of sheath 312 with various cuts in the out sheath surface and the distal end, providing the number of desired individual supports having desired dimensions. Alternatively, the supports may be constructed from solid cylindrical structures from which the desired material is removed to define lumens or passages through which the ablating elements or other sensors and associated infrastructure can pass. Such solid structures provide additional support for the ablating elements passing along the support member as well as providing a better foundation from which to apply force toward the target tissue, to ensure proper tissue contact is achieved for radiofrequency based ablation systems for example. The solid cylindrical structures may be formed by backfilling the distal portion of the elongated sheath 312 with a biocompatible material such as biocompatible epoxies, plastics or other polymers and then removing a portion of the material as needed. Alternatively, the structures can be formed by backfilling the distal portion with additional structures in place, tubular members having lumens passing therethrough for example to allow for the passage of the ablating elements. These tubular members could become part of the structure or can be removed once the filler has solidified or cured.

FIG. 12D is a crossectional view at the point immediately proximal to the interface between the elongated sheath 312 and the spline supports 306. As shown, the filler preferably extends proximal to the interface to provide extra support to the ablating elements 320. FIG. 12E is a crossectional view of the ablating device 300 at the midpoint along spline supports 306, with the ablating device located within the guide sheath 312. As shown, the supports 306 are adapted to cooperatively collapse and form a solid stable structure for transport through sheath 312. The antenna structures 320 are positioned within voids created during the backfilling process described above, or may be alternatively positioned through additional lumen structures as described above but not shown. The antenna structures 320 are slidably placed or snapped into position within the filler 310 of each support member 306 as to prevent their movement out from the support member when the device 300 is deployed.

As with other embodiments discussed herein, other modalities are contemplated. For example, electrodes may be formed or arranged along the contact member 308 such that, when the contact member is deployed, the electrodes are also deployed in a desired geometric shape. The electrodes may be provided in any suitable form, constructed through metal deposition or the like for example, upon the distal surface of contact member 308. Preferably, the ablation device 300 may include one or more antenna structures, structures 320A-C depicted in FIG. 12A for example. Alternatively, one antenna structure of a suitable length can be positioned along one of the support sections 306, the distal end of the antenna forming a loop about all or part of contact member 308. As depicted, each antenna structure 320 travels down a spline support 306 and then along a curvilinear section of contact member 308. The antenna structures may be electronically connected at any point proximal to the spline supports 306 or may be completed isolated, each antenna being independently operated or controlled.

While the antenna structures depicted in FIG. 12A have a generally circular crossectional area, the antenna structures can be formed through other means, such as through metal deposition techniques described above, and thus have alternative geometric crossectional areas. Furthermore, while the antenna structures are shown to be located on the distal surface of the contact member 308, the antenna structures can also be positioned or mounted on the proximal surface of contact member 308, with respect to the target tissue. As discussed above, due to the nature of microwave energy, direct contact with the target tissue is not required.

As shown in FIG. 12B, the ablation device 300 is deployed by advancing the device 300 out from within a guide sheath 312, similar to sheath 212 for example. Additional steering systems described herein may also be used to steer or otherwise position the ablating device adjacent to the desired target tissue location. As the device 300 is advanced, the support sections 306 are deployed forming or arranging the one or more ablation elements in a desired geometric shape, which in turn corresponds to a desired area ablation.

While generally shown forming a circular shape when contact member 308 is deployed, other geometric shapes as discussed herein are possible. Additional spline supports or spline supports of varying lengths and angles of deployment with respect to the guide sheath 312 may be included to further define the various shapes. Correspondingly, the contact member 308 need not be circular but can form any geometric pattern in support of the desired final geometric shape. Additionally, the angle that which the splines deploy with respect to the longitudinal axis of the elongate member 302 immediately proximal to the spline supports can be from approximately 0° to approximately 140°, bending back toward the elongate member 302.

Now turning also to FIG. 12F, an alternative ablating device 400 similar to device 300 but having generally planar splines is shown. Here, the one or more spline supports 406 are formed in a similar fashion as discussed above, however they impart an approximate 90° deflection once advanced outside the distal end of sheath 312. The deflection of the spline supports 406 leads to deployment of contact member 408, having similar advantages and utilization as member 308, the spline configuration of device 400 also allowing for the placement of ablating elements on the splines themselves, as well as along the contact member 408. Contact member 408 also optionally includes a bumper portion 408A about its outside perimeter. Bumper portion 408A provides for a raised blunt surface for contacting the target tissue when the approach toward the target tissue is at an angle, or otherwise is not normal to, the target tissue surface. The flexibility of the spline support 406 structures is adapted to allow or encourage contact between the distal surface of contact member 408 with the target tissue surface when the device 400 is further advanced toward the target tissue after initial contact between the contact member 408 and the target tissue surface is achieved. The spline members 406 can be adapted to be positioned slightly distal to the interfaces between the members 406 and the elongate member 402, forming an angle of less than 90° to allow further deflection upon tissue contact and further encouraging contact between the contact member 408 and the target tissue 18, if desired. In this way, ablation patterns can be created with less concern with respect to the approach angle between the distal end of the ablating device and the target tissue.

Contact member 408, as well as member 308, can be constructed having a distal surface which is somewhat tacky to the desired target tissue, cardiac tissue for example, to further enhance proper placement of the ablating element adjacent to the target tissue. Such material can be applied directly to the distal surface of the contact member 408, or otherwise to the surface intended to contact the target tissue 18. Ablating element areas, if required, can be masked off during manufacture to prevent overflow of material onto the ablating elements themselves. In any case, the material must be compatible with the modality used, having a low water content for microwave ablation systems for example.

Referring now to FIGS. 13A-13C, retraction of the ablating device 300 within the sheath 312 will be discussed in greater detail. FIG. 13A depicts ablating device 300 partially retracted to a point within the distal end of the guide sheath 312. As stated above, when deployed, the distal ends of each spline 306 form generally planar surfaces 307 which are adapted to engage target tissue without creating undesirable tissue damage to tissues adjacent to the target tissue. When partially retracted within sheath 312, the planar surfaces 307 form a void which is filled by the flexible contact member 308 while the device 300 is further retracted within sheath 312 in the direction indicated in FIG. 13B by arrow A.

As shown, when the ablation device 300 is initially retracted, the spline supports 306 come together, the contact member 308 folding upon itself as specifically shown in FIG. 13B. As the device 300 is further retracted, the contact member 308 folds, in response to contact with the distal end of sheath 312, into a more elongate configuration as shown, filling the space of the void 318 as necessary. The ablation device can be fully retracted for removal from the patient or can be redirected to another ablation site, another site within a heart chamber for example. While not necessary to completely retract the ablation device prior to movement of the sheath 312, doing so in some circumstances may be advantageous, providing less structure impacted by blood flow or anatomical structures within the heart during device guidance.

Any of the ablation devices disclosed herein e.g. ablation devices 300 and 400, as well as other embodiments described herein can include one or more strategically placed electrodes (not shown) for transmitting and/or receiving various signals indicative of a successful ablation procedure. For example, one electrode can be placed within the loop area and another outside of said area, the electrodes sending and receiving signals to ensure a desired block has been achieved by the currently created lesion. Similarly, one or more strategically placed electrodes (not shown) for transmitting and/or receiving various signals indicative of a successful ablation procedure can be included on any of the members or devices disclosed herein including, but not limited to positioning members, reference members, elongated members, spring members, sheaths and splines.

Turing now to FIG. 14, another ablation device 500, in accordance with the present invention is shown. As depicted, ablation device 500 exits a distal opening of a guide sheath 512, which may be similar to sheath 216, or any other guide or delivery sheath discussed herein, and takes the form of a spiral section 522 comprising approximately one or more loops. While shown generally having a conical outer surface, the spiral section 522 can take on any suitable outer surface configuration including, but not limited to, concave, cylindrical or hourglass outer surface shapes. The spiral section 522 can be formed at the distal portion of an elongate section 524 or can be separately fabricated and attached to the distal end of the elongate section 524 through any suitable means, biocompatible epoxies or material fusion for example.

The distal end of the spiral section 522 ablation portion defines a desired geometric shape, an annular shape, or other shape as described herein, for example, upon which one or more ablating elements are attached. Alternatively, the spiral section 522 can be formed by the ablating element itself, a microwave antenna for example, adapted to direct sufficient electromagnetic energy toward the target tissue 18 so as to cause tissue ablation. The antenna, for this exemplary embodiment, may form the complete spiral section or may form only a portion, which may be located at any point, or at all points, along the distal portion of spiral section 522.

The spiral distal section 522 is advantageous since it provides a flexible distal portion which ensures proper positioning of the one or more ablating elements for tissue ablation in a beating heart environment. For example, it allows the user, an electrophysiologist for example, to place the device against the target tissue, holding the point immediately proximate to the spiral section 522 relatively stationary, while the distal portion ungulates with the beating heart. The spiral section 522 of ablation device 500 is also advantageous since it forms a flexible joint 526 allowing the user to approach the target tissue from an angle, along the direction indicated by arrow A for example, the distal end of the spiral section 522 automatically deflecting to substantially contact the target tissue surface 18.

To minimize movement of the ablating device 500 across the surface of the target tissue 18, if not desired, the distal surface of the ablating device can include a tacky surface, as discussed above. Alternatively, the distal portion of the ablating device can include one or more needle-like structures which engage the target tissue and prevent movement of the ablating device 500 with respect thereto. The needle-like structures are from about 1 mm. to about 4 mm. in length and can be formed in any suitable manner, from the distal end of a spiral structure such as structure 522 for example. The needle-like structures are preferably located at the geometric center of the distal surface, but other locations are contemplated, such as laterally spaced from the ablating portion itself. With the anchor laterally positioned, spaced apart from the ablating portion, the anchor can define a reference point from which an area ablation can be created by structure 522, in similar fashion as discussed above with respect to the embodiments of FIGS. 9 through 11, creating ablations relative to various reference points. Additionally, such anchoring devices used in conjunction with other embodiments discussed herein are also contemplated.

Regardless whether the spiral section 522 has a general conical or convex surface facing the target tissue, it should be readily understood that if one continues to advance the spiral section 522 toward target tissue, additional loop sections of spiral section 522 will engage the target tissue surface. In this way, ablations of additional geometric characteristics can be created. For example, given a conical surface spiral section facing the target tissue, as the depicted spiral section 522, as the user advances the spiral section toward the target tissue, the inner loops of the spiral section sequentially engaging the target tissue, a surface ablation ranging from a circular surface ablation corresponding to the outer perimeter of the spiral to a complete surface area ablation can be created. Alternatively, when advancing a convex shaped spiral section (not shown) toward the target tissue, the outer loops of the spiral section sequentially engaging the target tissue, a surface ablation ranging from about a point ablation to a complete surface area ablation can be created. In the later configuration, as the spiral section 522 is further advanced from a starting point contact with the target tissue, surface ablations of increasing diameters are created.

As discussed relative to other embodiments herein, once the ablating device 500 is positioned, ablation energy is transferred or transmitted to the one or more ablating elements and a lesion is created, as part of a desired lesion pattern. It should be apparent to those skilled in the art that as the ablating device 500 is slightly retracted and repositioned for subsequent ablation procedures, the spiral device 522 incorporating the flexible joint 526 will realign itself to a normal position, for example the longitudinal axis of the spiral section 522 generally parallel to, although not necessarily aligned with, the longitudinal axis of the elongated member 524.

The elongate member 524, as well as spiral section 522, can include lumens as necessary for passing infrastructure related to the utilized modality, transmitting ablative energy from a source location to the one or more ablating elements for example.

While shown having generally a centralized point of delivery, e.g. the longitudinal axis of the distal end of the elongate member 524 is the longitudinal axis of the spiral section 522 in an undeflected state, other points of delivery are contemplated. Additionally, while shown having or forming approximately 2 loops, spiral section 522 can be constructed from any. number of loops, the loop number and spacing therebetween each loop defining the deflection characteristics of the flexible joint 526, as well as the geometric shape of the ablating portion. Where applicable, the additional number of loops may form additional structures which aide in the tissue ablation process, the loops forming a reflector for a distal mounted spiral antenna structure for example, the loops preventing stray electromagnetic energy from entering the blood flow, redirecting the energy toward the target tissue. Moreover, the loops need not be formed from a continuously curved section, but can be formed from any suitable linear section, curvilinear section, or a combination. Preferably, the geometric shape of the spiral section is consistent from one loop to another so that when the spiral section is compressed as it is advanced toward the target tissue, the loops will be positioned substantially adjacent to each other in or along the same plane.

Additionally, for suitable ablation systems, the spiral section 522 may be placed within a balloon structure, or otherwise provided with an outer covering to limit direct contact with bodily fluids, contact with the blood pool inside a chamber of the heart for example. Such suitable ablation systems include, but are not limited to, cryogenic or microwave based systems, the ablative energy being able to pass through the balloon or encasing structures, the structures absorbing a minimal amount of energy allowing the transmission of a substantial amount of ablative energy therethrough.

Now turning to FIGS. 15A and 15B, two additional exemplary embodiments incorporating flexible joints, and other advantages discussed herein, are shown. More specifically, FIG. 15A depicts an ablation device 600 having a flexible joint 622 and a distal ablating portion, such as the ablating portion of the FIG. 12F embodiment comprising multiple splines and a contact member 608. The flexible joint 622 comprises a ball 632 and socket 630 construction operably attached at the distal end of an elongate member 624. The ball 632 is attached to a narrowed stem portion 634 which allows the distal portion to deflect toward a conical distal surface of the socket, as shown, relative to the longitudinal axis of the elongate delivery sheath 624 in response to engaging the target tissue surface 18.

As shown, when the ablating device 600 is advanced in the direction indicated by arrow A and approaches the target tissue substantially normal to the longitudinal axis of the elongate member 624, the ablating portion of the device 600 directly engages the target tissue. However, as shown in dashed line, if the ablating device 600 is advanced and approaches the target tissue at an angle, the flexible joint 622 allows the distal end of the ablating device to rotate and substantially engage the target tissue surface about a substantial portion of the ablating portion.

As with other devices, the ablating device 600 can be repositioned for the creation of subsequent ablations, as part of a desired lesion set. When the distal end of the ablating device 600 is retracted, such that the flexible joint 622 is retracted to a point within the delivery sheath 616, the ablating portion of the ablating device 600 is realigned with the elongate member 624 and the distal end of the elongate member 624 can be redirected toward another desired target tissue location, through steering mechanisms described herein for example. Once again the ablating portion can be extended to engage the target tissue 18 at this new location, the distal ablating portion deflecting as necessary, and a subsequent ablation or lesion is created.

Alternatively, using simple rotational or translational movement with reference to steering systems discussed herein in accordance with the present invention, the distal end of the ablating device can slide or otherwise move along the target tissue 18 surface to a new location where a subsequent lesion is created. Alternative, as discussed above, the distal surface can be adapted to be tacky or may include one or more needle-like structures to prevent movement, if desired. In such a case, the ablating portion would need to be fully retracted off the target tissue surface, moved, and then placed upon the new target tissue surface.

Turning now to FIG. 15B an additional ablating device 700 is shown incorporating a flexible joint 722 comprising a coiled spring structure or similar structure which has the flexibility characteristics of an appropriate coiled spring. The coiled spring operates in a similar fashion as the flexible joint 722, but does not need to be retracted into an elongate sheath, sheath 716 for example, to be realigned. Rather, the longitudinal spring force of the coil, as with the flexible joint depicted in FIG. 14, automatically aligns the distal ablating portion when retracted away from the target tissue 18 surface. Preferably, the spring is embedded within or otherwise covered with a flexible membrane of biocompatible material which will allow the spring to deflect during use while providing a relatively smooth outer surface which resists the formation of blood clots thereon.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed, upon review of the present specification. The claims are intended to cover such modifications and devices.

We claim:

1. A method of treating tissue comprising:
positioning a treatment system adjacent to an anatomical site, where the treatment system includes an ablation device, a first elongate arm and a second elongate arm, where the ablation device and second elongate arms are coupled by a flexible member that couples the ablation device to a distal portion of the second elongate arm such that the ablation device, the second arm and the flexible member define a closed loop assembly extending from the first elongate arm;
stabilizing the closed loop assembly within the anatomical site by manipulating both elongate arms to force the closed loop assembly against tissue;
advancing the ablation device through the first arm and positioning the ablation device using the flexible member such that the stabilized closed loop assembly stabilizes the ablation device;
treating a first region of tissue adjacent to the flexible member with the ablation device; and comprising placing at least one electrode against tissue to transmit and receive electrophysiological signals from the tissue where the least one electrode is located on the flexible member.

2. The method of claim 1, where the loop assembly comprises a steering system.

3. The method of claim 2, where the steering system comprises at least one steering wire.

4. The method of claim 2, where the steering system enables deflection in more than one plane.

5. The method of claim 1, where a portion of the loop assembly comprises materials adapted to fluoresce and where the method further comprises determining an orientation of the loop assembly by the fluorescence of the materials.

6. The method of claim 1, further comprising repositioning the ablation device to a second region of tissue adjacent to the stabilized flexible member and ablating the second region of tissue.

7. The method of claim 6, where the first and second regions of tissue are continuous.

8. The method of claim 6, further comprising manipulating one or both of the elongate arms to reposition the flexible member, which repositions the ablation device to the second region of tissue along the repositioned flexible member and ablating the second region of tissue.

9. The method of claim 6, where ablating the second region of tissue forms an area ablation pattern between the first and second regions of tissue.

10. The method of claim 1, where the least one electrode is located on one of the elongate arms.

11. The method of claim 1, where stabilizing the closed loop assembly comprises stabilizing the closed loop assembly by applying contact forces against anatomical structures.

12. The method of claim 1, further comprising advancing at least one of the elongate arms into a pulmonary vein.

13. The method of claim 1, where the ablation device is steerable, where the method comprises steering the ablation device during positioning of the treatment system.

14. The method of claim 1, where the ablation device is able to abate tissue regions that is not directly adjacent to the flexible member.

15. The method of claim 1, where the ablation device applies an ablation energy selected from the group consisting of radiofrequency energy, microwave energy, infrared energy; thermal energy, photonic energy, laser energy, high energy particles, ultrasonic energy, cryoablation, and chemical.

16. The method of claim 1, where the first and/or the second elongate arm is stiffer than the flexible member.

17. A method of treating tissue comprising the steps of:
positioning a treatment system adjacent to an anatomical site, where the treatment system includes an ablation device, a first elongate arm and a second elongate arm, where the ablation device and second elongate arm are coupled by a mechanical member where advancement of the second elongate arm causes the mechanical member to reposition the ablation device, the second arm and the mechanical member define a closed loop assembly, where a portion of the ablation device passes through the mechanical member further comprising at least one electrode on the mechanical member;
advancing the ablation device out of the distal portion of the first elongate arm;
manipulating the ablation device to the treatment site by manipulating the mechanical member having the portion of the ablation device located therein; and
treating a first region of tissue with the ablation device.

18. The method of claim 17, where the ablation device is advanceable through the mechanical member, and where the mechanical member comprises an opening such that treating the first region of tissue comprises treating tissue through the opening.

19. The method of claim 17, where at least the first or second elongate arm comprises a steering system.

20. The method of claim 19, where the steering system comprises at least one steering wire.

21. The method of claim 17, where a portion of the loop assembly comprises materials adapted to fluoresce and where the method further comprises determining an orientation of the loop assembly by the fluorescence of the materials.

22. The method of claim 17, further comprising repositioning the ablation device to a second region of tissue adjacent to the stabilized mechanical member and ablating the second region of tissue.

23. The method of claim 22, where the first and second regions of tissue are continuous.

24. The method of claim 22, further comprising manipulating one or both of the elongate arms to reposition the mechanical member, which repositions the ablation device to the second region of tissue along the repositioned mechanical member and ablating the second region of tissue.

25. The method of claim 22, where ablating the second region of tissue forms an area ablation pattern between the first and second regions of tissue.

26. The method of claim 17, further comprising placing electrodes against tissue to transmit and receive electrophysiological signals from the tissue.

27. The method of claim 26, where electrodes are located on one of the elongate arms.

28. The method of claim 17, further comprising stabilizing the closed loop assembly by applying contact forces against anatomical structures.

29. The method of claim 17, further comprising advancing at least one of the elongate arms into a pulmonary vein.

30. The method of claim 17, where the ablation device is steerable, where the method comprises steering the ablation device during positioning of the ablation device.

31. The method of claim 17, where the ablation device is able to abate the first region of tissue, where the first region is not directly adjacent to the mechanical member.

32. The method of claim 17, where the ablation device applies an ablation energy selected from the group consisting of radiofrequency energy, microwave energy, infrared energy; thermal energy, photonic energy, laser energy, high energy particles, ultrasonic energy, cryoablation, and chemical.

33. The method of claim 17, where the first and/or the second elongate arm is stiffer than the mechanical member.

34. A method of treating tissue comprising:
positioning a treatment system adjacent to an anatomical site, where the treatment system includes an ablation device, a first elongate arm and a second elongate arm, where the ablation device and second elongate arms are coupled by a flexible member that couples the ablation device to a distal portion of the second elongate arm such that the ablation device, the second arm and the flexible member define a closed loop assembly extending from the first elongate arm, where the flexible member further comprises at least one ablation electrode;
stabilizing the closed loop assembly within the anatomical site by manipulating both elongate arms to force the closed loop assembly against tissue;

advancing the ablation device through the first arm and positioning the ablation device using the flexible member such that the stabilized closed loop assembly stabilizes the ablation device;
treating a first region of tissue adjacent to the flexible member with the ablation device; and
ablating tissue with the ablation electrode.

35. The method of claim 34, where the loop assembly comprises a steering system.

36. The method of claim 34, where the steering system comprises at least one steering wire.

37. The method of claim 34, where the steering system enables deflection in more than one plane.

38. The method of claim 34, where a portion of the loop assembly comprises materials adapted to fluoresce and where the method further comprises determining an orientation of the loop assembly by the fluorescence of the materials.

39. The method of claim 34, further comprising repositioning the ablation device to a second region of tissue adjacent to the stabilized flexible member and ablating the second region of tissue.

40. The method of claim 39, where the first and second regions of tissue are continuous.

41. The method of claim 39, further comprising manipulating one or both of the elongate arms to reposition the flexible member, which repositions the ablation device to the second region of tissue along the repositioned flexible member and ablating the second region of tissue.

42. The method of claim 39, where ablating the second region of tissue forms an area ablation pattern between the first and second regions of tissue.

43. The method of claim 39, where the least one electrode is located on one of the elongate arms.

44. The method of claim 39, where stabilizing the closed loop assembly comprises stabilizing the closed loop assembly by applying contact forces against anatomical structures.

45. The method of claim 39, further comprising advancing at least one of the elongate arms into a pulmonary vein.

46. The method of claim 39, where the ablation device is steerable, where the method comprises steering the ablation device during positioning of the treatment system.

47. The method of claim 39, where the ablation device is able to abate tissue regions that is not directly adjacent to the flexible member.

48. The method of claim 39, where the ablation device applies an ablation energy selected from the group consisting of radiofrequency energy, microwave energy, infrared energy; thermal energy, photonic energy, laser energy, high energy particles, ultrasonic energy, cryoablation, and chemical.

49. The method of claim 39, where the first and/or the second elongate arm is stiffer than the flexible member.

50. The method of claim 39, where positioning the ablation device using the flexible member comprises deploying the ablation device from the loop assembly.

51. A method of treating tissue comprising the steps of:
positioning a treatment system adjacent to an anatomical site, where the treatment system includes an ablation device, a first elongate arm and a second elongate arm, where the ablation device and second elongate arm are coupled by a mechanical member where advancement of the second elongate arm causes the mechanical member to reposition the ablation device, the second arm and the mechanical member define a closed loop assembly, where a portion of the ablation device passes through the mechanical member;
advancing the ablation device out of the distal portion of the first elongate arm;
manipulating the ablation device to the treatment site by manipulating the mechanical member having the portion of the ablation device located therein;
treating a first region of tissue with the ablation device; and
placing electrodes against tissue to transmit and receive electrophysiological signals from the tissue where the electrodes are located on the mechanical member.

52. The method of claim 51, where the ablation device is advanceable through the mechanical member, and where the mechanical member comprises an opening such that treating the first region of tissue comprises treating tissue through the opening.

53. The method of claim 51, where at least the first or second elongate arm comprises a steering system.

54. The method of claim 53, where the steering system comprises at least one steering wire.

55. The method of claim 51, where a portion of the loop assembly comprises materials adapted to fluoresce and where the method further comprises determining an orientation of the loop assembly by the fluorescence of the materials.

56. The method of claim 51, further comprising repositioning the ablation device to a second region of tissue adjacent to the stabilized mechanical member and ablating the second region of tissue.

57. The method of claim 56, where the first and second regions of tissue are continuous.

58. The method of claim 56, further comprising manipulating one or both of the elongate arms to reposition the mechanical member, which repositions the ablation device to the second region of tissue along the repositioned mechanical member and ablating the second region of tissue.

59. The method of claim 56, where ablating the second region of tissue forms an area ablation pattern between the first and second regions of tissue.

60. The method of claim 51, further comprising placing electrodes against tissue to transmit and receive electrophysiological signals from the tissue.

61. The method of claim 60, where electrodes are located on one of the elongate arms.

62. The method of claim 51, further comprising stabilizing the closed loop assembly by applying contact forces against anatomical structures.

63. The method of claim 51, further comprising advancing at least one of the elongate arms into a pulmonary vein.

64. The method of claim 51, where the ablation device is steerable, where the method comprises steering the ablation device during positioning of the ablation device.

65. The method of claim 51, where the ablation device is able to abate the first region of tissue, where the first region is not directly adjacent to the mechanical member.

66. The method of claim 51, where the ablation device applies an ablation energy selected from the group consisting of radiofrequency energy, microwave energy, infrared energy; thermal energy, photonic energy, laser energy, high energy particles, ultrasonic energy, cryoablation, and chemical.

67. The method of claim 51, where the first and/or the second elongate arm is stiffer than the mechanical member.

68. The method of claim 51, where positioning the treatment system using the mechanical member comprises deploying the ablation device from the loop assembly.

69. A method of treating tissue comprising the steps of:
positioning a treatment system adjacent to an anatomical site, where the treatment system includes an ablation device, a first elongate arm and a second elongate arm, where the ablation device and second elongate arm are coupled by a mechanical member where advancement of the second elongate arm causes the mechanical member to reposition the ablation device, the second arm and the mechanical member define a closed loop assembly, where a portion of the ablation device passes through the mechanical member where the mechanical member further comprises at least one ablation electrode, and where the method further comprises ablating tissue with the ablation electrode;

advancing the ablation device out of the distal portion of the first elongate arm;

manipulating the ablation device to the treatment site by manipulating the mechanical member having the portion of the ablation device located therein; and treating a first region of tissue with the ablation device.

70. The method of claim 69, where the ablation device is advanceable through the mechanical member, and where the mechanical member comprises an opening such that treating the first region of tissue comprises treating tissue through the opening.

71. The method of claim 69, where at least the first or second elongate arm comprises a steering system.

72. The method of claim 71, where the steering system comprises at least one steering wire.

73. The method of claim 69, where a portion of the loop assembly comprises materials adapted to fluoresce and where the method further comprises determining an orientation of the loop assembly by the fluorescence of the materials.

74. The method of claim 69, further comprising repositioning the ablation device to a second region of tissue adjacent to the stabilized mechanical member and ablating the second region of tissue.

75. The method of claim 74, where the first and second regions of tissue are continuous.

76. The method of claim 74, further comprising manipulating one or both of the elongate arms to reposition the mechanical member, which repositions the ablation device to the second region of tissue along the repositioned mechanical member and ablating the second region of tissue.

77. The method of claim 74, where ablating the second region of tissue forms an area ablation pattern between the first and second regions of tissue.

78. The method of claim 69, further comprising placing electrodes against tissue to transmit and receive electrophysiological signals from the tissue.

79. The method of claim 78, where electrodes are located on one of the elongate arms.

80. The method of claim 69, further comprising stabilizing the closed loop assembly by applying contact forces against anatomical structures.

81. The method of claim 69, further comprising advancing at least one of the elongate arms into a pulmonary vein.

82. The method of claim 69, where the ablation device is steerable, where the method comprises steering the ablation device during positioning of the ablation device.

83. The method of claim 69, where the ablation device is able to abate the first region of tissue, where the first region is not directly adjacent to the mechanical member.

84. The method of claim 69, where the ablation device applies an ablation energy selected from the group consisting of radiofrequency energy, microwave energy, infrared energy; thermal energy, photonic energy, laser energy, high energy particles, ultrasonic energy, cryoablation, and chemical.

85. The method of claim 69, where the first and/or the second elongate arm is stiffer than the mechanical member.

86. The method of claim 69, where positioning the treatment system using the mechanical member comprises deploying the ablation device from the loop assembly.

* * * * *